(12) United States Patent
Oost et al.

(10) Patent No.: US 7,803,834 B2
(45) Date of Patent: Sep. 28, 2010

(54) SUBSTITUTED OXINDOLE DERIVATIVES, DRUGS CONTAINING SAID DERIVATIVES AND THE USE THEREOF

(75) Inventors: Thorsten Oost, Ludwigshafen (DE); Wilfried Lubisch, Heidelberg (DE); Wolfgang Wernet, Ludwigshafen (DE); Wilfried Hornberger, Ludwigshafen (DE); Liliane Unger, Ludwigshafen (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 11/886,730

(22) PCT Filed: Mar. 23, 2006

(86) PCT No.: PCT/EP2006/002685
§ 371 (c)(1),
(2), (4) Date: Dec. 12, 2008

(87) PCT Pub. No.: WO2006/100082
PCT Pub. Date: Sep. 28, 2006

(65) Prior Publication Data
US 2009/0163492 A1    Jun. 25, 2009

Related U.S. Application Data

(60) Provisional application No. 60/664,759, filed on Mar. 24, 2005.

(30) Foreign Application Priority Data

Mar. 26, 2005 (DE) .................... 10 2005 014 628
Mar. 31, 2005 (DE) .................... 10 2005 015 957

(51) Int. Cl.
*A61K 31/403* (2006.01)
*C07D 209/32* (2006.01)

(52) U.S. Cl. ........................ 514/418; 548/486
(58) Field of Classification Search ............. 514/418; 548/486
See application file for complete search history.

(56) References Cited

U.S. PATENT DOCUMENTS 5,594,023 A * 1/1997 Wagnon et al. ............. 514/423

FOREIGN PATENT DOCUMENTS

| WO | WO 93/15051 | 8/1993 |
|---|---|---|
| WO | WO 95/18105 A | 7/1995 |
| WO | WO 98/25901 | 6/1998 |
| WO | WO 01/55130 A | 8/2001 |
| WO | WO 01/55134 A | 8/2001 |
| WO | WO 01/64668 | 9/2001 |
| WO | WO 01/98295 A | 12/2001 |
| WO | WO 03/08407 | 1/2003 |
| WO | WO 2005/030755 A | 4/2005 |
| WO | WO 2006/072458 A | 7/2006 |

OTHER PUBLICATIONS

Stella, Valentino J, Expert Opinion of Therapeutic Patents, Prodrugs as therapeutics, 2004 14(3): 277-280.*
Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10), (2004) 2394-2404.*

* cited by examiner

*Primary Examiner*—Kamal A Saeed
*Assistant Examiner*—Samantha L Shterengarts
(74) *Attorney, Agent, or Firm*—Lisa V. Mueller; Polsinelli Shughart PC

(57) ABSTRACT

The invention relates to novel oxindol derivative of general formula (I), wherein substituents $R^1$, $R^2$, A, B and Y are such as defined in a claim 1. Drugs containing said derivatives and the use thereof for preventing and/or treating vassopress- and/or oxytocin-dependent-diseases are also disclosed.

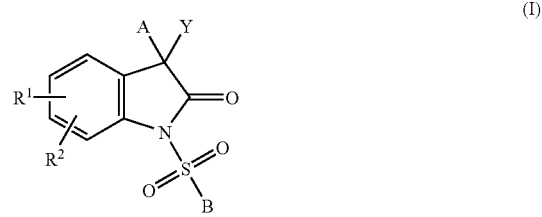

24 Claims, No Drawings

SUBSTITUTED OXINDOLE DERIVATIVES, DRUGS CONTAINING SAID DERIVATIVES AND THE USE THEREOF

The present invention relates to novel substituted oxindole derivatives, medicaments comprising them and the use thereof for the treatment of diseases.

Vasopressin is an endogenous hormone which exerts various effects on organs and tissues. It is expected that the vasopressin system is involved in various pathological conditions such as, for example, heart failure and high blood pressure. At present, three receptors (V1a, V1b or V3 and V2) via which vasopressin mediates its numerous effects are known. Antagonists of these receptors are therefore investigated as possible novel therapeutic approaches to the treatment of diseases (M. Thibonnier, Exp. Opin. Invest. Drugs 1998, 7(5), 729-740). It has been found, for example, that a selective antagonist of the vasopressin V1b receptor exerts anxiolytic and antidepressant effects in animal models (Griebel et al., PNAS 2002, 99, 6370; Serradeil-Le Gal et al., J. Pharm. Exp. Ther. 2002, 300, 1122). Since the models described have a certain predictive value for the clinical effects to be expected, antagonists of the V1b receptor are of particular interest for the treatment of emotional disturbances or disorders such as, for example, stress, anxiety states and/or depression.

The present application describes novel substituted oxindoles which have a (hetero)arylsulfonyl group in position 1. 1-Phenylsulfonyl-1,3-dihydro-2H-indol-2-ones have previously been described as ligands of the vasopressin receptors. WO 93/15051, WO95/18105, WO 98/25901, WO 01/55130, WO 01/55134, WO 01/64668 and WO 01/98295 have described derivatives derived from the oxindole structure and having arylsulfonyl groups in position 1. These compounds differ substantially in the substitution in position 3.

In particular, WO 93/15051 and WO 98/25901 describe 1-phenylsulfonyl-1,3-dihydro-2H-indol-2-ones in which the oxindole structure is substituted in position 3 by two alkyl radicals which may likewise be a cycloalkyl radical (spirolinkage) as ligands of vasopressin receptors. Alternative possibilities are for the spiro ring to comprise heteroatoms such as oxygen and nitrogen (optionally with substituents).

WO 95/18105 describes 1-phenylsulfonyl-1,3-dihydro-2H-indol-2-ones which have a nitrogen atom in position 3 as ligands of vasopressin receptors. In addition, radicals which may be alkyl, cycloalkyl, phenyl or benzyl radicals are linked in position 3 (in each case optionally with substituents).

Other publications, for example WO 01/55130, describe compounds which have nitrogen-containing rings (e.g. proline, homoproline, morpholine, tetrahydroisoquinoline, dihydroindole; in each case optionally with substituents) which are linked via their nitrogen atom to position 3 of the oxindole structure but which are substituted by phenylsulfonyl or phenyl groups (optionally with substituents) both in position 1 and in position 3 on the oxindole ring.

WO 03/008407 describes 1-phenylsulfonyloxindoles in which pyridylpiperazines are linked in position 3 via an oxycarbonyl group to the oxindole.

It is an object of the present invention to provide further compounds for the treatment or prophylaxis of various vasopressin-dependent diseases. The compounds are intended to show high activity, especially an antagonistic activity, on the human vasopressin V1b receptor.

The object is achieved by compounds of the general formula (I),

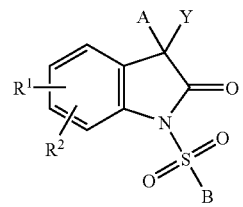

(I)

in which

A is an aromatic, heteroaromatic, partly aromatic or partly heteroaromatic mono- or bicyclic radical which consists of 2, 3, 4, 5, 6, 7, 8, 9 or 10 carbon atoms and 0, 1, 2, 3 or 4 nitrogen atoms and/or 0, 1 or 2 oxygen atoms and/or 0, 1 or 2 sulfur atoms, and which is substituted by the radical $R_A^1$ and may besides be additionally substituted by 1, 2 or 3 radicals $R_A^{11}$, $R_A^{12}$ and/or $R_A^{13}$ which are selected independently of one another and independent of their respective occurrence from the group consisting of hydrogen, chlorine, bromine, iodine, fluorine, CN, $CF_3$, $OCF_3$, $OCHF_2$, $CO-NH_2$, $CO-NH(C_1-C_4$-alkyl), $CO-N(C_1-C_4$-alkyl)$(C_1-C_4$-alkyl), $NH_2$, $NH(C_1-C_4$-alkyl), $N(C_1-C_4$-alkyl)$(C_1-C_4$-alkyl), NHCHO, $NH-CO-NH_2$, $NH-CO(C_1-C_4$-alkyl), $NO_2$, OH, $O-C_1-C_4$-alkyl, $O-C_0-C_4$-alkylene-phenyl, phenyl, $C_1-C_6$-alkyl, $C_1-C_6$-haloalkyl, $C_2-C_6$-alkenyl and $C_2-C_6$-alkynyl, in which $R_A^1$ is $R_A^2-(C_1-C_4$-alkylene)-$R_A^4$, $R_A^2$ is selected from the group consisting of
($C_0-C_4$-alkylene)-O, ($C_0-C_4$-alkylene)-$NR_A^5$, ($C_0-C_4$-alkylene)-S, ($C_0-C_4$-alkylene)-SO, ($C_0-C_4$-alkylene)-$SO_2$, ($C_0-C_4$-alkylene)-CO, ($C_0-C_4$-alkylene)-$NR_A^5$—CO, ($C_0-C_4$-alkylene)-CO—$NR_A^5$, ($C_0-C_4$-alkylene)-CO—O, ($C_0-C_4$-alkylene)-$NR_A^5$—$SO_2$, ($C_0-C_4$-alkylene)-$SO_2$—$NR_A^5$, ($C_0-C_4$-alkylene)-$NR_A^5$—CO—$NR_A^6$, ($C_0-C_4$-alkylene)-O—CO—$NR_A^5$, ($C_0-C_4$-alkylene)-$NR_A^5$—CO—O and single bond, $R_A^4$ is selected from the group consisting of
$NH_2$, $NH(C_1-C_4$-alkyl), $N(C_1-C_4$-alkyl)$(C_1-C_4$-alkyl), $NH(C_1-C_4$-alkylene-O—$C_1-C_4$-alkyl), $N(C_1-C_4$-alkyl)$(C_1-C_4$-alkylene-O—$C_1-C_4$-alkyl), NH—CHO, $N(C_1-C_4$-alkyl)-CHO, $NH-CO-NH_2$, $N(C_1-C_4$-alkyl)-CO—$NH_2$, $NH-CO-C_1-C_4$-alkyl, $N(C_1-C_4$-alkyl)-CO—$C_1-C_4$-alkyl, $NH-SO_2-C_1-C_4$-alkyl, $N(C_1-C_4$-alkyl)-$SO_2$—$C_1-C_4$-alkyl and ring $R_A^8$, $R_A^5$, $R_A^6$, $R_A^9$ are selected independently of one another and independent of their respective occurrence from the group consisting of hydrogen, $C_1-C_4$-alkyl and $C_1-C_4$-haloalkyl;

$R_A^8$ is selected from the group consisting of the respective individual radicals

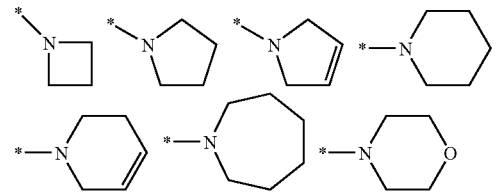

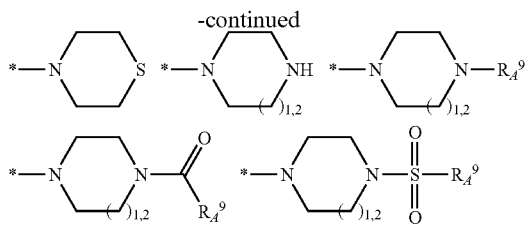

B is an aromatic, heteroaromatic, partly aromatic or partly heteroaromatic mono- or bicyclic radical which consists of 2, 3, 4, 5, 6, 7, 8, 9 or 10 carbon atoms and 0, 1, 2, 3 or 4 nitrogen atoms and/or 0, 1 or 2 oxygen atoms and/or 0, 1 or 2 sulfur atoms, and which may be substituted by 1, 2 or 3 radicals $R_B^1$, $R_B^2$ and/or $R_B^3$, where $R_B^1$, $R_B^2$ and $R_B^3$ are selected independently of one another and independent of their respective occurrence from the group consisting of hydrogen, chlorine, bromine, iodine, fluorine, CN, $CF_3$, $OCF_3$, $OCHF_2$, $CO-NH_2$, $CO-NH(C_1-C_4$-alkyl), $CO-N(C_1-C_4$-alkyl)$(C_1-C_4$-alkyl), $NH_2$, $NH(C_1-C_4$-alkyl), $N(C_1-C_4$-alkyl)$(C_1-C_4$-alkyl), $NH-CHO$, $NH-CO-NH_2$, $NH-CO-C_1-C_4$-alkyl, $NO_2$, OH, $O-C_1-C_4$-alkyl, $O-C_0-C_4$-alkylene-phenyl, phenyl, $C_1-C_6$-alkyl, $C_1-C_6$-haloalkyl, $C_2-C_6$-alkenyl and $C_2-C_6$-alkynyl;

$R^1$ is selected from the group consisting of hydrogen, chlorine, bromine, iodine, fluorine, CN, $CF_3$, $OCF_3$, $OCHF_2$, $CO-NH_2$, $CO-NH(C_1-C_4$-alkyl), $CO-N(C_1-C_4$-alkyl)$(C_1-C_4$-alkyl), $NH_2$, $NH(C_1-C_4$-alkyl), $N(C_1-C_4$-alkyl)$(C_1-C_4$-alkyl), $NH-CHO$, $NH-CO-NH_2$, $NH-CO-C_1-C_4$-alkyl, $NO_2$, OH, $O-C_1-C_4$-alkyl, $O-C_0-C_4$-alkylene-phenyl, phenyl, $C_1-C_6$-alkyl, $C_1-C_6$-haloalkyl, $C_2-C_6$-alkenyl and $C_2-C_6$-alkynyl, $R^2$ is selected from the group consisting of hydrogen, $C_1-C_4$-alkyl, $O-C_1-C_4$-alkyl, chlorine and fluorine, Y is a radical

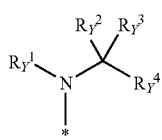

in which $R_Y^1$ is selected from the group consisting of hydrogen, $C_1-C_4$-alkyl and $C_1-C_4$-haloalkyl;

$R_Y^2$ is selected from the group consisting of hydrogen; phenyl; phenyl substituted by 1, 2, 3, 4 or 5 radicals $R_{Ph}^1$, $R_{Ph}^2$, $R_{Ph}^3$, $R_{Ph}^4$ and/or $R_{Ph}^5$ which are selected independently of one another from the group consisting of hydrogen, halogen, $C_1-C_6$-alkyl and $C_1-C_6$-alkoxy; $C_1-C_6$-alkyl; $C_3-C_7$-cycloalkyl and $C_1-C_6$-haloalkyl;

in which $R_Y^1$ and $R_Y^2$ may also form together with the atoms to which they are bonded a 4-, 5-, 6- or 7-membered, saturated or unsaturated ring which may, instead of a ring C atom, also include a heteroatom selected from the group consisting of O, S and $NR_Y^5$ as further ring member, where $R_Y^5$ may independent of its respective occurrence be hydrogen, $C_1-C_4$-alkyl or $CO-C_1-C_4$-alkyl, and where the ring may have one or two substituents $R_Y^6$ and $R_Y^7$ which are selected independently of one another and independent of their respective occurrence from the group consisting of the radicals hydrogen, chlorine, bromine, iodine, fluorine, CN, $CF_3$, $OCF_3$, $OCHF_2$, $CO-NH_2$, $CO-NH(C_1-C_4$-alkyl), $CO-N(C_1-C_4$-alkyl)$(C_1-C_4$-alkyl), $NH_2$, $NH(C_1-C_4$-alkyl), $N(C_1-C_4$-alkyl)$(C_1-C_4$-alkyl), $NH-CHO$, $NH-CO-NH_2$, $NH-CO-C_1-C_4$-alkyl, OH, $O-C_1-C_4$-alkyl, $O-CO-C_1-C_4$-alkyl, $O-(CH_2)_{0-2}$-phenyl, phenyl, $C_1-C_6$-alkyl, or $R_Y^6$ and $R_Y^7$ may also independent of their respective occurrence form together with the C atoms to which they are bonded a fused phenyl ring or a fused 5- or 6-membered, aromatic heterocycle which, besides C atoms, includes as ring members 1, 2, 3 or 4 identical or different heteroatoms as ring members which may be selected independently of one another from the group consisting of nitrogen, oxygen and sulfur, $R_Y^3$ is selected from the group consisting of hydrogen, $C_1-C_4$-alkyl and $C_1-C_4$-haloalkyl;

$R_Y^4$ is selected from the group consisting of hydrogen, $CO-NR_Y^{21}R_Y^{22}$, $CO-C_1-C_4$-alkyl, COOH and $CO-O-C_1-C_4$-alkyl, $R_Y^{21}$, $R_Y^{22}$ are selected independently of one another and independent of their respective occurrence from the group consisting of hydrogen, $C_1-C_4$-alkyl and $C_1-C_4$-haloalkyl;

or $R_Y^{21}$ and $R_Y^{22}$ may also independent of their respective occurrence form together with the nitrogen atom to which they are bonded a 4-, 5- or 6-membered, saturated or wholly or partly unsaturated N-heterocyclic ring, the tautomeric, enantiomeric and diastereomeric forms thereof, and the prodrugs thereof, and the physiologically tolerated salts of said compounds.

$R_A^4$ is in particular selected from the group consisting of $NH_2$, $NH(C_1-C_4$-alkyl), $N(C_1-C_4$-alkyl)$(C_1-C_4$-alkyl), $N(C_1-C_4$-alkyl)$(C_1-C_4$-alkylene-O-$C_1-C_4$-alkyl), $NH-CHO$, $NH-CO-NH_2$, $NH-CO-C_1-C_4$-alkyl and ring $R_A^8$.

A preferred embodiment relates to compounds of the general formula (I) in which the variables have independently of one another the following meanings:

A is an aromatic or heteroaromatic monocyclic radical having 2, 3, 4, 5, 6, 7, 8, 9 or 10 carbon atoms as ring members, which may besides comprise additionally 0, 1, 2 or 3 identical or different heteroatoms independently of one another selected from the group consisting of nitrogen, oxygen and sulfur, as ring members, and is substituted by the radical $R_A^1$ and may besides be substituted by one, two or three radicals $R_A^{11}$, $R_A^{12}$ and/or $R_A^{13}$ which are selected independently of one another and independent of their respective occurrence from the group consisting of hydrogen, chlorine, fluorine, $O-C_1-C_4$-alkyl, $C_1-C_4$-alkyl and $C_1-C_4$-haloalkyl, in which $R_A^1$ is $R_A^2-(C_1-C_4$-alkylene)-$R_A^4$;

$R_A^2$ is selected from the group consisting of $(C_0-C_4$-alkylene)-O, $(C_0-C_4$-alkylene)-$NR_A^5$, $(C_0-C_4$-alkylene)-S, $(C_0-C_4$-alkylene)-SO, $(C_0-C_4$-alkylene)-$SO_2$, $(C_0-C_4$-alkylene)-CO, $(C_0-C_4$-alkylene)-$NR_A^5$—CO, $(C_0-C_4$-alkylene)-CO—$NR_A^5$, $(C_0-C_4$-alkylene)-CO—O and single bond;

$R_A^4$ is selected from the group consisting of $NH_2$, $NH(C_1-C_4$-alkyl), $N(C_1-C_4$-alkyl)$(C_1-C_4$-alkyl), $N(C_1-C_4$-alkyl)$(C_1-C_4$-alkylene-O-$C_1-C_4$-alkyl) and ring $R_A^8$;

$R_A^5$, $R_A^9$ are selected independently of one another and independent of their respective occurrence from the group consisting of hydrogen and $C_1-C_4$-alkyl;

$R_A^8$ is selected independent of its respective occurrence from the group consisting of the respective individual radicals

[chemical structures: azetidine, pyrrolidine, pyrroline, piperidine, tetrahydropyridine, azepane, morpholine, thiomorpholine, piperazine-NH, piperazine-N—$R_A^9$, piperazine-N—CO—$R_A^9$]

B is an aromatic or heteroaromatic mono- or bicyclic radical having 2, 3, 4, 5, 6, 7, 8, 9 or 10 C atoms as ring members, which may additionally comprise 1, 2 or 3 identical or different heteroatoms selected independently of one another from the group consisting of nitrogen, oxygen and sulfur as ring members, and which may be substituted by one, two or three radicals $R_B^1$, $R_B^2$ and/or $R_B^3$, where $R_B^1$, $R_B^2$ and $R_B^3$ are selected independently of one another and independent of their respective occurrence from the group consisting of hydrogen, chlorine, bromine, fluorine, CN, $CF_3$, $OCF_3$, $OCHF_2$, O—$C_1$-$C_4$-alkyl, $C_1$-$C_4$-alkyl and $C_1$-$C_4$-haloalkyl;

$R^1$ is selected from the group consisting of hydrogen, bromine, chlorine, fluorine, CN, $CF_3$, $OCF_3$, O—$C_1$-$C_4$-alkyl, $C_1$-$C_4$-alkyl, $C_1$-$C_4$-haloalkyl and $C_2$-$C_4$-alkynyl, $R^2$ is selected from the group consisting of hydrogen, $C_1$-$C_4$-alkyl, $C_1$-$C_4$-halo-alkyl, O—$C_1$-$C_4$-alkyl, chlorine and fluorine, Y is a radical

[structure: $R_Y^1$—N(*)—C($R_Y^2$)($R_Y^3$)—$R_Y^4$]

in which $R_Y^1$ is selected from the group consisting of hydrogen and $C_1$-$C_4$-alkyl;

$R_Y^2$ is selected from the group consisting of hydrogen, phenyl, $C_1$-$C_6$-alkyl, and $C_3$-$C_7$-cycloalkyl in which $R_Y^1$ and $R_Y^2$ may also form together with the atoms to which they are bonded a 4-, 5-, 6- or 7-membered, saturated or unsaturated ring which may, instead of a C atom as ring member, also include a hetero-atom selected from the group consisting of O and $NR_Y^5$, as further ring member, where $R_Y^5$ may independent of its respective occurrence be hydrogen, $C_1$-$C_4$-alkyl, $C_1$-$C_4$-haloalkyl or CO—$C_1$-$C_4$-alkyl, and where the ring may have one or two substituents $R_Y^6$ and/or $R_Y^7$ which are selected independently of one another and independent of their respective occurrence from the group consisting of the radicals hydrogen, fluorine, CN, OH, O—$C_1$-$C_4$-alkyl, O—CO—$C_1$-$C_4$-alkyl, O—$(CH_2)_{0-2}$-phenyl, phenyl and $C_1$-$C_4$-alkyl;

or $R_Y^6$ and $R_Y^7$ may independent of their respective occurrence also form together with the C atoms to which they are bonded a fused phenyl ring (benzo ring);

$R_Y^3$ is selected from the group consisting of hydrogen and methyl, $R_Y^4$ is selected from the group consisting of CO—$NR_Y^{21}R_Y^{22}$, CO—$C_1$-$C_4$-alkyl and CO—O—$C_1$-$C_4$-alkyl, $R_Y^{21}$, $R_Y^{22}$ are selected independently of one another and independent of their respective occurrence from the group consisting of hydrogen and $C_1$-$C_4$-alkyl;

or $R_Y^{21}$ and $R_Y^{22}$ may independent of their respective occurrence also form together with the nitrogen atom to which they are bonded a 4-, 5- or 6-membered, saturated or unsaturated N-heterocyclic ring, the tautomeric, enantiomeric and diastereomeric forms thereof, and the prodrugs thereof, and the physiologically tolerated salts of said compounds.

A further preferred embodiment relates to compounds of the general formula (I) in which the variables have independently of one another the following meanings:

A is a cyclic radical which is selected from the group consisting of phenyl, thienyl, pyridyl, pyrimidinyl, pyrazinyl and pyridazinyl, and which is substituted by the radical $R_A^1$ and may besides be additionally substituted by one or two radicals $R_A^{11}$ and/or $R_A^{12}$ which are selected independently of one another and independent of their respective occurrence from the group consisting of hydrogen, chlorine, methoxy, ethoxy, propoxy, methyl, ethyl and propyl;

in which $R_A^1$ is $R_A^2$—($C_1$-$C_4$-alkylene)-$R_A^4$, in which $R_A^2$ is selected from the group consisting of O, $CH_2$—O, $NR_A^5$, $CH_2$—$NR_A^5$, $NR_A^5$—CO, $CH_2$—$NR_A^5$—CO and a single bond;

$R_A^4$ is selected from the group consisting of $NH_2$, NH($C_1$-$C_4$-alkyl), N($C_1$-$C_4$-alkyl)($C_1$-$C_4$-alkyl), N($C_1$-$C_4$-alkyl)($C_1$-$C_4$-alkylene-O—$C_1$-$C_4$-alkyl) and ring $R_A^8$;

$R_A^5$, $R_A^9$ are selected independently of one another and independent of their respective occurrence from the group consisting of hydrogen and $C_1$-$C_4$-alkyl;

$R_A^8$ is selected from the group consisting of the respective individual radicals

[chemical structures: pyrrolidine, pyrroline, piperidine, tetrahydropyridine, morpholine, piperazine-NH, piperazine-N—$R_A^9$, piperazine-N—CO—$R_A^9$]

B is an aromatic or heteroaromatic mono- or bicyclic radical having 2, 3, 4, 5, 6, 7, 8, 9 or 10 C atoms as ring members, which may comprise 1, 2 or 3 identical or different heteroatoms selected independently of one another from the group consisting of nitrogen, oxygen and sulfur as ring member, and which may be substituted by one or two radicals $R_B^1$ and/or $R_B^2$, where $R_B^1$ and $R_B^2$ are selected independently of one another from the group consisting of hydrogen, chlorine, fluorine, CN, O—$C_1$-$C_4$-alkyl and $C_1$-$C_4$-alkyl;

$R^1$ is selected from the group consisting of hydrogen, chlorine, fluorine, CN, methoxy and methyl;

$R^2$ is selected from the group consisting of hydrogen, chlorine and methyl;

Y is a radical

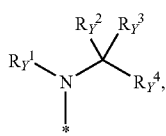

in which
$R_Y^1$ is selected from the group consisting of hydrogen and $C_1$-$C_4$-alkyl;

$R_Y^2$ is selected from the group consisting of hydrogen, phenyl and $C_1$-$C_4$-alkyl;

where $R_Y^1$ and $R_Y^2$ may also form together with the atoms to which they are bonded a 5- or 6-membered, saturated or unsaturated ring which, instead of a C atom as ring member, may also include a heteroatom selected from the group consisting of O and $NR_Y^5$ as further ring member, where $R_Y^5$ may independent of its respective occurrence be hydrogen, $C_1$-$C_4$-alkyl, or CO—$C_1$-$C_4$-alkyl, and where the ring may have one or two substituents $R_Y^6$ and/or $R_Y^7$ which are selected independently of one another and independent of their respective occurrence from the group consisting of the radicals hydrogen, fluorine, OH and O—$C_1$-$C_4$-alkyl, or $R_Y^6$ and $R_Y^7$ may independent of their respective occurrence also form together with the C atoms to which they are bonded a fused phenyl ring (benzo ring);

$R_Y^3$ is selected from the group consisting of hydrogen and methyl;

$R_Y^4$ is CO—$NR_Y^{21}R_Y^{22}$, in which $R_Y^{21}$, $R_Y^{22}$ are selected independently of one another from the group consisting of hydrogen and $C_1$-$C_4$-alkyl;

or $R_Y^{21}$ and $R_Y^{22}$ may independent of their respective occurrence also form together with the nitrogen atom to which they are bonded a 4-, 5- or 6-membered, saturated or unsaturated N-heterocyclic ring;

the tautomeric, enantiomeric and diastereomeric forms thereof, and the prodrugs thereof, and the physiologically tolerated salts of said compounds.

A further preferred embodiment relates to compounds of the general formula (I) in which the variables have independently of one another the following meanings:

A is a radical selected from the group consisting of the respective individual radicals

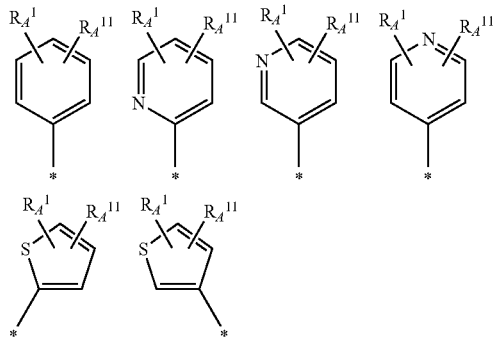

in which
$R_A^{11}$ is selected independent of its respective occurrence from the group consisting of hydrogen, chlorine, methoxy and ethoxy;

$R_A^1$ is a radical selected from the group consisting of the respective individual radicals

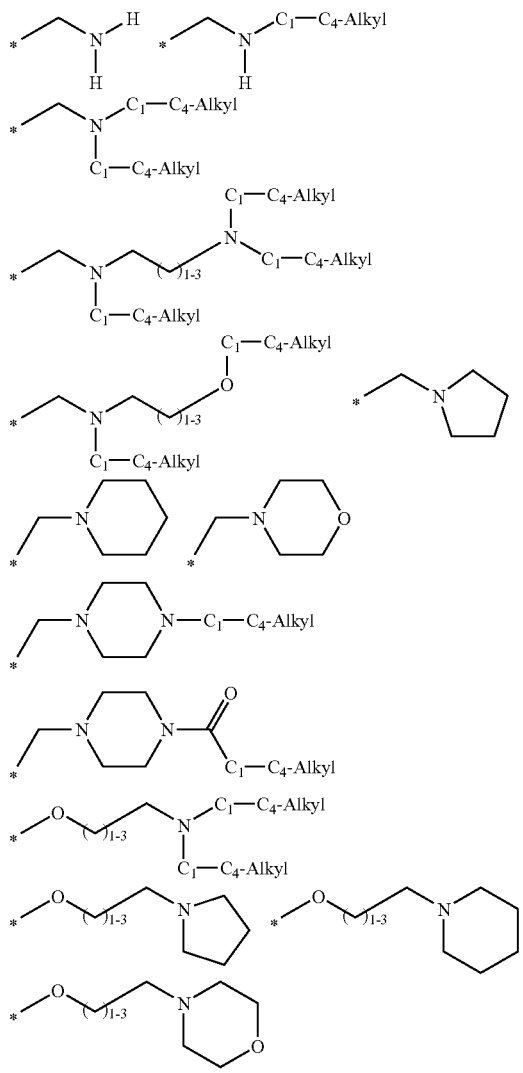

-continued

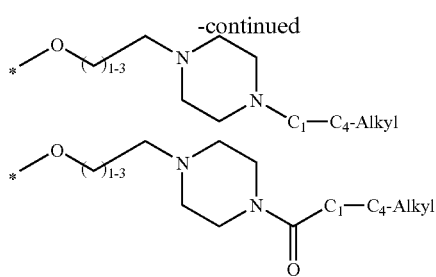

B is a cyclic radical selected from the group consisting of phenyl, pyridyl, thienyl and quinolinyl, which may in each case be substituted by 1 or 2 radicals $R_B^1$ and/or $R_B^2$, where $R_B^1$ and $R_B^2$ are selected independently of one another from the group consisting of hydrogen, chlorine, fluorine, CN, methyl and methoxy;

$R^1$ is selected from the group consisting of hydrogen, chlorine, fluorine, CN, methoxy and methyl;

$R^2$ is selected from the group consisting of hydrogen and chlorine;

Y is a radical selected from the group consisting of the respective individual radicals

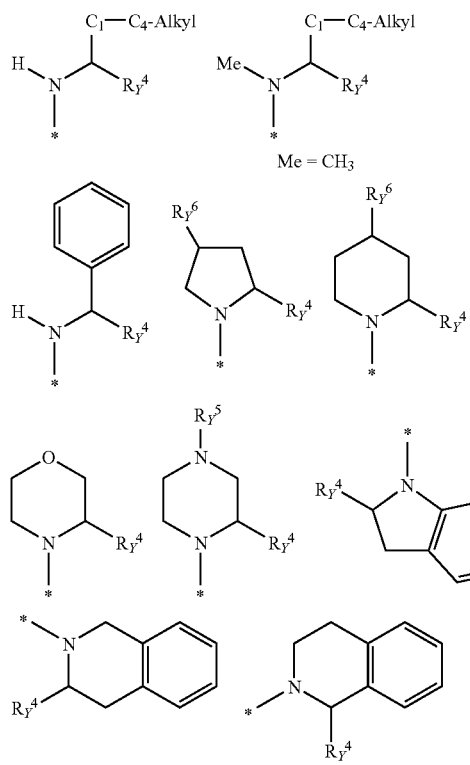

$R_Y^4$ is CO—$NR_Y^{21}R_Y^{22}$, where $R_Y^{21}$ and $R_Y^{22}$ are selected independently of one another from the group consisting of hydrogen, methyl and ethyl;
or
$R_Y^{21}$ and $R_Y^{22}$ may independent of their respective occurrence also form together with the nitrogen atom to which they are bonded a 4-, 5- or 6-membered, saturated or unsaturated or partly unsaturated N-heterocyclic ring;

$R_Y^5$ is selected from the group consisting of the radicals hydrogen, $C_1$-$C_4$-alkyl, and CO—$C_1$-$C_4$-alkyl;

$R_Y^6$ is selected from the group consisting of the radicals hydrogen, fluorine, OH and O—$C_1$-$C_4$-alkyl, the tautomeric, enantiomeric and diastereomeric forms thereof, and the prodrugs thereof, and the physiologically tolerated salts of said compounds.

A further preferred embodiment relates to compounds of the general formula (I) in which the variables have independently of one another the following meanings:

A is phenyl which, besides the radical $R_A^1$, may carry a further radical $R_A^{11}$ which is selected from Cl and $C_1$-$C_4$-alkoxy and which is preferably linked in the position ortho to the point of linkage of the phenyl ring to the remainder of the molecule, e.g. a radical selected from the group consisting of the respective individual radicals

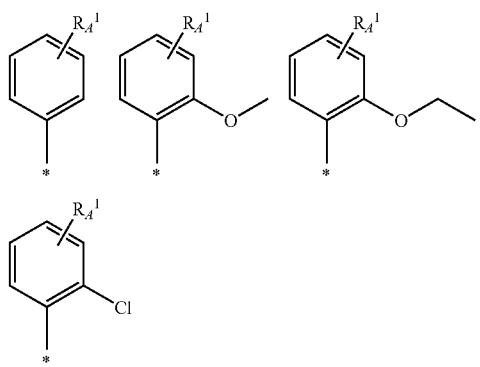

$R_A^1$ is a radical selected independent of its respective occurrence from the group consisting of the respective individual radicals

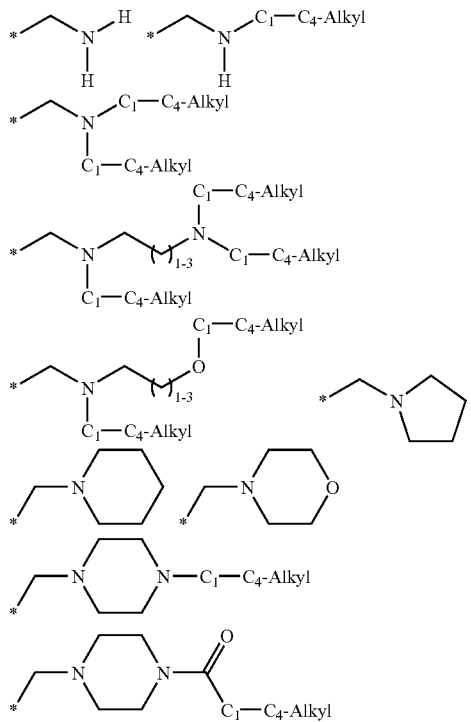

-continued

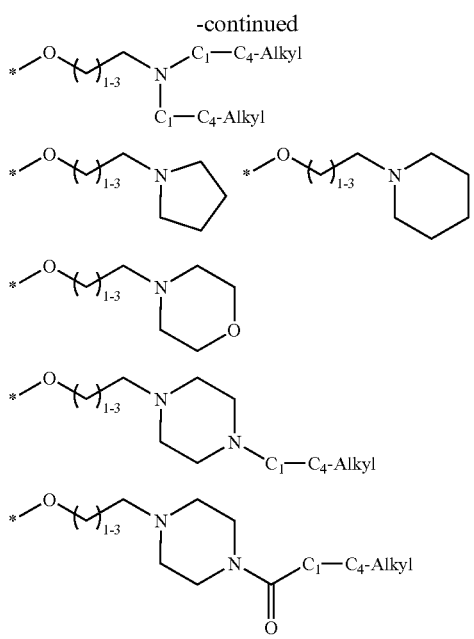

B is a cyclic radical selected from the group of phenyl, pyridyl, thienyl and quinolinyl, each of which may carry one or two radicals $R_B^1$, $R_B^2$ where B is in particular one of the radicals:

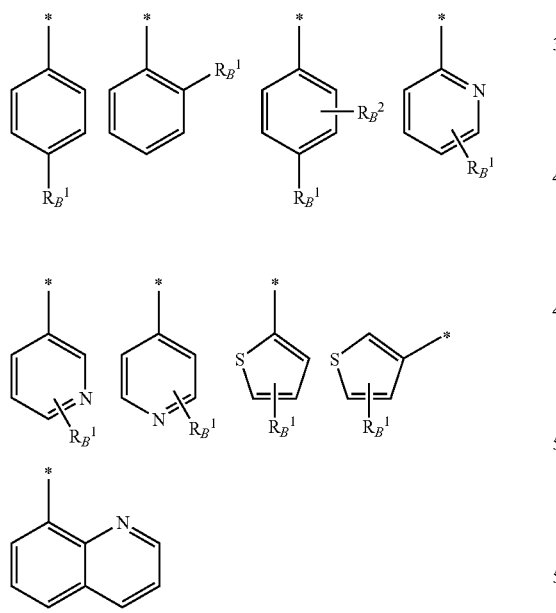

in which
$R_B^1$ and $R_B^2$ are selected independently of one another and independent of their respective occurrence from the group consisting of hydrogen, chlorine, fluorine, CN, methyl and methoxy;
$R^1$ is selected from the group consisting of chlorine, methoxy and CN;
$R^2$ is hydrogen;
Y is selected from the group consisting of the respective individual radicals

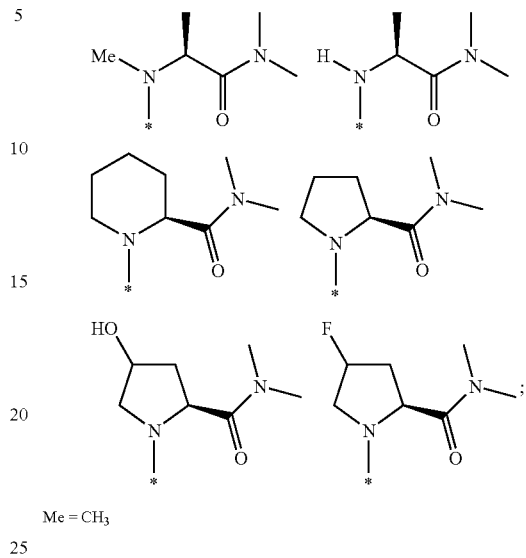

Me = CH$_3$ the tautomeric, enantiomeric and diastereomeric forms thereof, and the prodrugs thereof, and the physiologically tolerated salts of said compounds.

A further preferred embodiment relates to compounds of the general formula (I) in which the variables have independently of one another the following meanings:

A is selected from the group consisting of the respective individual radicals

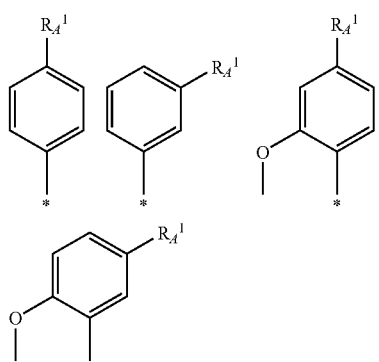

in which
$R_A^1$ is a radical selected independent of its respective occurrence from the group consisting of the respective individual radicals

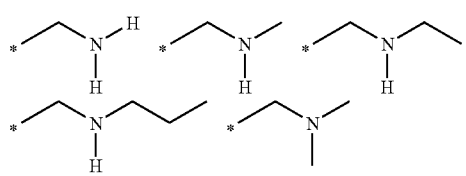

-continued

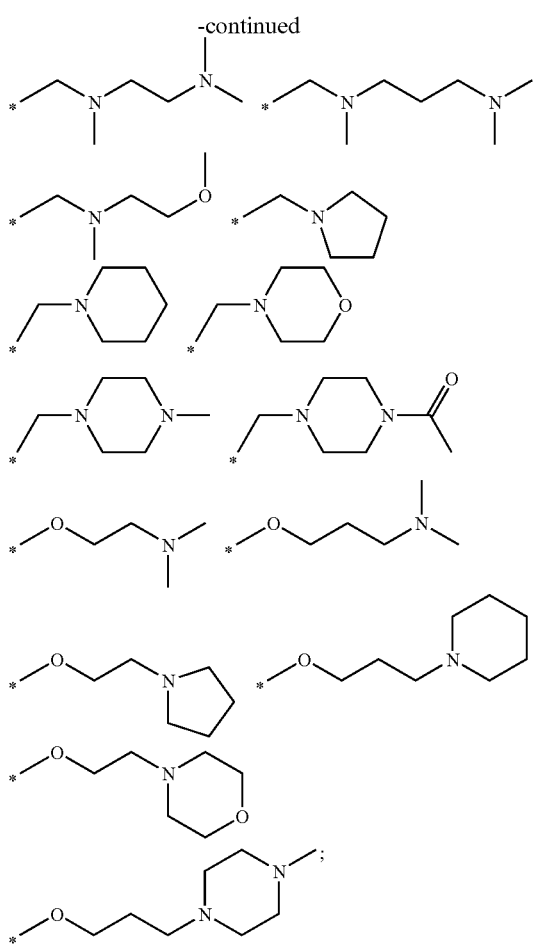

B is a cyclic radical selected from the group consisting of the respective individual radicals

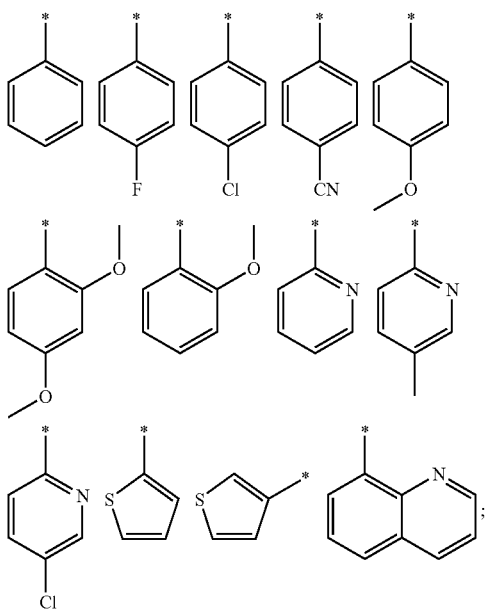

R¹ is chlorine;
R² is hydrogen;
Y is a radical selected from the group consisting of the respective individual radicals

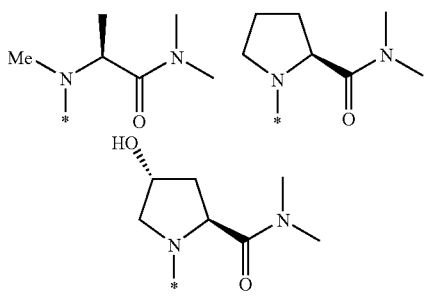

Me = CH₃ the tautomeric, enantiomeric and diastereomeric forms thereof, and the prodrugs thereof, and the physiologically tolerated salts of said compounds.

A further preferred embodiment relates to compounds of the general formula (I) in which the variables have independently of one another the following meanings:

A is a radical selected from the group consisting of the respective individual radicals

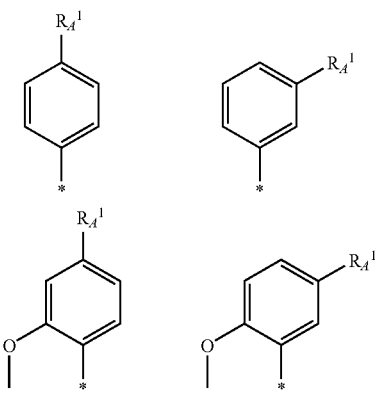

$R_A^1$ is a radical selected independent of its respective occurrence from the group consisting of the respective individual radicals

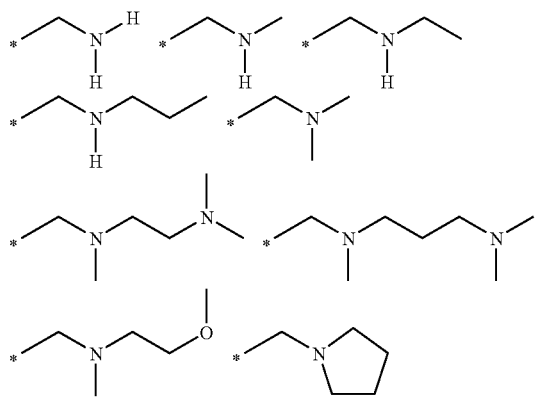

-continued

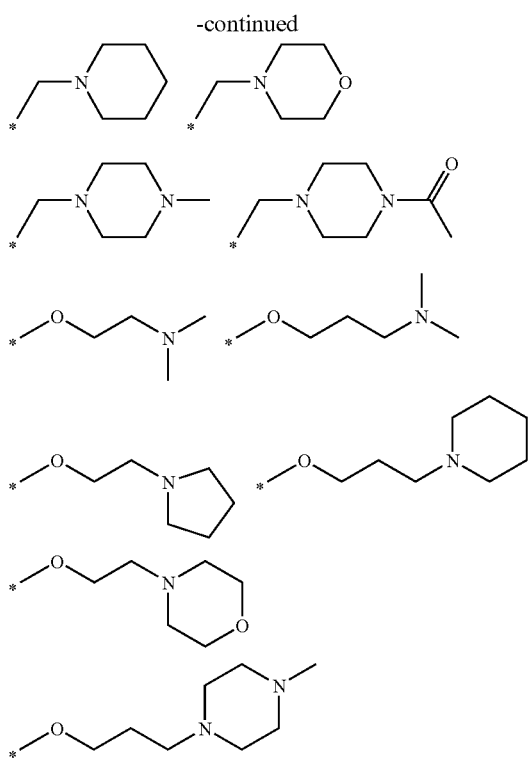

B is a cyclic radical selected from the group consisting of the respective individual radicals

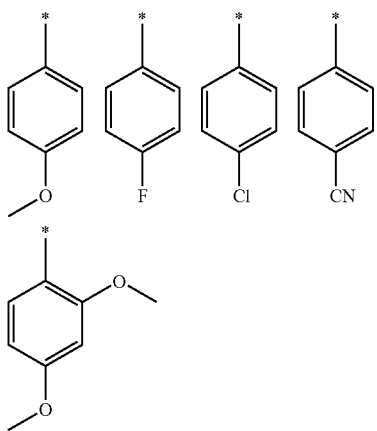

$R^1$ is chlorine;
$R^2$ is hydrogen;
Y is a radical selected from the group consisting of the respective individual radicals

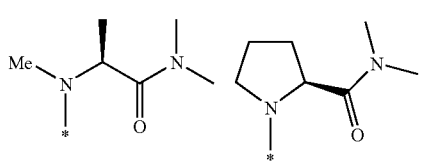

-continued

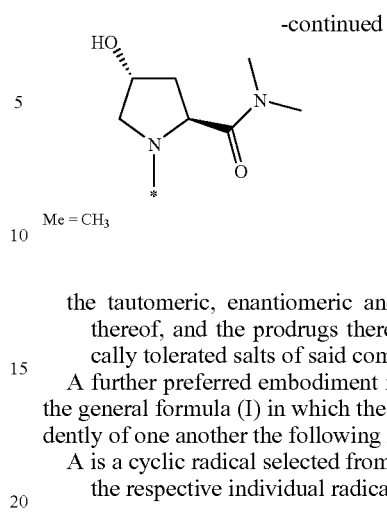

Me = CH$_3$ the tautomeric, enantiomeric and diastereomeric forms thereof, and the prodrugs thereof, and the physiologically tolerated salts of said compounds.

A further preferred embodiment relates to compounds of the general formula (I) in which the variables have independently of one another the following meanings:

A is a cyclic radical selected from the group consisting of the respective individual radicals

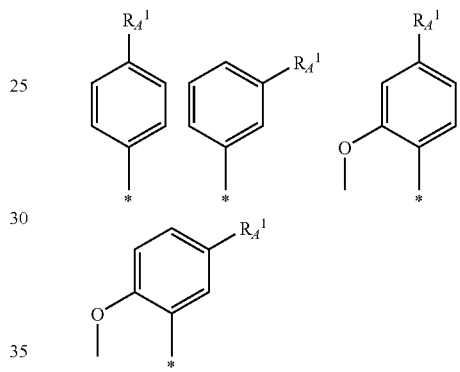

in which
$R_A^1$ is a radical selected from the group consisting of the respective individual radicals

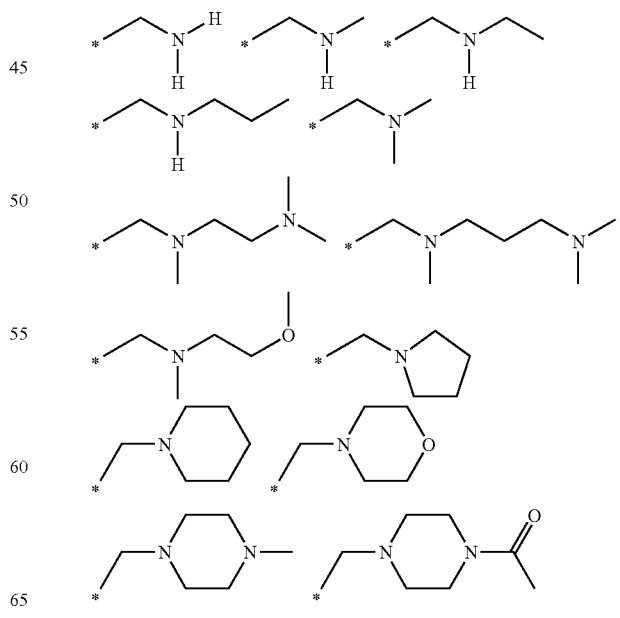

B is a cyclic radical selected from the group consisting of the respective individual radicals

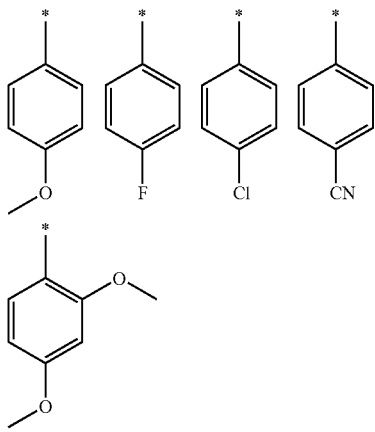

R¹ is chlorine,
R² is hydrogen,
Y is selected from the group consisting of the respective individual radicals

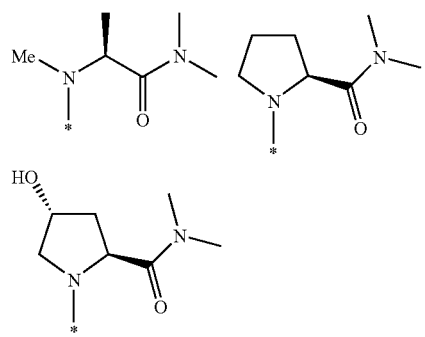

Me = CH₃ the tautomeric, enantiomeric and diastereomeric forms thereof, and the prodrugs thereof, and the physiologically tolerated salts of said compounds.

A further preferred embodiment relates to compounds of the general formula (I) in which the radical R¹ is linked at position 5 of the oxindole ring structure.

A further preferred embodiment relates to compounds of the general formula (I) where the compound of the general formula (I) is an enriched optically active isomer having an optical purity greater than 50% based on the optically inactive mixture of the isomeric mixture which rotates the plane of polarized light to the left ("negative rotation").

A further preferred embodiment relates to compounds of the general formula (I) where the optically active isomer is an enantiomerically enriched diastereomer.

A further preferred embodiment relates to compound of the general formula (I) in which the property of "negative rotation" relates to the free base.

A further preferred embodiment relates to compounds of the general formula (I) which have a binding affinity Ki for the vasopressin V1b receptor subtype of less than about 100 nM, preferably not more than 10 nM, in particular not more than 1 nM and specifically not more than 0.1 nM, e.g. 0.01 to less than 100 nM, or 0.1 to less than 100 nM or 1 to less than 100 nM or 10 to less than 100 nM or 0.01 to 10 nM, or 0.1 to 10 nM or 1 to 10 nM.

A further preferred embodiment relates to compounds of the general formula (I) which have a selectivity for the vasopressin V1b receptor subtype vis-à-vis the vasopressin V1a receptor subtype, where the quotient of Ki(V1a)/Ki(V1b) is greater than 1.

A further preferred embodiment relates to compounds of the general formula (I) which have a selectivity for the vasopressin V1b receptor subtype vis-à-vis the vasopressin V2 receptor subtype, where the quotient of Ki(V2)/Ki(V1b) is greater than 1.

A further preferred embodiment relates to compounds of the general formula (I) which have a selectivity for the vasopressin V1b receptor subtype vis-à-vis the oxytocin (OT) receptor, where the quotient of Ki(OT)/Ki(V1 b) is greater than 1.

A further preferred embodiment relates to compounds of the general formula (I) which have a binding affinity Ki for the vasopressin V1b receptor subtype of less than 100 nM, preferably not more than 10 nM, in particular not more than 1 nM and specifically not more than 0.1 nM, e.g. 0.01 to less than 100 nM, or 0.1 to less than 100 nM or 1 to less than 100 nM or 10 to less than 100 nM or 0.01 to 10 nM, or 0.1 to 10 nM or 1 to 10 nM, and a selectivity for the vasopressin V1b receptor subtype vis-à-vis the vasopressin V1a receptor subtype, where the quotient of Ki(V1a)/Ki(V1b) is greater than 1.

A further preferred embodiment relates to compounds of the general formula (I) which have a binding affinity Ki for the vasopressin V1b receptor subtype of less than 100 nM, preferably not more than 10 nM, in particular not more than 1 nM and specifically not more than 0.1 nM, e.g. 0.01 to less than 100 nM, or 0.1 to less than 100 nM or 1 to less than 100 nM or 10 to less than 100 nM or 0.01 to 10 nM, or 0.1 to 10 nM or 1 to 10 nM, and a selectivity for the vasopressin V1b receptor subtype vis-à-vis the vasopressin V2 receptor subtype, where the quotient of Ki(V2)/Ki(V1 b) is greater than 1.

A further preferred embodiment relates to compounds of the general formula (I) which have a binding affinity Ki for the vasopressin V1b receptor subtype of less than 100 nM, preferably not more than 10 nM, in particular not more than 1 nM and specifically not more than 0.1 nM, e.g. 0.01 to less than 100 nM, or 0.1 to less than 100 nM or 1 to less than 100 nM or 10 to less than 100 nM or 0.01 to 10 nM, or 0.1 to 10 nM or 1 to 10 nM, and a selectivity for the vasopressin V1b receptor subtype vis-à-vis the oxytocin (OT) receptor, where the quotient of Ki(OT)/Ki(V1b) is greater than 1.

A further preferred embodiment relates to compounds of the general formula (I) which have a binding affinity Ki for the vasopressin V1b receptor subtype of less than 100 nM, preferably not more than 10 nM, in particular not more than 1 nM and specifically not more than 0.1 nM, e.g. 0.01 to less than 100 nM, or 0.1 to less than 100 nM or 1 to less than 100 nM or 10 to less than 100 nM or 0.01 to 10 nM, or 0.1 to 10 nM or 1 to 10 nM, and selectivities for the vasopressin V1b receptor subtype vis-à-vis the vasopressin V1a receptor subtype and the vasopressin V2 receptor subtype, where the quotients of Ki(V1a)/Ki(V1b) and Ki(V2)/Ki(V1b) are in each case greater than 1.

A further preferred embodiment relates to compounds of the general formula (I) which have a binding affinity Ki for the vasopressin V1b receptor subtype of less than 100 nM, preferably not more than 10 nM, in particular not more than 1 nM and specifically not more than 0.1 nM, e.g. 0.01 to less than 100 nM, or 0.1 to less than 100 nM or 1 to less than 100 nM or 10 to less than 100 nM or 0.01 to 10 nM, or 0.1 to 10 nM or 1 to 10 nM, and simultaneous selectivities for the vasopressin V1b receptor subtype vis-à-vis the vasopressin V1a receptor subtype and the oxytocin (OT) receptor, where the quotients of Ki(V1a)/Ki(V1b) and Ki(OT)/Ki(V1b) are in each case greater than 1.

A further preferred embodiment relates to compounds of the general formula (I) which have a binding affinity Ki for the vasopressin V1b receptor subtype of less than 100 nM, preferably not more than 10 nM, in particular not more than 1 nM and specifically not more than 0.1 nM, e.g. 0.01 to less than 100 nM, or 0.1 to less than 100 nM or 1 to less than 100 nM or 10 to less than 100 nM or 0.01 to 10 nM, or 0.1 to 10 nM or 1 to 10 nM, and simultaneous selectivities for the vasopressin V1b receptor subtype vis-à-vis the vasopressin V2 receptor subtype and the oxytocin (OT) receptor, where the quotients of Ki(V2)/Ki(V1b) and Ki(OT)/Ki(V1b) are in each case greater than 1.

A further preferred embodiment relates to compounds of the general formula (I) which have a binding affinity Ki for the vasopressin V1b receptor subtype of less than 100 nM, preferably not more than 10 nM, in particular not more than 1 nM and specifically not more than 0.1 nM, e.g. 0.01 to less than 100 nM, or 0.1 to less than 100 nM or 1 to less than 100 nM or 10 to less than 100 nM or 0.01 to 10 nM, or 0.1 to 10 nM or 1 to 10 nM, and simultaneous selectivities for the vasopressin V1b receptor subtype vis-à-vis the vasopressin V1a receptor subtype, the vasopressin V2 receptor subtype and the oxytocin (OT) receptor, where the quotients of Ki(V1a)/Ki(V1b), Ki(V2)/Ki(V1b) and Ki(OT)/Ki(V1b) are in each case greater than 1.

A further aspect of the present invention relates to compounds of the general formula (I) for use as medicament.

A further aspect of the present invention relates to a medicament comprising at least one compound of the general formula (I).

A further aspect of the present invention relates to the use of at least one compound of the general formula (I) for the treatment and/or prophylaxis of at least one vasopressin-dependent and/or oxytocin-dependent disease and/or for the manufacture of a medicament for the treatment and/or prophylaxis of at least one of said diseases.

A further aspect of the present invention relates to the use of at least one compound of the general formula (I) for the treatment and/or prophylaxis of at least one disorder selected from the group consisting of diabetes insipidus, nocturnal enuresis, incontinence, diseases in which blood coagulation disorders occur, and/or for delaying micturition and/or for the manufacture of a medicament for the treatment and/or prophylaxis of at least one of said diseases.

A further aspect of the present invention relates to the use of at least one compound of the general formula (I) for the treatment and/or prophylaxis of at least one disorder selected from the group consisting of hypertension, pulmonary hypertension, heart failure, myocardial infarction, coronary spasm, unstable angina, PTCA (percutaneous transluminal coronary angioplastie), ischemias of the heart, disorders of the renal system, edemas, renal vasospasm, necrosis of the renal cortex, hyponatremia, hypokalemia, Schwartz-Bartter syndrome, disorders of the gastrointestinal tract, gastritic vasospasm, hepatocirrhosis, gastric and intestinal ulcer, emesis, emesis occurring during chemotherapy, and/or travel sickness and/or for the manufacture of a medicament for the treatment and/or prophylaxis of at least one of said diseases.

A further aspect of the present invention relates to the use of at least one compound of the general formula (I) for the treatment and/or prophylaxis of affective disorders and/or for the manufacture of a medicament for the treatment of affective disorders.

A further aspect of the present invention relates to the use of at least one compound of the general formula (I) for the treatment and/or prophylaxis of anxiety disorders and/or stress-dependent anxiety disorders and/or for the manufacture of a medicament for the treatment of anxiety disorders and/or stress-dependent anxiety disorders.

A further aspect of the present invention relates to the use of at least one compound of the general formula (I) for the treatment and/or prophylaxis of memory impairments and/or Alzheimer's disease and/or for the manufacture of a medicament for the treatment and/or prophylaxis of memory impairments and/or Alzheimer's disease.

A further aspect of the present invention relates to the use of at least one compound of the general formula (I) for the treatment and/or prophylaxis of psychoses and/or psychotic disorders and/or for the manufacture of a medicament for the treatment and/or prophylaxis of psychoses and/or psychotic disorders.

A further aspect of the present invention relates to the use of at least one compound of the general formula (I) for the treatment and/or prophylaxis of Cushing's syndrome and/or for the manufacture of a medicament for the treatment and/or prophylaxis of Cushing's syndrome.

A further aspect of the present invention relates to the use of at least one compound of the general formula (I) for the treatment and/or prophylaxis of sleep disorders and/or for the manufacture of a medicament for the treatment and/or prophylaxis of sleep disorders.

A further aspect of the present invention relates to the use of at least one compound of the general formula (I) for the treatment and/or prophylaxis of depressive disorders and/or for the manufacture of a medicament for the treatment and/or prophylaxis of depressive disorders.

A further aspect of the present invention relates to a method for the treatment and/or prophylaxis of at least one disorder selected from the group consisting of diabetes insipidus, nocturnal enuresis, incontinence, diseases in which blood coagulation disorders occur, and for delaying micturition in a patient, where an effective amount of at least one compound of the general formula (I) is administered to the patient.

A further aspect of the present invention relates to a method for the treatment and/or prophylaxis of at least one disorder selected from the group consisting of hypertension, pulmonary hypertension, heart failure, myocardial infarction, coronary spasm, unstable angina, PTCA (percutaneous transluminal coronary angioplastie), ischemias of the heart, disorders of the renal system, edemas, renal vasospasm, necrosis of the renal cortex, hyponatremia, hypokalemia, Schwartz-Bartter syndrome, disorders of the gastrointestinal tract, gastritic vasospasm, hepatocirrhosis, gastric and intestinal ulcer, emesis, emesis occurring during chemotherapy, and travel sickness in a patient, where an effective amount of at least one compound of the general formula (I) is administered to the patient.

A further aspect of the present invention relates to a method for the treatment and/or prophylaxis of affective disorders in a patient, where an effective amount of at least one compound of the general formula (I) is administered to the patient.

A further aspect of the present invention relates to a method for the treatment of anxiety disorders and/or stress-dependent anxiety disorders in a patient, where an effective amount of at least one compound of the general formula (I) is administered to the patient.

A further aspect of the present invention relates to a method for the treatment of memory impairments and/or Alzheimer's disease in a patient, where an effective amount of at least one compound of the general formula (I) is administered to the patient.

A further aspect of the present invention relates to a method for the treatment of psychoses and/or psychotic disorders in a patient, where an effective amount of at least one compound of the general formula (I) is administered to the patient.

A further aspect of the present invention relates to a method for the treatment of Cushing's syndrome in a patient, characterized in that an effective amount of at least one compound of the general formula (I) is administered to the patient.

A further aspect of the present invention relates to a method for the treatment of sleep disorders in a patient, where an effective amount of at least one compound of the general formula (I) is administered to the patient.

A further aspect of the present invention relates to a method for the treatment of depressive disorders in a patient, where an effective amount of at least one compound of the general formula (I) is administered to the patient.

A further aspect of the present invention relates to a method for the treatment and/or prophylaxis of vasomotor disorders in a patient, where an effective amount of at least one compound of the general formula (I) is administered to the patient.

A further aspect of the present invention relates to a method for the treatment and/or prophylaxis of disorders associated with drug withdrawal in a patient, where an effective amount of at least one compound of the general formula (I) is administered to the patient.

In a preferred embodiment, the methods described above are characterized by the patient being a mammal, preferably a human or a non-human or a non-human transgenic mammal.

A further aspect of the present invention relates to a method for preparing compounds of the general formula (I), where the compounds of the general formula (I) can be prepared by carrying out and/or carrying out analogously method steps known per se to the relevant skilled worker.

Each of these preferred definitions of a variable can be combined with any of the definitions of the remaining variables.

A further embodiment provides at least one compound of the invention with the general formula (I) selected from the group consisting of the examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101 and 102, and the tautomeric, enantiomeric and diastereomeric forms thereof, and the prodrugs thereof, and non-salt forms and other physiologically tolerated salts of the aforementioned compounds.

The compounds of the invention may be in the form of a mixture of diastereomers, a mixture of diastereomers in which one of the two diastereomers is enriched, or of diastereomerically pure compounds (de>90%). The compounds are preferably in the form of diastereomerically pure compounds. The respective diastereomers may in turn be in the form of a mixture of enantiomers (for example as racemate), of a mixture of enantiomers in which one of the two enantiomers is enriched, or of enantiomerically pure compounds (ee>90%). The respective diastereomers are preferably in the form of enantiomerically pure compounds. Compounds which are diastereomerically pure and enantiomerically pure (de>90%, ee>90%) are particularly preferred.

Physiologically tolerated salts in the sense of the description may, unless stated otherwise, be formed for example with the following anions:

chloride, bromide, phosphate, carbonate, nitrate, perchlorate, sulfate, citrate, lactate, tartrate, maleate, fumarate, mandelate, benzoate, ascorbate, cinnamate, glycolate, methanesulfonate, formate, malonate, naphthalene-2-sulfonate, tosylates, salicylate, trifluoroacetate and/or acetate. Further suitable acid are listed for example in "Fortschritte der Arzneimittelforschung", 1966, Birkhäuser Verlag, Vol. 10, pp. 224-285.

In the sense of the present description, unless stated otherwise, the terms "alkyl", "cycloalkyl", "alkoxy", "haloalkyl" "alkenyl", "alkynyl" or "alkylene", and radicals derived therefrom, always comprise both unbranched and branched "alkyl", "cycloalkyl", "alkoxy", "haloalkyl", "alkenyl", "alkynyl" or "alkylene".

$C_0$-alkylene or $(CH_2)_0$ or similar expressions designate in the sense of the description, unless stated otherwise, a single bond or hydrogen.

The terms $C_1$-$C_6$-alkyl and $C_1$-$C_4$-alkyl mean in the sense of the description, unless stated otherwise, a straight-chain or branched saturated hydrocarbon chain with the number indicated in each case of carbon atoms respectively from 1 to 6 and from 1 to 4 carbon atoms such as, for example, methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, n-hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl or 1-ethyl-2-methylpropyl, preferably methyl, ethyl, propyl, n-butyl or i-butyl. $C_1$-$C_4$-alkyl is in the sense of the description, unless stated otherwise, preferably methyl, ethyl, n-propyl, i-propyl, n-butyl, sec-butyl or t-butyl.

The term "$C_1$-$C_6$-alkoxy" means in the sense of the description, unless stated otherwise, a $C_1$-$C_6$-alkyl group which is as defined above and is linked via oxygen.

The terms $C_1$-$C_6$-alkylene and $C_0$-$C_4$-alkylene (with $C_0$-alkylene=single bond) mean in the sense of the description, unless stated otherwise, an alkyl group which has respectively 1 to 6 and 0 to 4 C atoms, which is defined as previously and in which one hydrogen atom is replaced by a bond. Examples which should be particularly mentioned are methylene, eth-1,2-ylene, prop-1,2-ylene, prop-1,3-ylene, but-1,2-ylene, but-1,3-ylene, but-2,3-ylene, but-1,4-ylene, 2-methylprop-1,3-ylene, pent-1,2-ylene, pent-1,3-ylene, pent-1,4-ylene, pent-1,5-ylene, pent-2,3-ylene, pent-2,4-ylene, 1-methylbut-1,4-ylene, 2-methylbut-1,4-ylene, 2-methylbut-1,3-ylene, 2-ethylprop-1,3-ylene, hex-3,4-ylene, 3-methylpent-2,4-ylene, hept-3,5-ylene, 2-ethylpent-1,3-ylene, 3-ethylhept-3,5-ylene, etc., preferably methylene, eth-1,2-ylene and prop-1,2-ylene.

The term $C_3$-$C_7$-cycloalkyl means in the sense of the description, unless stated otherwise, a saturated hydrocarbon ring having 3 to 7 carbon ring members, such as cyclopropyl, cyclobutyl, cyclopentyl, cyclohexyl or cycloheptyl.

$C_1$-$C_6$-haloalkyl or $C_1$-$C_4$-haloalkyl is in the sense of the description, unless stated otherwise, a $C_1$-$C_6$-alkyl or $C_1$-$C_4$-alkyl as defined above in which one, more than one or all hydrogen atoms have been replaced by identical or different halogen atoms as defined below.

The term $C_2$-$C_6$-alkenyl means in the sense of the description, unless stated otherwise, a branched or unbranched hydrocarbon chain comprising at least one double bond and having 2 to 6 carbon atoms. $C_2$-$C_6$-alkenyl preferably comprises one or two double bonds, most preferably one double bond. Examples of the alkenyl groups are those mentioned above for alkyl, with these groups comprising one or two double bonds, such as, for example, vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-entenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl or 3-methyl-2-pentenyl.

The term $C_2$-$C_6$-alkynyl means in the sense of the description, unless stated otherwise, a branched or unbranched hydrocarbon chain comprising at least one triple bond and having 2 to 6 carbon atoms. $C_2$-$C_6$-alkynyl preferably comprises one or two triple bonds, most preferably one triple bond. Examples of alkynyl groups are those mentioned above for alkyl, with these groups comprising one or two triple bonds, such as, for example, ethynyl, 1-propynyl, 1-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, preferably ethynyl, 1-propynyl, 1-butynyl, 1-methyl-2-propynyl or 1-methyl-2-butynyl.

The terms "3- to 10-membered carbocycle" or "4 to 7 membered carbocyclic ring" or "carbocyclic ring having 3 to 10 C atoms" mean in the sense of the description, unless stated otherwise, a saturated or wholly or partly unsaturated hydrocarbon ring having 3 to 10 carbon atoms or 4 to 7 C atoms as ring atoms, such as, for example, cyclopropyl, cyclobutyl, cyclopentyl, cyclohexyl, cycloheptyl, cyclooctyl, cyclononyl or cyclodecenyl. Where explicitly mentioned, the carbocyclic ring may also comprise heteroatoms as ring atoms and is then referred to as heterocycle or heterocyclic ring. The heterocyclic ring has 2 to 10 carbon atoms and the number indicated in each case of heteroatoms as ring members. The heterocyclic ring may be saturated or partly unsaturated or aromatic (also referred to as heteroaromatic hereinafter). Monocyclic heteroaromatic rings typically have 5 or 6 ring atoms.

Halogen is in the sense of the description, unless stated otherwise, a halogen atom selected from fluorine, chlorine, bromine or iodine, preferably fluorine, chlorine or bromine, more preferably fluorine or chlorine.

The expressions "$C_1$-$C_6$-haloalkyl" or "$C_1$-$C_4$-haloalkyl" designate in the sense of the description, unless stated otherwise, an alkyl radical as defined above which is partially or completely substituted by one or more identical or different radicals selected independently of one another from the group consisting of fluorine, chlorine, bromine and iodine, thus for example $CH_2F$, $CHF_2$, $CF_3$, $CH_2Cl$, 2-fluoroethyl, 2-chloroethyl, 2,2,2-trifluoroethyl.

Where appropriately described by use of the expression "substituted", the radicals and groups can in the sense of the description, unless stated otherwise, be substituted, preferably one or more times, more preferably once, twice or three times, most preferably once or twice. The expression "in each case optionally substituted" is intended to make it clear that not only the radical immediately following but also all the radicals mentioned in the respective group may be substituted.

Examples of suitable substituents in the sense of the description include, unless stated otherwise: halogen, CN, $CF_3$, $CHF_2$, $OCF_3$, $OCHF_2$, $NO_2$, $NH_2$, OH, COOH, in each case branched or unbranched, optionally substituted $C_1$-$C_6$-alkyl, $C_3$-$C_7$-cycloalkyl, $C_1$-$C_6$-alkylene-O—$C_1$-$C_6$-alkyl or $C_1$-$C_6$-thioalkyl, O—$C_1$-$C_4$-alkyl, $N(C_1$-$C_4$-alkyl$)_2$, $NH(C_1$-$C_4$-alkyl), aryl, —O-aryl, $C_1$-$C_4$-alkylene-O-aryl, NHCO—$C_1$-$C_4$-alkyl, NH—$SO_2$—$C_1$-$C_4$-alkyl, CO—$C_{1-4}$-alkyl, $SO_2$—$C_1$-$C_4$-alkyl, and, optionally substituted in the aryl radical, NHCO-aryl, $NHSO_2$-aryl, $CONH_2$, $SO_2NH_2$, $SO_2$-aryl, SO—$C_1$-$C_4$-alkyl, SO-aryl, N-pyrrolidinyl, N-piperidinyl, and N-morpholinyl. Preferred substituents are F, Cl, $CF_3$, $OCF_3$, $NH_2$, $NO_2$, OH, COOH, $C_1$-$C_4$-alkyl, methoxy, acetyl, NH-acetyl and $SO_2NH_2$.

Expressions in parentheses with subscript integers are to be understood in the sense of the description, unless stated otherwise, in such a way that the meanings of the radicals in parentheses may in each case be identical or different. For example, $N(C_1$-$C_4$-alkyl$)_2$ stands in the sense of the description for $N(C_1$-$C_4$-alkyl$)(C_1$-$C_4$-alkyl), where the two ($C_1$-$C_4$-alkyl) radicals may be identical or different.

The symbol (*) in the chemical formulae of $R^1$, $R^2$, A, B and Y in the general formula (I) describes in the sense of the description, unless stated otherwise, the points of linkage of said radicals to the oxindole ring structure or a group connected to the oxindole ring structure.

The symbol (_) describes in the sense of the description, unless stated otherwise, a single bond which—if linked to a center of chirality—is intended to mean that the corresponding compound are in the form either of an approximately 1:1 mixture (racemate, (R/S) form) of the two enantiomeric forms in relation to the center of chirality, or else of separate enantiomers (R) and/or (S) in relation to the center of chirality.

The symbol —SO— means in the sense of the description, unless stated otherwise, a sulfoxide group (—S(=O)—).

The symbol —$SO_2$— means in the sense of the description, unless stated otherwise, alternatively a radical selected from the group consisting of the sulfone (—(O=S=O)—) and the sulfinic acid group (—(S=O)—O—), with the meaning of the sulfone group being preferably meant.

Where two radicals form a ring together with the atoms to which they are bonded, for example the radicals $R_Y^1$ and $R_Y^2$ or the radicals $R_Y^{21}$ and $R_Y^{22}$, the ring atoms defined by the radicals are carbon atoms unless indicated otherwise. Thus, for example, the radicals $R_Y^1$ and $R_Y^2$ may form together with the nitrogen atom and the carbon atom to which they are bonded a 4-, 5-, 6- or 7-membered nitrogen heterocycle which, besides the nitrogen atom to which $R_Y^1$ is bonded, includes 3, 4, 5 or 6 carbon atoms as ring members or 2, 3, 4 or 5 carbon atoms and a further heteroatom which is selected from O, S and $NR_Y^5$ as ring members. Thus, for example, the radicals $R_Y^{21}$ and $R_Y^{22}$ may form together with the nitrogen atom to which they are bonded a 4-, 5- or 6-membered nitrogen heterocycle which is saturated or wholly or partly unsaturated and, besides the nitrogen atom, comprises 3, 4 or 5 carbon atoms as ring members.

The expression "aromatic, heteroaromatic, partly aromatic or partly heteroaromatic mono- or bicyclic ring" means in the sense of the description, unless stated otherwise, a mono- or bicyclic ring which is composed of C atoms ("aromatic" or "partly aromatic") or of a combination of C atoms and heteroatoms ("heteroaromatic" or "partly heteroaromatic") in each case as ring members, and includes an aromatic number of double bonds in the ring ("monocyclic") or in the two rings ("bicyclic") ("aromatic" or "heteroaromatic") or only in one of the rings ("partly aromatic" or "partly heteroaromatic"). Aromatic and heteroaromatic rings comprise in particular 5- or 6-membered monocycles, and bicyclic systems of two fused 5- or 6-membered monocycles.

Examples of aromatic rings are phenyl, naphthyl, fluorenyl, indenyl and phenanthrenyl, more preferably phenyl and naphthyl, such as 1-naphthyl or 2-naphthyl. Phenyl is most preferred.

Examples of heteroaromatic rings are 2-furyl, 3-furyl, 2-pyrrolyl, 3-pyrrolyl, 2-thienyl, 3-thienyl, 2-pyridyl, 3-pyridyl, 4-pyridyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl, triazinyl, indolinyl, benzothienyl, naphthothienyl, benzofuranyl, chromenyl, indolyl, isoindolyl, indazolyl, quinolyl, isoquinolyl, phthalazinyl, quinoxalinyl, benzimidazolyl and benzoxazolyl, 2,3-dihydro-1,4-benzodioxinyl, 1,3-benzodioxolyl-, 2,1,3-benzothiadiazolyl.

The expressions "saturated or wholly or partly unsaturated carbocyclic ring" or "saturated or unsaturated carbocyclic ring" mean in the sense of the description, unless stated otherwise, a ring or ring system which is in each case formed of C atoms and has no double bond located in the ring ("saturated") or has one or more double bonds which are conjugated or unconjugated or only in part conjugated with one another ("partly or wholly unsaturated" or "unsaturated"). The carbocyclic ring may be a mono-, bi- or tricyclic ring. A bi- or tricyclic, saturated carbocycle may in the sense of the description, unless stated otherwise, be a bicycloalkyl or tricycloalkyl radical having 5 to 10 carbon atoms. In the case of a bicycloalkyl radical, the ring system may preferably comprise 5 to 10, more preferably 6 to 10, carbon atoms. In the case of a tricycloalkyl radical, the ring system preferably comprises 6 to 10, more preferably 7 to 10, carbon atoms. Examples of a bicycloalkyl radical include camphyl and norbornyl. Examples of a tricycloalkyl radical include adamantyl.

The expressions "saturated or wholly or partly unsaturated heterocyclic ring" or "saturated or unsaturated heterocyclic ring" mean in the sense of the description, unless stated otherwise, a ring or ring system which is formed in each case of 2, 3, 4, 5, 6, 7, 8, 9 or 10 carbon atoms and the indicated number of heteroatoms and which has no double bond located in the ring ("saturated") or has one or more double bonds which are conjugated or unconjugated or conjugated only in part with one another ("partly or wholly unsaturated" or "unsaturated"). The heterocyclic ring may be a mono-, bi- or tricyclic ring. A bi- or tricyclic, saturated heterocycle may in the sense of the description, unless stated otherwise, be a bicycle or tricycle having 5 to 10 ring atoms. In the case of a bicyclic ring, the ring system may preferably comprise 5 to 10, more preferably 6 to 10, ring atoms. In the case of a tricycle, the ring system preferably comprises 6 to 10, more preferably 7 to 10, ring atoms. An example of a bicycle which comprises carbon atoms and a nitrogen atom as ring members is indolyl.

The expression "in the sense of the description" includes the present application in all its parts, that is in particular the description, the claims, the drawings and the abstract.

The compounds of the invention are effective after administration by various routes (for example intravenously, intramuscularly, orally), especially orally.

The compounds of the invention show good affinity for vasopressin receptors, especially the vasopressin V1b receptor subtype. Since the various vasopressin receptors mediate very different effects of vasopressin (M. Thibonnier, Exp. Opin. Invest. Drugs 1998, 7(5), 729-740; Serradeil-Le Gal, C, et al.; Prog Brain Res. 2002; 139:197-210), it is particularly important to obtain effects selectively on, for example, one vasopressin receptor, in order thus to achieve the desired effect without simultaneously causing considerable side effects. Thus, vasopressin mediates for example effects on the kidney and its function via the V2 receptor, and this would be unwanted during a possible treatment of CNS disorders. Accordingly, besides the actual affinity for the target receptor, also particularly important is the selectivity vis-à-vis the other vasopressin receptors. A high affinity for a vasopressin receptor may likewise be advantageous because the desired effect is then achieved even with low serum levels, so that side effects can be reduced or even avoided in this way. The compounds of the invention show the advantage of having very good affinities for in particular the vasopressin V1b receptor and simultaneously generally displaying an improved selectivity vis-à-vis the other receptors such as V2.

The present invention also provides the use of the compounds of the invention for the treatment and/or prophylaxis of diseases in which the course of the disease is at least partially dependent on vasopressin, i.e. diseases which show an elevated vasopressin or oxytocin level which may contribute directly or indirectly to the pathological state.

The present invention further provides the use of the compounds of the invention for the treatment and/or prophylaxis of diseases such as, for example, diabetes insipidus, nocturnal enuresis, incontinence, diseases in which blood coagulation disorders occur and/or for delaying micturition.

The present invention also provides the use of the compounds of the invention for the treatment and/or prophylaxis of the following diseases: hypertension, pulmonary hypertension, heart failure, myocardial infarction, coronary spasm, unstable angina, PTCA (percutaneous transluminal coronary angioplastie), ischemias of the heart, disorders of the renal system, edemas, renal vasospasm, necrosis of the renal cortex, hyponatremia, hypokalemia, Schwartz-Bartter syndrome, disorders of the gastrointestinal tract, gastritic vasospasm, hepatocirrhosis, gastric and intestinal ulcer, emesis, emesis occurring during chemotherapy, and travel sickness.

The compounds of the invention can also be used for the treatment of various vasopressin-dependent or oxytocin-dependent complaints which have central nervous causes or alterations in the HPA axis (hypothalamic pituitary adrenal axis), for example for affective disorders such as depressive disorders and bipolar disorders. These include for example dythymic disorders, phobias, post-traumatic stress disorders, general anxiety disorders, panic disorders, seasonal depressions and sleep disorders. The disorders which can be treated according to the invention and which are associated with alterations in the HPA axis also include the disorders associated with drug withdrawal, especially withdrawal of opioid drugs or cocaine, including the increased tendency to relapse of formerly dependent individuals.

The compounds of the invention can likewise be employed for treatment in cases of anxiety disorders and stress-dependent anxiety disorders such as, for example, generalized anxiety disorders, phobias, post-traumatic anxiety disorders, panic anxiety disorders, obsessive-compulsive anxiety disorders, acute stress-dependent anxiety disorders and social phobia. The inventive compounds can further be employed also for the treatment of memory impairments, Alzheimer's disease, psychoses, psychotic disorders, sleep disorders and/or Cushing's syndrome.

The compounds of the invention are further suitable for the treatment of psychotic disorders/impairments such as schizophrenia.

The compounds of the invention are further suitable for the treatment of vasomotor disorders (vasomotor symptoms VMS) such as hot flushes or night sweats, and thus also for the prophylaxis of the sequelae associated therewith, such as lack of sleep and disorders and impairments resulting therefrom.

The present invention also relates to pharmaceutical compositions which comprise an effective dose of a compound of the invention or of a pharmaceutically acceptable salt thereof and suitable pharmaceutical carriers.

These pharmaceutical carriers are chosen according to the pharmaceutical form and the desired mode of administration.

The compounds of the invention of the general formula I or optionally suitable salts of these compounds can be used to produce pharmaceutical compositions for oral, sublingual, subcutaneous, intramuscular, intravenous, topical, intratracheal, intranasal, transdermal or rectal administration and can be administered to animals or humans in standard administration forms, mixed with conventional pharmaceutical carriers, for the prophylaxis or treatment of the above disorders or diseases.

The suitable standard administration forms comprise forms for oral administration, such as tablets, gelatin capsules, powders, granules and solutions or suspensions for oral intake, forms for sublingual, buccal, intratracheal or intranasal administration, aerosols, implants, forms of subcutaneous, intramuscular or intravenous administration and forms of rectal administration.

The compounds of the invention can be used in creams, ointments or lotions for topical administration.

In order to achieve the desired prophylactic or therapeutic effect, the dose of the active basic ingredient can vary between 0.01 and 50 mg per kg of body weight and per day.

Each unit dose may comprise from 0.05 to 5000 mg, preferably 1 to 1000 mg, of the active ingredient in combination with a pharmaceutical carrier. This unit dose may be administered 1 to 5 times a day, so that a daily dose of from 0.5 to 25 000 mg, preferably 1 to 5000 mg, is administered.

If a solid composition is prepared in the form of tablets, the main ingredient is mixed with a pharmaceutical carrier such as gelatin, starch, lactose, magnesium stearate, talc, silicon dioxide or the like.

The tablets can be coated with sucrose, a cellulose derivative or another suitable substance, or be treated otherwise in order to display a sustained or delayed activity and in order to release a predetermined amount of the active basic ingredient continuously.

A preparation in the form of gelatin capsules is obtained by mixing the active ingredient with an extender and including the resulting mixture in soft or hard gelatin capsules.

A preparation in the form of a syrup or elixir or for administration in the form of drops may comprise active ingredients together with a sweetener, which is preferably calorie-free, methylparaben or propylparaben as antiseptics, a flavoring and a suitable color.

Water-dispersible powders or granules may comprise the active ingredients mixed with dispersants, wetting agents or suspending agents, such as polyvinylpyrrolidones, and sweeteners or masking flavors.

Rectal administration is achieved by using suppositories which are prepared with binders which melt at the rectal temperature, for example cocoa butter or polyethylene glycols. Parenteral administration is effected by using aqueous suspensions, isotonic saline solutions or sterile and injectable solutions which comprise pharmacologically acceptable dispersants and/or wetting agents, for example propylene glycol or polyethylene glycol.

The active basic ingredient may also be formulated as microcapsules or centrosomes, where suitable with one or more carriers or additives.

In addition to the compounds of the general formula (I) or their pharmaceutically acceptable salts, the compositions of the invention may comprise other active basic ingredients which may be beneficial for the treatment of the disorders or diseases indicated above.

The present invention thus further relates to pharmaceutical compositions in which a plurality of active basic ingredients are present together, at least one of these being a compound of the invention.

The compounds of the invention represent antagonists of the so-called receptors of the vasopressin/oxytocin family. Such compounds can be investigated in suitable assays which ascertain the affinity for a receptor, where the affinity constant Ki represents a measure of the potency of the compounds and a smaller value represents a greater potency. The compounds of the invention have been tested for example for their receptor affinity in the following vasopressin receptor subtype V1b receptor for their affinity.

Preparation of the Compounds of the Invention

Examples of synthetic routes for preparing the compounds of the invention are described hereinafter.

The oxindoles of the invention can be prepared for example by the route outlined in synthesis scheme 1. The variables in synthesis schemes 1 have the same meanings as in the general formula (I)

SYNTHESIS SCHEME 1 ($R_4^{11}$ = OCH$_3$, $R^2$ = H)
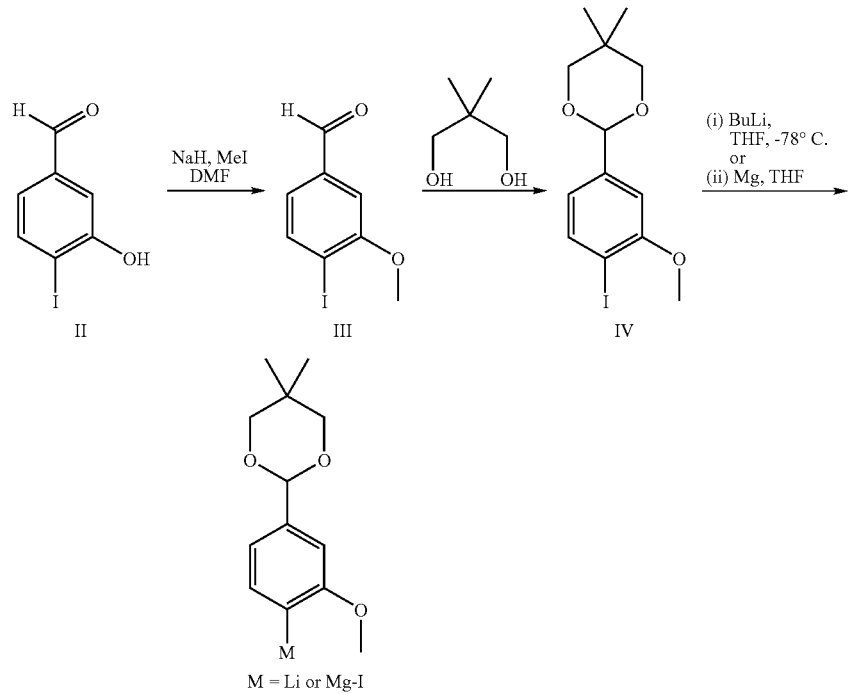
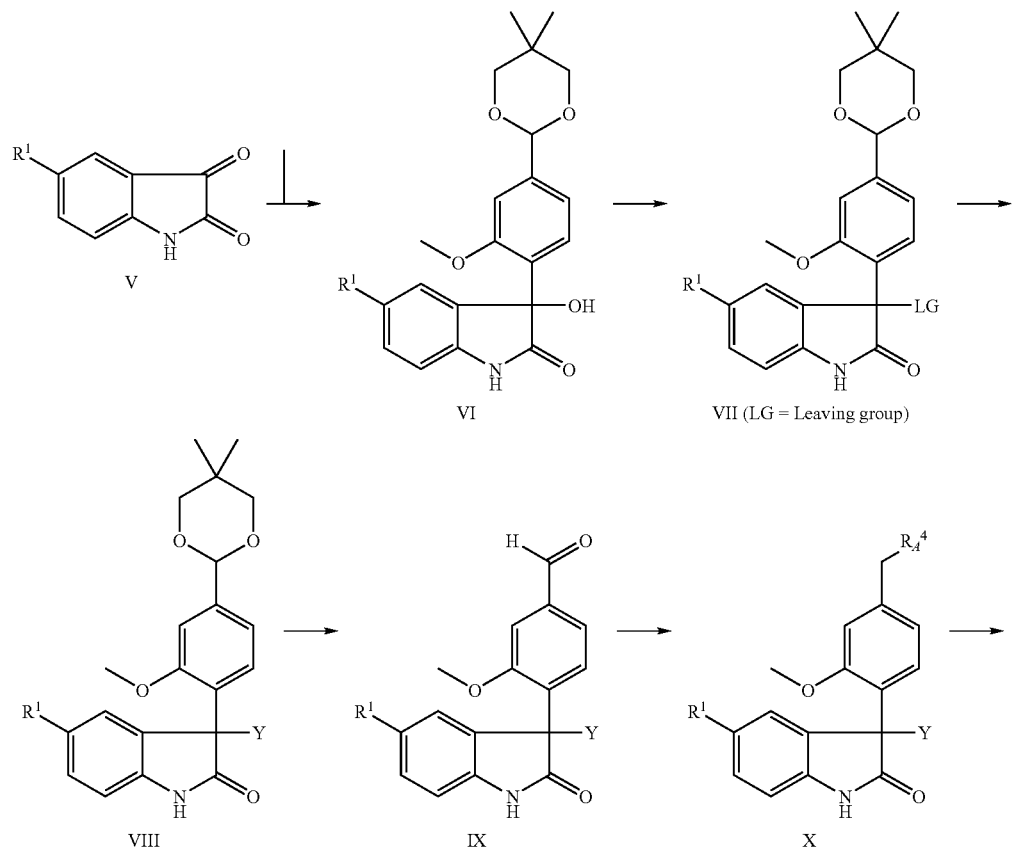

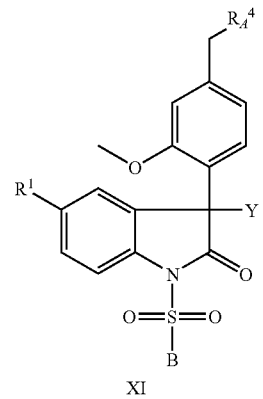

XI

Me = CH$_3$; Bu = C$_4$H$_9$

Compounds in which an amino group R$_A^4$ is linked via a methylene group to ring A can be synthesized in the manner shown in synthesis scheme 1. The 3-hydroxyoxindoles VI can be prepared by addition of organolithium or Grignard compounds onto the 3-keto group of the substituted isatins V in an ethereal solvent such as, for example, tetrahydrofuran (THF). For example (R$_A^{11}$=OCH$_3$) the lithium species can be obtained from the iodoaryl compound IV by treatment with organolithium reagents such as, for example, n-butyllithium in THF at low temperatures. Alternatively, the corresponding Grignard compound can be prepared from IV by treatment with magnesium in an ethereal solvent such as, for example, THF. The cyclic acetal IV can be prepared in two stages (methylation of the phenol oxygen followed by protection of the aldehyde as acetal) from commercially available 3-hydroxy-4-iodobenzaldehyde (II). The isomeric building block (protected aldehyde function para to the methoxy group) can be obtained in an analogous way from 3-bromo-4-methoxybenzaldehyde, which can be bought. Compounds with R$_A^{11}$=H can be synthesized by reacting Grignard compounds which can be bought, e.g. (3-(1-Pyrrolidinylmethyl) phenyl)magnesium bromide or (4-(1-pyrrolidinylmethyl) phenyl)magnesium bromide, with the isatins V.

In the case where A is an aromatic heterocycle, metallated heteroaromatic compounds having a protected formyl group can be prepared in an analogous manner (protection of the formyl function as cyclic acetal followed by lithium-halogen exchange or insertion of magnesium into the heteroaryl-halogen bond), e.g. from commercially available 2-bromo-4-formyl-3-methoxypyridine, 6-bromo-2-formylpyridine, 5-bromo-3-formylpyridine, 2-bromo-4-formylpyridine, 2-bromo-5-formylpyridine, 4-bromo-2-formylthiophene, 3-bromo-2-formylthiophene, 5-bromo-2-formylthiophene or 3-bromo-4-formylthiophene.

The 3-hydroxyoxindoles VI can be converted into the compounds VII having a leaving group LG in position 3, it being possible for the leaving group LG to be usual leaving groups such as, for example, halides, mesylate or tosylate. Thus, for example (LG=chlorine), the intermediate VII can be prepared by treating the alcohol VI with thionyl chloride in the presence of a base such as, for example, pyridine, in a solvent such as, for example, dichloromethane. The compounds VII are then reacted in the presence of a base such as, for example, N,N-diisopropylethylamine with primary or secondary amines Y—H such as, for example, (S)-pyrrolidine-2-dimethylcarboxamide (H-Pro-NMe$_2$), (2S,4R)-4-hydroxy-pyrrolidine-2-dimethylcarboxamide (H-Hyp-NMe$_2$) or (S)—N,N-di-methyl-2-methylaminopropionamide (H-MeAla-NMe$_2$), in a solvent such as, for example, dichloromethane, to give the corresponding 3-aminooxindoles VIII. After cleavage of the acetal protective group, e.g. by treatment with aqueous hydrochloric acid in acetone, the resulting aldehyde IX can be reacted with primary or secondary amines in the presence of a reducing agent such as, for example, sodium cyanoborohydride or solid phase-bound triacetoxyborohydride, in a solvent such as, for example, THF, to give the amines X (Reductive amination: J. March, Advanced Organic Chemistry, 1992, 4th edition., Wiley, New York, p. 411; 898). Sulfonylation of the oxindole nitrogen can take place by treatment of X with sulfonyl chlorides B—SO$_2$Cl after deprotonation with a strong base such as, for example, potassium tert-butoxide or sodium hydride, in a solvent such as, for example, N,N-dimethylformamide (DMF) or THF.

The cyano group as radical R$^1$ can be introduced starting from the corresponding compounds with R$^1$=iodine, for example by heating compound X or XI (with R$^1$=I) with zinc cyanide in DMF in the presence of catalytic amounts of palladium tetrakis-(triphenylphosphine) or by heating with potassium cyanide and catalytic amounts of palladium tetrakis(triphenylphosphine) in THF (J. Med. Chem. 1996, 39, 5072-5082).

SYNTHESIS SCHEME 2 ($R_4^{11}$ = $OCH_3$, $R^2$ = H)

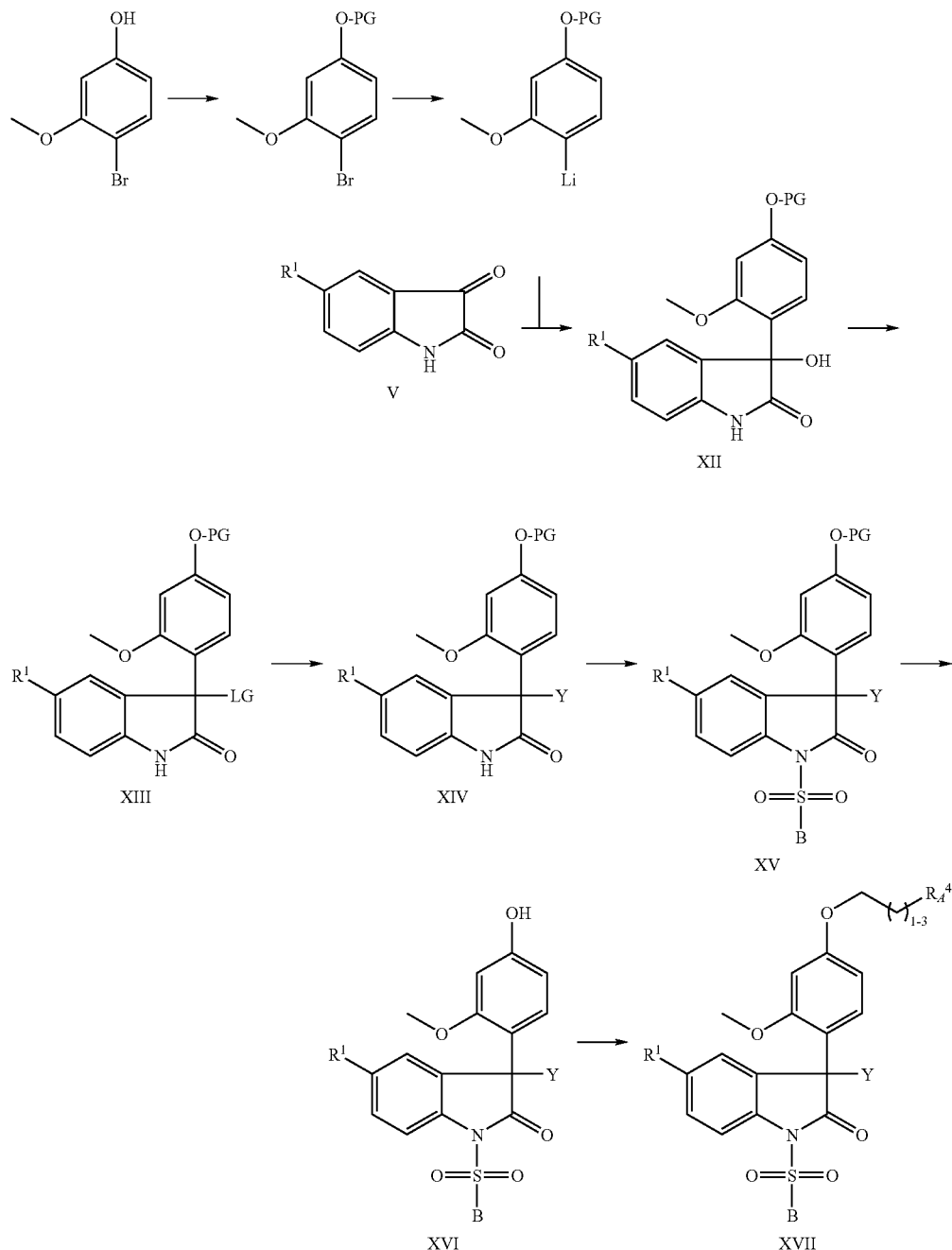

PG = Protective group

Compounds in which an amino group $R_A^4$ is linked via an O-alkylene group to ring A can be synthesized in the manner shown in synthesis scheme 2. The 3-hydroxyoxindoles XII can be prepared by addition of organolithium or Grignard compounds onto the 3-keto group of the substituted isatins V. For example ($R_A^{11}$=$OCH_3$), the corresponding lithium species can be obtained from 4-bromo-3-methoxyphenol after protection of the phenolic oxygen function with a suitable protective group PG, such as, for example, triisopropylsilyl, by treatment with organolithium reagents such as, for example, n-butyllithium, in an ethereal solvent such as, for example, THF, at low temperatures. Introduction of the leaving group LG, replacement of the leaving group LG by amines Y—H and sulfonylation of the oxindole nitrogen took place as described previously (synthesis scheme 1) and afforded the protected compound XV. After removal of the protective group PG, in the case of PG=triisopropylsilyl for example with tetrabutylammonium fluoride in THF, the phenolic oxygen function can be alkylated with alkyl halides which comprise substituted amino groups $R_A^4$, e.g. by heating the phenol XVI with the alkylating agent $R_A^4$—(C$_2$-C$_4$-alkyl)-Cl in DMF in the presence of a base such as potassium carbonate in a microwave.

The invention is explained in more detail below by means of examples without being restricted to the examples.

EXPERIMENTAL SECTION

Example 1

(S)-1-[5-Chloro-1-(2,4-dimethoxybenzenesulfonyl)-3-(2-methoxy-4-pyrrolidin-1-yl-methylphenyl)-2-oxo-2,3-dihydro-1H-indol-3-yl]-pyrrolidine-2-dimethylcarboxamide, Trifluoroacetic Acid Salt A) 2-(4-Iodo-3-methoxyphenyl)-5,5-dimethyl[1,3]dioxane Sodium hydride (887 mg, 60% dispersion in mineral oil, 22.2 mmol) was added to an ice-cooled solution of 3-hydroxy-4-iodobenzaldehyde (5.00 g, 20.2 mmol) in DMF (20 ml) and stirred at 0° C. for 60 min. Iodomethane (3.15 ml, 22.2 mmol) was added dropwise to the solution of the phenolate, and the reaction mixture was stirred at room temperature for 4 h. The mixture was diluted with ethyl acetate and washed with ice-water and saturated sodium chloride solution. After drying over magnesium sulfate, the organic phase was concentrated under reduced pressure. The residue (6.32 g) was dissolved in toluene (150 ml) and, after addition of neopentyl glycol (2.76 g, 26.5 mmol) and Amberlyst-15 (400 mg), the reaction mixture was heated under reflux with a water trap for 3 h. After filtration, the reaction solution was concentrated under reduced pressure and the residue was purified by chromatography on silica gel (mobile phase gradient 10-25% ethyl acetate in dichloromethane). Yield: 6.83 g (77%) of a yellowish oil. MS (API-ES, pos) m/z=349 [M+H]$^+$ B) 5-Chloro-3-[4-(5,5-dimethyl[1,3]dioxan-2-yl)-2-methoxyphenyl]-3-hydroxy-1,3-dihydro-indol-2-one A solution of n-butyllithium in hexane (1.6 m, 5.52 ml, 8.83 mmol) was slowly added dropwise to a solution of 2-(4-iodo-3-methoxyphenyl)-5,5-dimethyl[1,3]dioxane (3.00 g, 8.62 mmol) in THF (100 ml) at −78° C. After 15 min, a solution of 5-chloroisatin sodium salt [prepared by treating a solution of 5-chloroisatin (1.21 g, 6.64 mmol) in THF with one equivalent of sodium hydride at 0° C. for one h] was added dropwise to the solution of the organolithium species. The reaction mixture is allowed to warm to room temperature and then stirred for one further hour. Aqueous ammonium chloride solution was added to the reaction solution with stirring, and the mixture was extracted with ethyl acetate. The combined organic phase was washed with water and saturated sodium chloride solution, dried over magnesium sulfate and concentrated under reduced pressure. The desired product crystallizes on standing in the cold. Yield: 1.42 g (53%) of a white solid. MS (API-ES, pos) m/z=404 [M+H]$^+$ C) (S)-1-{5-Chloro-3-[4-(5,5-dimethyl[1,3]dioxan-2-yl)-2-methoxyphenyl]-2-oxo-2,3-dihydro-1H-indol-3-yl}pyrrolidine-2-dimethylcarboxamide, Mixture of Diastereomers Pyridine (0.68 ml, 8.43 mmol) and thionyl chloride (0.61 ml, 8.43 mmol) were added to a solution of the reaction product from stage 1B (2.84 g, 7.02 mmol) in dichloromethane (20 ml) while cooling in ice, and the mixture was stirred at 0° C. for 15 min. The reaction solution was quenched with water while stirring, and the mixture was extracted with dichloromethane. The organic phase was washed with water and saturated sodium chloride solution, dried over magnesium sulfate and concentrated under reduced pressure. N,N-Diisopropylethylamine (3.32 ml, 19.1 mmol) and (S)-pyrrolidine-2-dimethylcarboxamide (1.00 g, 7.01 mmol) were added to a solution of the 3-chlorooxindole intermediate obtained in this way in dichloromethane (20 ml), and the reaction mixture was stirred at room temperature for 18 h. After dilution with dichloromethane, the mixture was washed with water and saturated sodium chloride solution, dried over magnesium sulfate and concentrated under reduced pressure. The residue was purified by chromatography on silica gel (mobile phase gradient 1-5% methanol in dichloromethane). Yield: 3.08 g (79%) of a mixture of diastereomers. MS (API-ES, pos) m/z=528 [M+H]$^+$ D) (S)-1-[5-Chloro-3-(4-formyl-2-methoxyphenyl)-2-oxo-2,3-dihydro-1H-indol-3-yl]-pyrrolidine-2-dimethylcarboxamide, Mixture of Diastereomers A solution of the reaction product from stage 1C (1.00 g, 1.89 mmol) in a mixture of acetone (15 ml), dichloromethane (2 ml) and 2 N aqueous hydrochloric acid (10 ml) was stirred at room temperature for 72 h. The reaction was completed by heating at 50° C. for 45 min. The reaction mixture was diluted with dichloromethane and neutralized by adding sodium bicarbonate solution. The organic phase was washed with saturated sodium chloride solution, dried over magnesium sulfate and concentrated under reduced pressure. Yield: 650 mg (78%) of a white solid. MS (API-ES, pos) m/z=442 [M+H]$^+$ E) (S)-1-[5-Chloro-3-(2-methoxy-4-pyrrolidin-1-ylmethylphenyl)-2-oxo-2,3-dihydro-1H-indol-3-yl]-pyrrolidine-2-dimethylcarboxamide, Levorotatory Diastereomer Pyrrolidine (0.15 ml, 1.77 mmol) and MP-triacetoxyborohydride-resin (Argonaut, 2.04 g, f=1.8 mmol/g, 3.68 mmol) were added to a solution of the reaction product from stage 1D (650 mg, 1.47 mmol) in THF (5 ml) and the mixture was shaken at room temperature for 16 h. The solid-phase reagent was filtered off and washed with THF, and the filtrate was concentrated under reduced pressure. The residue was purified by chromatography on silica gel (mobile phase gradient 5-25% methanol in dichloromethane). Yield: 156 mg (21%) of the levorotatory diastereomer which elutes earlier, MS (API-ES, pos) m/z=497 [M+H]$^+$, [α]$_D$—124 (c 0.1, CHCl$_3$, 20° C.); 87 mg of the diastereomer which elutes later, MS (API-ES, pos) m/z=497 [M+H]$^+$.

F) (S)-1-[5-Chloro-1-(2,4-dimethoxybenzenesulfonyl)-3-(2-methoxy-4-pyrrolidin-1-yl-methylphenyl)-2-oxo-2,3-dihydro-1H-indol-3-yl]-pyrrolidine-2-dimethylcarboxamide, Trifluoroacetic Acid Salt (Example 1)

Sodium hydride (3 mg, 60% dispersion in mineral oil, 0.08 mmol) was added to a solution of the reaction product from stage 1E (30 mg of the levorotatory diastereomer which elutes earlier, 0.06 mmol) in DMF (2 ml) at 0° C. After 30 min, 2,4-dimethoxybenzenesulfonyl chloride (15 mg, 0.06 mmol) was added to the reaction solution and stirred at room temperature for a further 30 min. Sodium bicarbonate solution was added to the mixture, which was then extracted with ethyl acetate. The combined organic phase was washed with water and saturated sodium chloride solution, dried over magnesium sulfate and concentrated under reduced pressure. The residue was purified by preparative HPLC (mobile phase gradient 10-100% acetonitrile in water+0.1% trifluoroacetic acid). Yield: 20 mg (48%), MS (API-ES, pos) m/z=697 $[M+H]^+$.

Example 2

(S)-1-[5-Chloro-1-(4-methoxybenzenesulfonyl)-3-(2-methoxy-4-pyrrolidin-1-ylmethyl-phenyl)-2-oxo-2,3-dihydro-1H-indol-3-yl]pyrrolidine-2-dimethylcarboxamide A) (S)-1-[5-Chloro-3-[4-(5,5-dimethyl[1,3]dioxan-2-yl)-2-methoxyphenyl]-1-(4-methoxy-benzenesulfonyl)-2-oxo-2,3-dihydro-1H-indol-3-yl]pyrrolidine-2-dimethylcarboxamide, Mixture of Diastereomers Sodium hydride (136 mg, 60% dispersion in mineral oil, 3.41 mmol) was added to a solution of the reaction product from stage 1C (1500 mg, 2.84 mmol) in DMF (10 ml) at 0° C. After 30 min, 4-methoxybenzenesulfonyl chloride (616 mg, 2.98 mmol) was added to the reaction solution and stirred at room temperature for a further 30 min. Sodium bicarbonate solution was added to the mixture, which was then extracted with ethyl acetate. The combined organic phase was washed with water and saturated sodium chloride solution, dried over magnesium sulfate and concentrated under reduced pressure. Purification by chromatography on silica gel (mobile phase gradient 2-10% $CH_3OH$ in dichloromethane) afforded 1.71 g (86%) of the desired product as mixture of diastereomers. MS (API-ES, pos) m/z=698 $[M+H]^+$.

B) (S)-1-[5-Chloro-3-(4-formyl-2-methoxyphenyl)-1-(4-methoxybenzenesulfonyl)-2-oxo-2,3-dihydro-1H-indol-3-yl]pyrrolidine-2-dimethylcarboxamide, Levorotatory Diastereomer A solution of the reaction product from stage 2A (1.71 g, 2.45 mmol) in a mixture of acetone (25 ml) and 2 N aqueous hydrochloric acid (20 ml) was stirred at room temperature for 18 h. The reaction mixture was diluted with dichloromethane and neutralized by adding sodium bicarbonate solution. The reaction mixture was extracted twice with dichloromethane. The organic phase was washed with water, dried over magnesium sulfate and concentrated under reduced pressure. The residue was purified by chromatography on silica gel (mobile phase gradient 10-20% ethyl acetate in dichloromethane). Yield: 634 mg (42%) of the levorotatory diastereomer. MS (API-ES, pos) m/z=612 $[M+H]^+$; $[\alpha]_D$—180 (c 0.1, $CHCl_3$, 20° C.)

C) (S)-1-[5-Chloro-1-(4-methoxybenzenesulfonyl)-3-(2-methoxy-4-pyrrolidin-1-yl-methylphenyl)-2-oxo-2,3-dihydro-1H-indol-3-yl]pyrrolidine-2-dimethylcarboxamide A solution of the reaction product from stage 2B (350 mg, 0.57 mmol) in THF (4 ml) was mixed with pyrrolidine (0.06 ml, 0.7 mmol) and MP-triacetoxyborohydride-resin (Argonaut, 560 mg, f=2.6 mmol/g, 1.5 mmol) and shaken at room temperature for 16 h. The solid-phase reagent was filtered off and washed with THF, and the solution was concentrated under reduced pressure. The residue was purified by chromatography on silica gel (mobile phase gradient 2-10% methanol in dichloromethane). Yield: 289 mg (76%). MS (API-ES, pos) m/z=667 $[M+H]^+$; $^1H$ NMR (400 MHz, $d_6$-DMSO) 8.10 (d, 2H), 7.80 (m, 1H), 7.55 (d, 1H), 7.40 (d, 1H), 7.20 (d, 2H), 6.90 (m, 2H), 6.80 (s, 1H), 4.45 (m, 1H), 3.85 (s, 3H), 3.50 (m, 2H), 3.10 (br m, 2H), 2.55 (m, 2H), 2.40 (m, 7H), 1.80 (m, 1H), 1.70 (m, 4H), 1.45 (m, 2H).

In many cases, the products of the reductive amination were purified by preparative reversed phase HPLC (mobile phase: gradient from 10% to 80% acetonitrile in water, 0.1% trifluoroacetic acid) and accordingly result as trifluoroacetic acid salts.

The following compounds 3 to 16 were prepared in an analogous manner to that described for Examples 1 and 2 (synthesis scheme 1). (2S,4R)-4-Hydroxy-pyrrolidine-2-dimethylcarboxamide (H-Hyp-$NMe_2$) and (S)—N,N-dimethyl-2-methylaminopropionamide (H-MeAla-$NMe_2$) were prepared as described in WO05030755.

Example 3

(S)-1-[5-Chloro-1-(4-fluorobenzenesulfonyl)-3-(2-methoxy-4-pyrrolidin-1-ylmethyl-phenyl)-2-oxo-2,3-dihydro-1H-indol-3-yl]pyrrolidine-2-dimethylcarboxamide, Trifluoroacetic Acid Salt MS (API-ES, pos) m/z=655 $[M+H]^+$.

Example 4

(S)-1-[5-Chloro-1-(4-chlorobenzenesulfonyl)-3-(2-methoxy-4-pyrrolidin-1-ylmethyl-phenyl)-2-oxo-2,3-dihydro-1H-indol-3-yl]pyrrolidine-2-dimethylcarboxamide, Trifluoroacetic Acid Salt MS (API-ES, pos) m/z=671 $[M+H]^+$.

Example 5

(S)-1-[5-Chloro-1-(4-cyanobenzenesulfonyl)-3-(2-methoxy-4-pyrrolidin-1-ylmethyl-phenyl)-2-oxo-2,3-dihydro-1H-indol-3-yl]pyrrolidine-2-dimethylcarboxamide, Trifluoroacetic Acid Salt MS (API-ES, pos) m/z=662 $[M+H]^+$.

Example 6

(2S,4R)-1-[5-Chloro-1-(2,4-dimethoxybenzenesulfonyl)-2-oxo-3-(4-pyrrolidin-1-yl-methylphenyl)-2,3-dihydro-1H-indol-3-yl]-4-hydroxypyrrolidine-2-dimethylcarboxamide MS (API-ES, pos) m/z=683 $[M+H]^+$.

Example 7

(S)-1-[5-Chloro-1-(2,4-dimethoxybenzenesulfonyl)-3-(4-dimethylaminomethyl-2-methoxyphenyl)-2-oxo-2,3-dihydro-1H-indol-3-yl]-pyrrolidin-2-dimethylcarboxamide MS (API-ES, pos) m/z=671 $[M+H]^+$.

Example 8

(S)-1-[5-Chloro-1-(2,4-dimethoxybenzenesulfonyl)-3-(2-methoxy-4-piperidin-1-yl-methylphenyl)-2-oxo-2,3-dihydro-1H-indol-3-yl]pyrrolidine-2-dimethylcarboxamide MS (API-ES, pos) m/z=711 [M+H]$^+$.

Example 9

(S)-1-{5-Chloro-1-(2,4-dimethoxybenzenesulfonyl)-3-[2-methoxy-4-(4-methyl-piperazin-1-ylmethyl)phenyl]-2-oxo-2,3-dihydro-1H-indol-3-yl}pyrrolidine-2-dimethylcarboxamide MS (API-ES, pos) m/z=726 [M+H]$^+$.

Example 10

(S)-1-[5-Chloro-1-(2,4-dimethoxybenzenesulfonyl)-3-(2-methoxy-4-morpholin-4-yl-methylphenyl)-2-oxo-2,3-dihydro-1H-indol-3-yl]pyrrolidine-2-dimethylcarboxamide MS (API-ES, pos) m/z=713 [M+H]$^+$.

Example 11

(S)-1-[3-[4-(4-Acetylpiperazin-1-ylmethyl)-2-methoxyphenyl]-5-chloro-1-(2,4-dimethoxy-benzenesulfonyl)-2-oxo-2,3-dihydro-1H-indol-3-yl]pyrrolidine-2-dimethylcarboxamide MS (API-ES, pos) m/z=754 [M+H]$^+$.

Example 12

(S)-1-[5-Chloro-1-(2,4-dimethoxybenzenesulfonyl)-3-(4-{[(2-dimethylaminoethyl)-methylamino]methyl}-2-methoxyphenyl)-2-oxo-2,3-dihydro-1H-indol-3-yl]pyrrolidine-2-dimethylcarboxamide MS (API-ES, pos) m/z=728 [M+H]$^+$.

Example 13

(S)-2-{[5-Chloro-1-(2,4-dimethoxybenzenesulfonyl)-3-(4-dimethylaminomethyl-2-methoxyphenyl)-2-oxo-2,3-dihydro-1H-indol-3-yl]methylamino}-N,N-dimethyl-propionamide MS (API-ES, pos) m/z=659 [M+H]$^+$.

Example 14

(S)-2-{[5-Chloro-1-(2,4-dimethoxybenzenesulfonyl)-3-(2-methoxy-4-pyrrolidin-1-yl-methylphenyl)-2-oxo-2,3-dihydro-1H-indol-3-yl]methylamino}-N,N-dimethyl-propionamide MS (API-ES, pos) m/z=685 [M+H]$^+$.

Example 15

(S)-2-({5-Chloro-1-(2,4-dimethoxybenzenesulfonyl)-3-[2-methoxy-4-(4-methyl-piperazin-1-ylmethyl)phenyl]-2-oxo-2,3-dihydro-1H-indol-3-yl}methylamino)-N,N-dimethyl-propionamide MS (API-ES, pos) m/z=714 [M+H]$^+$.

Example 16

(2S,4R)-1-[5-Chloro-1-(2,4-dimethoxybenzenesulfonyl)-3-(3-dimethylaminomethyl-phenyl)-2-oxo-2,3-dihydro-1H-indol-3-yl]-4-hydroxypyrrolidine-2-dimethylcarboxamide MS (API-ES, pos) m/z=657 [M+H]$^+$.

Example 17

(S)-1-[5-Chloro-3-(5-dimethylaminomethyl-2-methoxyphenyl)-1-(4-methoxy-benzene-sulfonyl)-2-oxo-2,3-dihydro-1H-indol-3-yl]pyrrolidine-2-dimethylcarboxamide, Trifluoroacetic Acid Salt A) 2-(3-Bromo-4-methoxyphenyl)-5,5-dimethyl[1,3]dioxane 3-Bromo-4-methoxybenzaldehyde (60.0 g, 279 mmol) was dissolved in toluene (600 ml) and, after addition of neopentyl glycol (32.0 g, 306 mmol) and Amberlyst 15 (3.6 g), the reaction mixture was heated under reflux with a water trap for 2 h. After cooling, the reaction mixture was filtered, washed twice with water and then concentrated under reduced pressure. The remaining oil was mixed with heptane, whereupon the product precipitates and was filtered off and washed with heptane. Yield: 57.3 g (68% of theory). MS (API-ES, pos) m/z=301, 303 [M+H]$^+$ B) 5-Chloro-3-[5-(5,5-dimethyl-[1,3]dioxan-2-yl)-2-methoxyphenyl]-3-hydroxy-1,3-dihydroindol-2-one Magnesium turnings (2.2 g, 89 mmol) were introduced into THF (30 ml) and etched with some iodine crystals. While stirring, a solution of 2-(3-bromo-4-methoxy-phenyl)-5,5-dimethyl-[1,3]dioxane (26.0 g, 86 mmol) in THF (80 ml) was added thereto. After the reaction started (identifiable by the evolution of heat), the rate of dropwise addition was slowed down so that the reaction mixture just continued to boil. The reaction mixture was then stirred for 20 min and subsequently cooled to room temperature. The Grignard solution obtained in this way was pumped into an ice-cooled solution of 5-chloroisatin sodium salt [prepared by treating a solution of 5-chloroisatin (13.1 g, 72 mmol) in THF (400 ml) with one equivalent of sodium hydride at 0° C. for one h] and then stirred at room temperature for 5 hours. Aqueous ammonium chloride solution was added to the reaction solution while stirring, and the mixture was extracted twice with ethyl acetate. The combined organic phase was washed with water and saturated sodium chloride solution, dried over magnesium sulfate and concentrated under reduced pressure. The desired product crystallizes on treating the residue with diethyl ether. Yield: 19.2 g (66%) of a white solid. MS (API-ES, pos) m/z=386 [M+H−H$_2$O]$^+$

C) (S)-1-{5-Chloro-3-[5-(5,5-dimethyl[1,3]dioxan-2-yl)-2-methoxyphenyl]-2-oxo-2,3-dihydro-1H-indol-3-yl}pyrrolidine-2-dimethylcarboxamide, Mixture of Diastereomers Pyridine (0.24 ml, 3.0 mmol) and thionyl chloride (0.22 ml, 3.0 mmol) were added to a solution of the reaction product from stage 17B (1.00 g, 2.5 mmol) in dichloromethane (10 ml) while cooling in ice, and the mixture was stirred at 0° C. for 15 min. The reaction solution was quenched with water while stirring, and the mixture was extracted with dichloromethane. The organic phase was washed with water and saturated sodium chloride solution, dried over magnesium sulfate and concentrated under reduced pressure. N,N-Diisopropylethylamine (1.14 ml, 6.5 mmol) and H-Pro-NMe$_2$ (0.34 g, 2.4 mmol, Bachem) were added to a solution of the 3-chlorooxindole intermediate obtained in this way in dichloromethane (5 ml), and the reaction mixture was stirred at room temperature for 18 h. Sodium bicarbonate solution was added to the reaction mixture, which was then extracted several times with dichloromethane. The combined organic phase was washed with saturated sodium chloride solution, dried over magnesium sulfate and concentrated under reduced pressure. The residue was purified by chromatography on silica gel (mobile phase gradient 1-5% MeOH in dichloromethane). Yield: 0.55 g (44%) of the desired product as mixture of diastereomers. MS (API-ES, pos) m/z=528 [M+H]$^+$.

D) (S)-1-[5-Chloro-3-[5-(5,5-dimethyl[1,3]dioxan-2-yl)-2-methoxyphenyl]-1-(4-methoxybenzenesulfonyl)-2-oxo-2,3-dihydro-1H-indol-3-yl]pyrrolidine-2-dimethylcarboxamide, Mixture of Diastereomers Sodium hydride (18 mg, 60% dispersion in mineral oil, 0.45 mmol) was added to a solution of the reaction product from stage 17C (200 mg, 0.38 mmol) in DMF (5 ml) at 0° C. After 30 min, 4-methoxybenzenesulfonyl chloride (82 mg, 0.40 mmol) was added to the reaction solution while cooling in ice, and the mixture was stirred at room temperature for a further 45 min. Sodium bicarbonate solution was cautiously added to the mixture, which was then extracted twice with ethyl acetate. The combined organic phase was washed with water and saturated sodium chloride solution, dried over magnesium sulfate and concentrated under reduced pressure. The residue was purified by chromatography on silica gel (mobile phase gradient 15-30% ethyl acetate in dichloromethane). Yield: 150 mg (57%). MS (API-ES, pos) m/z=698 [M+H]$^+$.

E) (S)-1-[5-Chloro-3-(5-formyl-2-methoxyphenyl)-1-(4-methoxybenzenesulfonyl)-2-oxo-2,3-dihydro-1H-indol-3-yl]pyrrolidine-2-dimethylcarboxamide, Levorotatory diastereomer A solution of the reaction product from stage 17D (150 mg, 0.22 mmol) in a mixture of acetone (3 ml) and 2 N aqueous hydrochloric acid (3 ml) was stirred at room temperature for 18 h. The reaction mixture was diluted with dichloromethane and neutralized by adding sodium bicarbonate solution. The reaction mixture was extracted twice with dichloromethane. The organic phase was washed with water, dried over magnesium sulfate and concentrated under reduced pressure. The residue was purified by chromatography on silica gel (mobile phase gradient 10-30% ethyl acetate in dichloromethane). Yield: 63 mg (47%) of the levorotatory diastereomer which elutes earlier. MS (API-ES, pos) m/z=612 [M+H]$^+$.

F) (S)-1-[5-Chloro-3-(5-dimethylaminomethyl-2-methoxyphenyl)-1-(4-ethoxybenzene-sulfonyl)-2-oxo-2,3-dihydro-1H-indol-3-yl]pyrrolidine-2-dimethylcarboxamide, Trifluoroacetic Acid Salt A solution of the reaction product from stage 17E (50 mg, 0.08 mmol) in THF (1 ml) was mixed with a 2M solution of dimethylamine in THF (0.05 ml, 0.1 mmol) and MP-triacetoxyborohydride-resin (Argonaut, 89 mg, f=2.3 mmol/g, 0.20 mmol) and shaken at room temperature for 16 h. The solid-phase reagent was filtered off and washed with THF, and the solution was concentrated under reduced pressure. The residue was purified by preparative reversed phase HPLC (mobile phase: gradient from 10% to 80% acetonitrile in water, 0.1% trifluoroacetic acid). Yield: 37 mg (61%); MS (API-ES, pos) m/z=641 [M+H]$^+$.

The following Examples 18 to 33 were prepared in an analogous manner to that described for Example 17 (see synthesis scheme 1):

Example 18

(S)-1-[5-Chloro-1-(4-methoxybenzenesulfonyl)-3-(2-methoxy-5-pyrrolidin-1-yl-methylphenyl)-2-oxo-2,3-dihydro-1H-indol-3-yl]pyrrolidine-2-dimethylcarboxamide, Trifluoroacetic Acid Salt MS (API-ES, pos) m/z=667 [M+H]$^+$.

Example 19

(S)-1-[5-Chloro-1-(4-methoxybenzenesulfonyl)-3-(2-methoxy-5-piperidin-1-ylmethyl-phenyl)-2-oxo-2,3-dihydro-1H-indol-3-yl]pyrrolidine-2-dimethylcarboxamide, Trifluoroacetic Acid Salt MS (API-ES, pos) m/z=681 [M+H]$^+$.

Example 20

(S)-1-{5-Chloro-1-(4-methoxybenzenesulfonyl)-3-[2-methoxy-5-(4-methylpiperazin-1-yl-methyl)phenyl]-2-oxo-2,3-dihydro-1H-indol-3-yl}pyrrolidine-2-dimethylcarboxamide, Trifluoroacetic Acid Salt MS (API-ES, pos) m/z=696 [M+H]$^+$.

Example 21

(S)-1-[5-Chloro-1-(4-methoxybenzenesulfonyl)-3-(2-methoxy-5-morpholin-4-yl-methylphenyl)-2-oxo-2,3-dihydro-1H-indol-3-yl]pyrrolidine-2-dimethylcarboxamide, Trifluoroacetic Acid Salt MS (API-ES, pos) m/z=683 [M+H]$^+$.

Example 22

(S)-1-[5-Chloro-3-(5-{[(2-dimethylaminoethyl)methylamino]methyl}-2-methoxy-phenyl)-1-(4-methoxybenzenesulfonyl)-2-oxo-2,3-dihydro-1H-indol-3-yl]pyrrolidine-2-dimethylcarboxamide, Trifluoroacetic Acid Salt MS (API-ES, pos) m/z=698 [M+H]$^+$.

Example 23

(S)-1-[5-Chloro-3-(5-{[(3-dimethylaminopropyl)methylamino]methyl}-2-methoxy-phenyl)-1-(4-methoxybenzenesulfonyl)-2-oxo-2,3-dihydro-1H-indol-3-yl]pyrrolidine-2-dimethylcarboxamide, Trifluoroacetic Acid Salt MS (API-ES, pos) m/z=712 $[M+H]^+$.

Example 24

(S)-1-[5-Chloro-1-(2,4-dimethoxybenzenesulfonyl)-3-(5-dimethylaminomethyl-2-methoxyphenyl)-2-oxo-2,3-dihydro-1H-indol-3-yl]pyrrolidine-2-dimethylcarboxamide, Trifluoroacetic Acid Salt MS (API-ES, pos) m/z=671 $[M+H]^+$.

Example 25

(S)-1-[5-Chloro-1-(2,4-dimethoxybenzenesulfonyl)-3-(2-methoxy-5-pyrrolidin-1-yl-methylphenyl)-2-oxo-2,3-dihydro-1H-indol-3-yl]pyrrolidine-2-dimethylcarboxamide, Trifluoroacetic Acid Salt MS (API-ES, pos) m/z=697 $[M+H]^+$.

Example 26

(S)-1-[5-Chloro-1-(2,4-dimethoxybenzenesulfonyl)-3-(2-methoxy-5-piperidin-1-yl-methylphenyl)-2-oxo-2,3-dihydro-1H-indol-3-yl]pyrrolidin-2-dimethylcarboxamide Trifluoroacetic Acid Salt MS (API-ES, pos) m/z=711 $[M+H]^+$.

Example 27

(S)-1-{5-Chloro-1-(2,4-dimethoxybenzenesulfonyl)-3-[2-methoxy-5-(4-methyl-piperazin-1-ylmethyl)phenyl]-2-oxo-2,3-dihydro-1H-indol-3-yl}pyrrolidine-2-dimethylcarboxamide, Trifluoroacetic Acid Salt MS (API-ES, pos) m/z=726 $[M+H]^+$.

Example 28

(S)-1-[5-Chloro-1-(2,4-dimethoxybenzenesulfonyl)-3-(2-methoxy-5-morpholin-4-yl-methylphenyl)-2-oxo-2,3-dihydro-1H-indol-3-yl]pyrrolidine-2-dimethylcarboxamide, Trifluoroacetic Acid Salt MS (API-ES, pos) m/z=713 $[M+H]^+$.

Example 29

(S)-1-[5-Chloro-1-(2,4-dimethoxybenzenesulfonyl)-3-(5-{[(2-dimethylaminoethyl)-methylamino]methyl}-2-methoxyphenyl)-2-oxo-2,3-dihydro-1H-indol-3-yl]pyrrolidine-2-dimethylcarboxamide, Trifluoroacetic Acid Salt MS (API-ES, pos) m/z=728 $[M+H]^+$.

Example 30

(S)-1-[5-Chloro-1-(2,4-dimethoxybenzenesulfonyl)-3-(5-{[(3-dimethylaminopropyl)-methylamino]methyl}-2-methoxyphenyl)-2-oxo-2,3-dihydro-1H-indol-3-yl]pyrrolidine-2-dimethylcarboxamide, Trifluoroacetic Acid Salt MS (API-ES, pos) m/z=742 $[M+H]^+$.

Example 31

(S)-1-[5-Chloro-1-(2,4-dimethoxybenzenesulfonyl)-3-(2-methoxy-4-{[(2-methoxy-ethyl)methylamino]methyl}phenyl)-2-oxo-2,3-dihydro-1H-indol-3-yl]pyrrolidine-2-dimethylcarboxamide MS (API-ES, pos) m/z=715 $[M+H]^+$.

Example 32

(S)-1-[5-Chloro-1-(4-methoxybenzenesulfonyl)-3-(2-methoxy-5-{[(2-methoxyethyl)-methylamino]methyl}phenyl)-2-oxo-2,3-dihydro-1H-indol-3-yl]-pyrrolidine-2-dimethylcarboxamide, Trifluoroacetic Acid Salt MS (API-ES, pos) m/z=685 $[M+H]^+$.

Example 33

(S)-1-[5-Chloro-1-(2,4-dimethoxybenzenesulfonyl)-3-(2-methoxy-5-{[(2-methoxy-ethyl)methylamino]methyl}phenyl)-2-oxo-2,3-dihydro-1H-indol-3-yl]pyrrolidine-2-dimethylcarboxamide, Trifluoroacetic Acid Salt MS (API-ES, pos) m/z=715 $[M+H]^+$.

Example 34

(S)-1-{5-Chloro-1-(4-cyanobenzenesulfonyl)-3-[2-methoxy-4-(2-pyrrolidin-1-yl-ethoxy)phenyl]-2-oxo-2,3-dihydro-1H-indol-3-yl}pyrrolidine-2-dimethylcarboxamide, Trifluoroacetic Acid Salt A) (4-Bromo-3-methoxyphenoxy)triisopropylsilane A solution of 4-bromo-3-methoxyphenol (5.00 g, 24.6 mmol, Chontech) in THF (50 ml) was added dropwise to a suspension of sodium hydride (1.08 g, 60% dispersion in mineral oil, 27 mmol) in THF (100 ml) over 10 min while cooling in ice. The reaction mixture was stirred at 0° C. for 30 min and then at room temperature for 60 min. Triisopropylsilyl chloride was added dropwise to the phenolate solution, and the reaction mixture was stirred at room temperature for 60 min. Water was added to the mixture while cooling in ice, and it was then extracted several times with ethyl acetate. The combined organic phase was washed with saturated sodium chloride solution, dried over magnesium sulfate and concentrated under reduced pressure. Purification by chromatography on silica gel (mobile phase: 2-10% gradient of ethyl acetate in dichloromethane) afforded 8.67 g (98%) of the desired product.

B) 5-Chloro-3-hydroxy-3-(2-methoxy-4-triisopropylsilanyloxyphenyl)-1,3-dihydroindol-2-one A solution of n-butyllithium in hexane (1.6 m, 19.6 ml, 31.4 mmol) was slowly added dropwise to a solution of (4-bromo-3-methoxyphenoxy)triisopropylsilane (8.67 g, 24.1 mmol) in THF (100 ml) at −15° C. After 15 min, a solution of 5-chloroisatin sodium salt [prepared by treating a solution of 5-chloroisatin (3.65 g, 20.1 mmol) in THF with one equivalent of sodium hydride at 0° C. for one h] was added dropwise to the solution of the organolithium species. The reaction mixture was allowed to warm to room temperature and was stirred for a further hour. Aqueous ammonium chloride solution was added to the reaction solution while stirring, and the mixture was extracted with ethyl acetate. The combined organic phase was washed with water and saturated sodium chloride solution, dried over magnesium sulfate and concentrated under reduced pressure. Purification by chromatography on silica gel (mobile phase 10-30% gradient of ethyl acetate in dichloromethane) afforded 3.8 g (41%) of the desired adduct.

C) (S)-1-[5-Chloro-3-(2-methoxy-4-triisopropylsilanyloxyphenyl)-2-oxo-2,3-dihydro-1H-indol-3-yl]pyrrolidine-2-dimethylcarboxamide, Levorotatory Diastereomer Pyridine (0.53 ml, 6.5 mmol) and thionyl chloride (0.47 ml, 6.5 mmol) were added to a solution of the reaction product from stage 34B (2.50 g, 5.4 mmol) in dichloromethane (20 ml) while cooling in ice, and the mixture was stirred at 0° C. for 15 min. The reaction solution was quenched with water while stirring, and the mixture was extracted with dichloromethane. The organic phase was washed with water and saturated sodium chloride solution, dried over magnesium sulfate and concentrated under reduced pressure. N,N-Diisopropylethylamine (3.0 ml, 17.0 mmol) and (S)-pyrrolidine-2-dimethylcarboxamide (0.89 g, 6.2 mmol, Bachem) were added to a solution of the 3-chlorooxindole intermediate obtained in this way in dichloromethane (10 ml), and the reaction mixture was stirred at room temperature for 18 h. The reaction mixture was mixed with water and extracted several times with dichloromethane. The combined organic phase was washed with saturated sodium chloride solution, dried over magnesium sulfate and concentrated under reduced pressure. The residue was purified by chromatography on silica gel (mobile phase gradient 20-50% ethyl acetate in dichloromethane). Yield: 0.83 g (22%) of the levorotatory diastereomer which elutes earlier. MS (API-ES, pos) m/z=586 [M+H]$^+$; [α]$_D$—150 (c 0.1, CHCl$_3$, 20° C.)

D) (S)-1-[5-Chloro-1-(4-cyanobenzenesulfonyl)-3-(2-methoxy-4-triisopropylsilanyl-oxyphenyl)-2-oxo-2,3-dihydro-1H-indol-3-yl]-pyrrolidine-2-dimethylcarboxamide Sodium hydride (13 mg, 60% dispersion in mineral oil, 0.33 mmol) was added to a solution of the reaction product from stage 34C (160 mg, 0.27 mmol) in DMF (2 ml) at 0° C. After 30 min, 4-cyanobenzenesulfonyl chloride (66 mg, 0.33 mmol) was added to the reaction solution while cooling in ice, and the mixture was stirred at room temperature for a further 45 min. Sodium bicarbonate solution was cautiously added to the mixture, which was then extracted twice with ethyl acetate. The combined organic phase was washed with water and saturated sodium chloride solution, dried over magnesium sulfate and concentrated under reduced pressure. The residue was purified by chromatography on silica gel (mobile phase gradient 40-100% ethyl acetate in dichloromethane). Yield: 148 mg (72%).

E) (S)-1-[5-Chloro-1-(4-cyanobenzenesulfonyl)-3-(4-hydroxy-2-methoxyphenyl)-2-oxo-2,3-dihydro-1H-indol-3-yl]pyrrolidine-2-dimethylcarboxamide A solution of tetra-n-butylammonium fluoride in THF (1.0 m, 10 ml, 10 mmol) was added to a solution of the reaction product from stage 34D (574 mg, 0.76 mmol) in THF (10 ml) at 0° C. After 30 min, water was added to the mixture, which was then extracted several times with ethyl acetate. The combined organic phase was washed with saturated sodium chloride solution, dried over magnesium sulfate and concentrated under reduced pressure. The residue was purified by chromatography on silica gel (mobile phase gradient 70-100% ethyl acetate in dichloromethane). Yield: 376 mg (83%). MS (API-ES, pos) m/z=595 [M+H]$^+$.

F) (S)-1-{5-Chloro-1-(4-cyanobenzenesulfonyl)-3-[2-methoxy-4-(2-pyrrolidin-1-yl-ethoxy)phenyl]-2-oxo-2,3-dihydro-1H-indol-3-yl}pyrrolidine-2-dimethylcarboxamide, Trifluoroacetic Acid Salt The reaction product from stage 34E (35 mg, 0.06 mmol) was heated together with 1-(2-chloroethyl)pyrrolidine hydrochloride (19 mg, 0.12 mmol) and finely powdered potassium carbonate (24 mg, 0.18 mmol) in DMF (0.5 ml) in a microwave (100° C., 150 W). The filtrate after filtration was concentrated and purified by preparative reversed phase HPLC. Yield: 13 mg; MS (API-ES, pos) m/z=692 [M+H]$^+$.

The following Examples 35 to 39 were prepared in an analogous manner to that described for Example 34 (see synthesis scheme 2):

Example 35

(S)-1-{5-Chloro-1-(4-cyanobenzenesulfonyl)-3-[4-(2-dimethylaminoethoxy)-2-methoxyphenyl]-2-oxo-2,3-dihydro-1H-indol-3-yl}pyrrolidine-2-dimethylcarboxamide, Trifluoroacetic Acid Salt MS (API-ES, pos) m/z=666 [M+H]$^+$.

Example 36

(S)-1-{5-Chloro-1-(4-cyanobenzenesulfonyl)-3-[2-methoxy-4-(2-morpholin-4-yl-ethoxy)phenyl]-2-oxo-2,3-dihydro-1H-indol-3-yl}pyrrolidine-2-dimethylcarboxamide, Trifluoroacetic Acid Salt MS (API-ES, pos) m/z=708 [M+H]$^+$.

Example 37

(S)-1-{5-Chloro-1-(4-cyanobenzenesulfonyl)-3-[2-methoxy-4-(3-piperidin-1-yl-propoxy)phenyl]-2-oxo-2,3-dihydro-1H-indol-3-yl}pyrrolidine-2-dimethylcarboxamide, Trifluoroacetic Acid Salt MS (API-ES, pos) m/z=720 [M+H]$^+$.

Example 38

(S)-1-{5-Chloro-1-(4-cyanobenzenesulfonyl)-3-[4-(3-dimethylaminopropoxy)-2-methoxyphenyl]-2-oxo-2,3-dihydro-1H-indol-3-yl}pyrrolidine-2-dimethylcarboxamide, Trifluoroacetic Acid Salt MS (API-ES, pos) m/z=680 [M+H]$^+$.

Example 39

(S)-1-(5-Chloro-1-(4-cyanobenzenesulfonyl)-3-{2-methoxy-4-[3-(4-methylpiperazin-1-yl)propoxy]phenyl}-2-oxo-2,3-dihydro-1H-indol-3-yl)pyrrolidine-2-dimethylcarboxamide MS (API-ES, pos) m/z=735 [M+H]$^+$.

In addition, Examples 40 to 68 mentioned below can be prepared in an analogous manner as shown in synthesis scheme 1.

Example 40

(S)-1-[5-Chloro-3-(2-methoxy-4-pyrrolidin-1-ylmethylphenyl)-2-oxo-1-(pyridine-2-sulfonyl)-2,3-dihydro-1H-indol-3-yl]pyrrolidin-2-dimethylcarboxamide

Example 41

(S)-1-[5-Chloro-3-(2-methoxy-4-pyrrolidin-1-ylmethylphenyl)-1-(5-methylpyridine-2-sulfonyl)-2-oxo-2,3-dihydro-1H-indol-3-yl]pyrrolidine-2-dimethylcarboxamide

Example 42

(S)-1-[5-Chloro-1-(5-chloropyridin-2-sulfonyl)-3-(2-methoxy-4-pyrrolidin-1-ylmethyl-phenyl)-2-oxo-2,3-dihydro-1H-indol-3-yl]pyrrolidine-2-dimethylcarboxamide

Example 43

(S)-1-[5-Chloro-3-(2-methoxy-4-pyrrolidin-1-ylmethylphenyl)-2-oxo-1-(thiophene-2-sulfonyl)-2,3-dihydro-1H-indol-3-yl]pyrrolidine-2-dimethylcarboxamide

Example 44

(S)-1-[(5-Chloro-3-(2-methoxy-4-pyrrolidin-1-ylmethylphenyl)-2-oxo-1-(thiophene-3-sulfonyl)-2,3-dihydro-1H-indol-3-yl]pyrrolidine-2-dimethylcarboxamide

Example 45

(S)-1-[5-Chloro-3-(2-methoxy-4-pyrrolidin-1-ylmethylphenyl)-2-oxo-1-(quinoline-8-sulfonyl)-2,3-dihydro-1H-indol-3-yl]pyrrolidine-2-dimethylcarboxamide

Example 46

(2S,4R)-1-[5-Cyano-1-(4-methoxybenzenesulfonyl)-3-(2-methoxy-4-pyrrolidin-1-yl-methylphenyl)-2-oxo-2,3-dihydro-1H-indol-3-yl]-4-hydroxypyrrolidine-2-dimethylcarboxamide

Example 47

(2S,4R)-1-[5-Chloro-1-(4-methoxybenzenesulfonyl)-3-(2-methoxy-4-pyrrolidin-1-yl-methylphenyl)-2-oxo-2,3-dihydro-1H-indol-3-yl]-4-fluoropyrrolidine-2-dimethylcarboxamide

Example 48

(S)-1-[5-Chloro-1-(4-methoxybenzenesulfonyl)-3-(2-methoxy-4-pyrrolidin-1-yl-methylphenyl)-2-oxo-2,3-dihydro-1H-indol-3-yl]piperidine-2-dimethylcarboxamide

Example 49

(S)-2-[5-Chloro-1-(4-methoxybenzenesulfonyl)-3-(2-methoxy-4-pyrrolidin-1-yl-methylphenyl)-2-oxo-2,3-dihydro-1H-indol-3-ylamino]-N,N-dimethylpropionamide

Example 50

(S)-1-[5-Cyano-3-(2-methoxy-4-pyrrolidin-1-ylmethylphenyl)-2-oxo-1-(pyridine-2-sulfonyl)-2,3-dihydro-1H-indol-3-yl]pyrrolidine-2-dimethylcarboxamide

Example 51

(S)-1-[5-Cyano-3-(2-methoxy-4-pyrrolidin-1-ylmethylphenyl)-1-(5-methylpyridin-2-sulfonyl)-2-oxo-2,3-dihydro-1H-indol-3-yl]pyrrolidine-2-dimethylcarboxamide

Example 52

(S)-1-[5-Cyano-1-(5-chloropyridine-2-sulfonyl)-3-(2-methoxy-4-pyrrolidin-1-ylmethyl-phenyl)-2-oxo-2,3-dihydro-1H-indol-3-yl]pyrrolidine-2-dimethylcarboxamide

Example 53

(S)-1-[5-Cyano-3-(2-methoxy-4-pyrrolidin-1-ylmethylphenyl)-2-oxo-1-(thiophene-2-sulfonyl)-2,3-dihydro-1H-indol-3-yl]pyrrolidine-2-dimethylcarboxamide

Example 54

(S)-1-[(5-Cyano-3-(2-methoxy-4-pyrrolidin-1-ylmethylphenyl)-2-oxo-1-(thiophene-3-sulfonyl)-2,3-dihydro-1H-indol-3-yl]pyrrolidine-2-dimethylcarboxamide

Example 55

(S)-1-[5-Cyano-3-(2-methoxy-4-pyrrolidin-1-ylmethylphenyl)-2-oxo-1-(quinoline-8-sulfonyl)-2,3-dihydro-1H-indol-3-yl]pyrrolidine-2-dimethylcarboxamide

Example 56

(S)-1-[5-Cyano-1-(4-methoxybenzenesulfonyl)-3-(2-methoxy-4-pyrrolidin-1-yl-methylphenyl)-2-oxo-2,3-dihydro-1H-indol-3-yl]pyrrolidin-2-dimethylcarboxamide

Example 57

(2S,4R)-1-[5-Cyano-1-(4-methoxybenzenesulfonyl)-3-(2-methoxy-4-pyrrolidin-1-yl-methylphenyl)-2-oxo-2,3-dihydro-1H-indol-3-yl]-4-hydroxypyrrolidine-2-dimethylcarboxamide

Example 58

(2S,4R)-1-[5-Cyano-1-(4-methoxybenzenesulfonyl)-3-(2-methoxy-4-pyrrolidin-1-yl-methylphenyl)-2-oxo-2,3-dihydro-1H-indol-3-yl]-4-fluoropyrrolidine-2-dimethylcarboxamide

Example 59

(S)-1-[5-Cyano-1-(4-methoxybenzenesulfonyl)-3-(2-methoxy-4-pyrrolidin-1-yl-methylphenyl)-2-oxo-2,3-dihydro-1H-indol-3-yl]piperidine-2-dimethylcarboxamide

Example 60

(S)-2-[5-Cyano-1-(4-methoxybenzenesulfonyl)-3-(2-methoxy-4-pyrrolidin-1-yl-methylphenyl)-2-oxo-2,3-dihydro-1H-indol-3-ylamino]-N,N-dimethylpropionamide

Example 61

(S)-1-[5-Cyano-3-(5-dimethylaminomethyl-2-methoxyphenyl)-1-(4-methoxy-benzenesulfonyl)-2-oxo-2,3-dihydro-1H-indol-3-yl]pyrrolidine-2-dimethylcarboxamide

Example 62

(S)-1-[5-Cyano-1-(4-methoxybenzenesulfonyl)-3-(2-methoxy-5-pyrrolidin-1-yl-methylphenyl)-2-oxo-2,3-dihydro-1H-indol-3-yl]pyrrolidine-2-dimethylcarboxamide

Example 63

(S)-1-[5-Cyano-1-(4-methoxybenzenesulfonyl)-3-(2-methoxy-5-piperidin-1-ylmethyl-phenyl)-2-oxo-2,3-dihydro-1H-indol-3-yl]pyrrolidine-2-dimethylcarboxamide

Example 64

(S)-1-{5-Cyano-1-(4-methoxybenzenesulfonyl)-3-[2-methoxy-5-(4-methylpiperazin-1-yl-methyl)phenyl]-2-oxo-2,3-dihydro-1H-indol-3-yl}pyrrolidine-2-dimethylcarboxamide

Example 65

(S)-1-[5-Cyano-1-(4-methoxybenzenesulfonyl)-3-(2-methoxy-5-morpholin-4-yl-methylphenyl)-2-oxo-2,3-dihydro-1H-indol-3-yl]pyrrolidine-2-dimethylcarboxamide

Example 66

(S)-1-[5-Cyano-3-(5-{[(2-dimethylaminoethyl)methylamino]methyl}-2-methoxy-phenyl)-1-(4-methoxybenzenesulfonyl)-2-oxo-2,3-dihydro-1H-indol-3-yl]pyrrolidine-2-dimethylcarboxamide

Example 67

(S)-1-[5-Cyano-3-(5-{[(3-dimethylaminopropyl)methylamino]methyl}-2-methoxy-phenyl)-1-(4-methoxybenzenesulfonyl)-2-oxo-2,3-dihydro-1H-indol-3-yl]pyrrolidine-2-dimethylcarboxamide

Example 68

(S)-1-[5-Cyano-1-(4-methoxybenzenesulfonyl)-3-(2-methoxy-5-{[(2-methoxy-ethyl)methylamino]methyl}phenyl)-2-oxo-2,3-dihydro-1H-indol-3-yl]pyrrolidin-2-dimethylcarboxamide In addition, the following Examples 69 to 102 can be prepared in an analogous manner to that described for Examples 2 and 17 (synthesis scheme 1):

Example 69

(S)-1-{5-Chloro-1-(4-methoxybenzenesulfonyl)-3-[2-methoxy-4-(4-methylpiperazin-1-ylmethyl)phenyl]-2-oxo-2,3-dihydro-1H-indol-3-yl}pyrrolidine-2-dimethylcarboxamide, Trifluoroacetic Acid Salt MS (API-ES, pos) m/z=696 [M+H]$^+$.

Example 70

(S)-1-[5-Chloro-3-(4-dimethylaminomethyl-2-methoxyphenyl)-1-(4-methoxy-benzenesulfonyl)-2-oxo-2,3-dihydro-1H-indol-3-yl]pyrrolidine-2-dimethylcarboxamide, Trifluoroacetic Acid Salt MS (API-ES, pos) m/z=641 [M+H]$^+$.

Example 71

(S)-1-[5-Chloro-1-(4-methoxybenzenesulfonyl)-3-(2-methoxy-4-morpholin-4-yl-methylphenyl)-2-oxo-2,3-dihydro-1H-indol-3-yl]pyrrolidine-2-dimethylcarboxamide, Trifluoroacetic Acid Salt MS (API-ES, pos) m/z=683 [M+H]$^+$.

Example 72

(S)-1-[5-Chloro-1-(4-cyanobenzenesulfonyl)-3-(4-dimethylaminomethyl-2-methoxy-phenyl)-2-oxo-2,3-dihydro-1H-indol-3-yl]pyrrolidine-2-dimethylcarboxamide, Trifluoroacetic Acid Salt MS (API-ES, pos) m/z=636 [M+H]$^+$.

Example 73

(S)-1-[5-Chloro-3-(4-dimethylaminomethyl-2-methoxyphenyl)-1-(4-fluorobenzene-sulfonyl)-2-oxo-2,3-dihydro-1H-indol-3-yl]pyrrolidine-2-dimethylcarboxamide, Trifluoroacetic Acid Salt MS (API-ES, pos) m/z=629 [M+H]$^+$.

Example 74

(S)-1-{5-Chloro-1-(4-fluorobenzenesulfonyl)-3-[2-methoxy-4-(4-methylpiperazin-1-yl-methyl)phenyl]-2-oxo-2,3-dihydro-1H-indol-3-yl}pyrrolidine-2-dimethylcarboxamide, Trifluoroacetic Acid Salt MS (API-ES, pos) m/z=684 [M+H]$^+$.

Example 75

(S)-1-[3-(4-Aminomethyl-2-methoxyphenyl)-5-chloro-1-(4-fluorobenzenesulfonyl)-2-oxo-2,3-dihydro-1H-indol-3-yl]pyrrolidine-2-dimethylcarboxamide, Trifluoroacetic Acid Salt MS (API-ES, pos) m/z=602 [M+H]$^+$.

Example 76

(S)-1-[3-(4-Aminomethyl-2-methoxyphenyl)-5-chloro-1-(4-cyanobenzenesulfonyl)-2-oxo-2,3-dihydro-1H-indol-3-yl]pyrrolidine-2-dimethylcarboxamide, Trifluoroacetic Acid Salt MS (API-ES, pos) m/z=609 [M+H]$^+$.

Example 77

(S)-1-[5-Chloro-1-(4-fluorobenzenesulfonyl)-3-(2-methoxy-4-morpholin-4-ylmethyl-phenyl)-2-oxo-2,3-dihydro-1H-indol-3-yl]pyrrolidine-2-dimethylcarboxamide, Trifluoroacetic Acid Salt MS (API-ES, pos) m/z=671 [M+H]$^+$.

Example 78

(S)-1-[5-Chloro-1-(4-fluorobenzenesulfonyl)-3-(2-methoxy-4-piperazin-1-ylmethyl-phenyl)-2-oxo-2,3-dihydro-1H-indol-3-yl]pyrrolidine-2-dimethylcarboxamide, Trifluoroacetic Acid Salt MS (API-ES, pos) m/z=670 [M+H]$^+$.

Example 79

(S)-1-[5-Chloro-1-(4-methoxybenzenesulfonyl)-3-(2-methoxy-4-piperazin-1-yl-methylphenyl)-2-oxo-2,3-dihydro-1H-indol-3-yl]pyrrolidine-2-dimethylcarboxamide, Trifluoroacetic Acid Salt MS (API-ES, pos) m/z=682 [M+H]$^+$.

Example 80

(S)-1-{5-Chloro-1-(4-cyanobenzenesulfonyl)-3-[2-methoxy-4-(4-methylpiperazin-1-ylmethyl)phenyl]-2-oxo-2,3-dihydro-1H-indol-3-yl}pyrrolidine-2-carboxylic Acid Dimethylamide, Trifluoroacetic Acid Salt MS (API-ES, pos) m/z=691 [M+H]$^+$.

Example 81

(S)-1-[5-Chloro-1-(4-cyanobenzenesulfonyl)-3-(2-methoxy-4-morpholin-4-ylmethyl-phenyl)-2-oxo-2,3-dihydro-1H-indol-3-yl]pyrrolidine-2-dimethylcarboxamide, Trifluoroacetic Acid Salt MS (API-ES, pos) m/z=678 [M+H]$^+$.

Example 82

(S)-1-[5-Chloro-1-(4-cyanobenzenesulfonyl)-3-(2-methoxy-4-piperazin-1-ylmethyl-phenyl)-2-oxo-2,3-dihydro-1H-indol-3-yl]pyrrolidine-2-dimethylcarboxamide, Trifluoroacetic Acid Salt MS (API-ES, pos) m/z=677 [M+H]$^+$.

Example 83

(S)-1-[5-Chloro-1-(4-methoxybenzenesulfonyl)-3-(2-methoxy-4-piperidin-1-ylmethyl-phenyl)-2-oxo-2,3-dihydro-1H-indol-3-yl]pyrrolidine-2-dimethylcarboxamide, Trifluoroacetic Acid Salt MS (API-ES, pos) m/z=681 [M+H]$^+$.

Example 84

(S)-1-[5-Chloro-3-{4-[(ethylmethylamino)methyl]-2-methoxyphenyl}-1-(4-methoxy-benzenesulfonyl)-2-oxo-2,3-dihydro-1H-indol-3-yl]pyrrolidine-2-dimethylcarboxamide, Trifluoroacetic Acid Salt MS (API-ES, pos) m/z=655 [M+H]$^+$.

Example 85

(S)-1-[5-Chloro-1-(4-methoxybenzenesulfonyl)-3-(2-methoxy-4-propylaminomethyl-phenyl)-2-oxo-2,3-dihydro-1H-indol-3-yl]pyrrolidine-2-dimethylcarboxamide, Trifluoroacetic Acid Salt MS (API-ES, pos) m/z=655 [M+H]$^+$.

Example 86

(S)-1-[5-Chloro-3-(4-diethylaminomethyl-2-methoxyphenyl)-1-(4-methoxybenzene-sulfonyl)-2-oxo-2,3-dihydro-1H-indol-3-yl]pyrrolidine-2-dimethylcarboxamide, trifluoroacetic Acid Salt MS (API-ES, pos) m/z=669 [M+H]$^+$.

Example 87

(S)-1-[3-(4-Azetidin-1-ylmethyl-2-methoxyphenyl)-5-chloro-1-(4-methoxybenzene-sulfonyl)-2-oxo-2,3-dihydro-1H-indol-3-yl]pyrrolidine-2-dimethylcarboxamide, Trifluoroacetic Acid Salt MS (API-ES, pos) m/z=653 [M+H]$^+$.

Example 88

(S)-1-[5-Chloro-3-{4-[(isopropylmethylamino)methyl]-2-methoxyphenyl}-1-(4-methoxy-benzene-sulfonyl)-2-oxo-2,3-dihydro-1H-indol-3-yl]pyrrolidine-2-dimethylcarboxamide, Trifluoroacetic Acid Salt MS (API-ES, pos) m/z=669 [M+H]$^+$.

Example 89

(S)-1-[5-Chloro-1-(4-methoxybenzenesulfonyl)-3-(2-methoxy-4-{[(2-methoxyethyl)-methylamino]methyl}phenyl)-2-oxo-2,3-dihydro-1H-indol-3-yl]pyrrolidine-2-dimethylcarboxamide, Trifluoroacetic Acid Salt MS (API-ES, pos) m/z=685 [M+H]$^+$.

Example 90

(S)-1-[3-(4-Dimethylaminomethyl-2-methoxyphenyl)-1-(4-methoxybenzenesulfonyl)-2-oxo-2,3-dihydro-1H-indol-3-yl]pyrrolidine-2-dimethylcarboxamide, Trifluoroacetic Acid Salt MS (API-ES, pos) m/z=607 [M+H]$^+$.

Example 91

(S)-1-[1-(4-Methoxybenzenesulfonyl)-3-(2-methoxy-4-pyrrolidin-1-ylmethylphenyl)-2-oxo-2,3-dihydro-1H-indol-3-yl]pyrrolidine-2-dimethylcarboxamide, Trifluoroacetic Acid Salt MS (API-ES, pos) m/z=633 [M+H]$^+$.

Example 92

(S)-1-{1-(4-Methoxybenzenesulfonyl)-3-[2-methoxy-4-(4-methylpiperazin-1-yl-methyl)phenyl]-2-oxo-2,3-dihydro-1H-indol-3-yl}-pyrrolidine-2-carboxylic Acid Dimethylamide, Trifluoroacetic Acid Salt MS (API-ES, pos) m/z=662 [M+H]$^+$.

Example 93

(S)-1-[5-Chloro-3-(4-ethylaminomethyl-2-methoxyphenyl)-1-(4-methoxybenzene-sulfonyl)-2-oxo-2,3-dihydro-1H-indol-3-yl]pyrrolidine-2-dimethylcarboxamide, Trifluoroacetic Acid Salt MS (API-ES, pos) m/z=641 [M+H]$^+$.

Example 94

(S)-1-[5-Chloro-3-[4-(isopropylaminomethyl)-2-methoxyphenyl]-1-(4-methoxybenzene-sulfonyl)-2-oxo-2,3-dihydro-1H-indol-3-yl]pyrrolidine-2-dimethylcarboxamide, Trifluoroacetic Acid Salt MS (API-ES, pos) m/z=655 [M+H]$^+$.

Example 95

(S)-1-[5-Chloro-1-(4-cyanobenzenesulfonyl)-3-(5-dimethylaminomethyl-2-methoxy-phenyl)-2-oxo-2,3-dihydro-1H-indol-3-yl]pyrrolidine-2-dimethylcarboxamide MS (API-ES, pos) m/z=636 [M+H]$^+$.

Example 96

(S)-1-[5-Chloro-1-(4-cyanobenzenesulfonyl)-3-(2-methoxy-5-pyrrolidin-1-ylmethyl-phenyl)-2-oxo-2,3-dihydro-1H-indol-3-yl]pyrrolidine-2-dimethylcarboxamide MS (API-ES, pos) m/z=662 [M+H]$^+$.

Example 97

(S)-1-{5-Chloro-1-(4-cyanobenzenesulfonyl)-3-[2-methoxy-5-(4-methylpiperazin-1-yl-methyl)phenyl]-2-oxo-2,3-dihydro-1H-indol-3-yl}pyrrolidine-2-carboxylic Acid Dimethylamide, Trifluoroacetic Acid Salt MS (API-ES, pos) m/z=691 [M+H]$^+$.

Example 98

(S)-1-[5-Chloro-3-(5-dimethylaminomethyl-2-methoxyphenyl)-1-(4-fluorobenzene-sulfonyl)-2-oxo-2,3-dihydro-1H-indol-3-yl]pyrrolidine-2-dimethylcarboxamide, Trifluoroacetic Acid Salt MS (API-ES, pos) m/z=629 [M+H]$^+$.

Example 99

(S)-1-[5-Chloro-1-(4-cyanobenzenesulfonyl)-3-(2-methoxy-4-piperazin-1-ylmethyl-phenyl)-2-oxo-2,3-dihydro-1H-indol-3-yl]pyrrolidine-2-dimethylcarboxamide, Trifluoroacetic Acid Salt MS (API-ES, pos) m/z=677 [M+H]$^+$.

Example 100

(S)-1-[5-Chloro-1-(4-cyanobenzenesulfonyl)-3-(2-methoxy-5-propylaminomethyl-phenyl)-2-oxo-2,3-dihydro-1H-indol-3-yl]pyrrolidine-2-dimethylcarboxamide, Trifluoroacetic acid Salt MS (API-ES, pos) m/z=650 [M+H]$^+$.

Example 101

(S)-1-[5-Chloro-1-(4-cyanobenzenesulfonyl)-3-(5-isopropylaminomethyl-2-methoxy-phenyl)-2-oxo-2,3-dihydro-1H-indol-3-yl]pyrrolidine-2-dimethylcarboxamide, Trifluoroacetic Acid Salt MS (API-ES, pos) m/z=650 [M+H]$^+$.

Example 102

(S)-1-[5-Chloro-1-(4-cyanobenzenesulfonyl)-3-(2-methoxy-5-methylaminomethyl-phenyl)-2-oxo-2,3-dihydro-1H-indol-3-yl]pyrrolidine-2-dimethylcarboxamide, Trifluoroacetic Acid Salt MS (API-ES, pos) m/z=622 [M+H]$^+$.

Methods for Determining the Biological Activity

Vasopressin V1b Receptor Binding Assay:

Substances:

The test substances were dissolved in a concentration of $10^{-2}$ M in DMSO (dimethyl sulfoxide) and further diluted to $5\times10^{-4}$ M to $5\times10^{-9}$ M in DMSO. This series of DMSO predilutions was diluted 1:10 with assay buffer. The substance concentration was again diluted 1:5 in the assay mixture (2% DMSO in the mixture).

Membrane Preparation:

CHO-K1 cells with stably expressed human vasopressin V1b receptor (clone 3H2) were harvested and homogenized in 50 mM Tris-HCl and in the presence of protease inhibitors (Roche complete Mini #1836170) with a Polytron homogenizer at a medium setting for 2×10 seconds and subsequently centrifuged at 40 000×g for 1 h. The membrane pellet was again homogenized and centrifuged as described and then taken up in 50 mM Tris-HCl, pH 7.4, homogenized and stored in aliquots frozen in liquid nitrogen at −190° C.

Binding Assay:

The binding assay was carried out by a method based on that of Tahara et al. (Tahara A et al., Brit. J. Pharmacol. 125, 1463-1470 (1998)). The incubation buffer was: 50 mM Tris, 10 mM MgCl$_2$, 0.1% BSA, pH 7.4.

In the assay mixture (250 µl), membranes (50 µg/ml protein in incubation buffer) from CHO-K1 cells with stably expressed human V1b receptors (cell line hV1b__3H2_CHO) were incubated with 1.5 nM $^3$H-AVP (8-Arg-vasopressin, PerkinElmer #18479) in incubation buffer (50 mM Tris, 10 mM MgCl$_2$, 0.1% BSA, pH 7.4) (total binding) or additionally with increasing concentrations of test substance (displacement experiment). The nonspecific binding was determined with 1 uM AVP (Bachem # H1780). All determinations were carried out as triplicate determinations. After incubation (60 minutes at room temperature), the free radioligand was removed by vacuum filtration (Skatron cell harvester 7000) through Whatman GF/B glass fiber filter mats, and the filters were transferred into scintillation vials. The liquid scintillation measurement took place in a Tricarb model 2000 or 2200CA instrument (Packard). Conversion of the measured cpm into dpm was carried out with the aid of a standard quench series.

Evaluation:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^3$H-AVP for the recombinant hV2 receptors is 0.4 nM and was used to determine the Ki value.

Vasopressin V1a Receptor Binding Assay:

Substances:

The test substances were dissolved in a concentration of $10^{-2}$ M in DMSO. These DMSO solutions were further diluted in incubation buffer (50 mM Tris, 10 mM MgCl$_2$, 0.1% BSA, pH 7.4).

Membrane Preparation:

CHO-K1 cells with stably expressed human vasopressin V1a receptor (clone 5) were harvested and homogenized in 50 mM Tris-HCl and in the presence of protease inhibitors (Roche complete Mini #1836170) with a Polytron homogenizer at a medium setting for 2×10 seconds and subsequently centrifuged at 40 000×g for 1 h. The membrane pellet was again homogenized and centrifuged as described and then taken up in 50 mM Tris-HCl, pH 7.4, homogenized and stored in aliquots frozen in liquid nitrogen at −190° C.

Binding Assay:

The binding assay was carried out by a method based on that of Tahara et al. (Tahara A et al., Brit. J. Pharmacol. 125, 1463-1470 (1998)).

The incubation buffer was: 50 mM Tris, 10 mM MgCl$_2$, 0.1% BSA, pH 7.4. In the assay mixture (250 µl), membranes (20 µg/ml protein in incubation buffer) from CHO-K1 cells with stably expressed human V1a receptors (cell line hV1a-5-CHO) were incubated with 0.04 nM $^{125}$I-AVP (8-Arg-vasopressin, NEX 128) in incubation buffer (50 mM Tris, 10 mM MgCl$_2$, 0.1% BSA, pH 7.4) (total binding) or additionally with increasing concentrations of test substance (displacement experiment). The nonspecific binding was determined with 1 µM AVP (Bachem # H1780). Triplicate determinations were carried out.

After incubation (60 minutes at room temperature), the free radioligand was removed by vacuum filtration (Skatron cell harvester 7000) through Whatman GF/B glass fiber filter mats, and the filters were transferred into scintillation vials. The liquid scintillation measurement took place in a Tricarb model 2000 or 2200CA instrument (Packard). Conversion of the measured cpm into dpm was carried out with the aid of a standard quench series.

Evaluation:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^{125}$I-AVP for the recombinant hV1a receptors was determined in saturation experiments. A Kd of 1.33 nM was used to determine the Ki value.

Vasopressin V2 Receptor Binding Assay:

Substances:

The test substances were dissolved in a concentration of $10^{-2}$ M in DMSO. These DMSO solutions were further diluted in incubation buffer (50 mM Tris, 10 mM MgCl$_2$, 0.1% BSA, pH 7.4).

Membrane Preparation:

CHO-K1 cells with stably expressed human vasopressin V2 receptor (clone 23) were harvested and homogenized in 50 mM Tris-HCl and in the presence of protease inhibitors (Roche complete Mini #1836170) with a Polytron homogenizer at a medium setting for 2×10 seconds and subsequently centrifuged at 40 000×g for 1 h. The membrane pellet was again homogenized and centrifuged as described and then taken up in 50 mM Tris-HCl, pH 7.4, homogenized and stored in aliquots frozen in liquid nitrogen at −190° C.

Binding Assay:

The binding assay was carried out by a method based on that of Tahara et al. (Tahara A et al., Brit. J. Pharmacol. 125, 1463-1470 (1998)).

The incubation buffer was: 50 mM Tris, 10 mM $MgCl_2$, 0.1% BSA, pH 7.4. In the assay mixture (250 µl), membranes (50 µg/ml protein in incubation buffer) from CHO-K1 cells with stably expressed human V2 receptors (cell line hV2-23-CHO) were incubated with 1-2 nM $^3$H-AVP (8-Arg-vasopressin, PerkinElmer #18479) in incubation buffer (50 mM Tris, 10 mM $MgCl_2$, 0.1% BSA, pH 7.4) (total binding) or additionally with increasing concentrations of test substance (displacement experiment). The nonspecific binding was determined with 1 µM AVP (Bachem # H1780). Triplicate determinations were carried out.

After incubation (60 minutes at room temperature), the free radioligand was removed by vacuum filtration (Skatron cell harvester 7000) through Whatman GF/B glass fiber filter mats, and the filters were transferred into scintillation vials. The liquid scintillation measurement took place in a Tricarb model 2000 or 2200CA instrument (Packard). Conversion of the measured cpm into dpm was carried out with the aid of a standard quench series.

Evaluation:

The binding parameters were calculated by nonlinear regression in SAS. The algorithms of the program operate in analogy to the LIGAND analysis program (Munson P J and Rodbard D, Analytical Biochem. 107, 220-239 (1980)). The Kd of $^3$H-AVP for the recombinant hV2 receptors is 2.4 nM and was used to determine the Ki value.

Oxytocin Receptor Binding Assay

Substances:

The substances were dissolved in a concentration of $10^{-2}$ m in DMSO and diluted with incubation buffer (50 mM Tris, 10 mM $MgCl_2$, 0.1% BSA, pH 7.4).

Cell Preparation:

Confluent HEK-293 cells with transiently expressing recombinant human oxytocin receptors were centrifuged at 750×g and at room temperature for 5 minutes. The residue was taken up in ice-cold lysis buffer (50 mM Tris-HCl, 10% glycerol, pH7.4 and Roche Complete Protease Inhibitor) and subjected to an osmotic shock at 4° C. for 20 minutes. The lysed cells were then centrifuged at 750×g and at 4° C. for 20 minutes, the residue was taken up in incubation buffer, and aliquots of $10^7$ cells/ml were prepared. The aliquots were frozen at −80° C. until used.

Binding Assay:

On the day of the experiment, the cells were thawed, diluted with incubation buffer and homogenized using a Multipette Combitip (Eppendorf, Hamburg). The reaction mixture of 0.250 ml was composed of 2 to 5×$10^4$ recombinant cells, 3-4 nM $^3$H-oxytocin (PerkinElmer, NET 858) in the presence of test substance (inhibition plot) or only incubation buffer (total binding). The nonspecific binding was determined with $10^{-6}$ M oxytocin (Bachem AG, H2510). Determinations in triplicate were set up. Bound and free radioligand were separated by filtration under vacuum with Whatmann GF/B glass fiber filters using a Skatron cell harvester 7000. The bound radioactivity was determined by liquid scintillation measurement in a Tricarb beta counter, model 2000 or 2200CA (Packard).

Evaluation:

The binding parameters were calculated by nonlinear regression analysis (SAS), in analogy to the LIGAND program of Munson and Rodbard (Analytical Biochem 1980; 107: 220-239). The Kd of $^3$H-oxytocin for the recombinant hOT receptors is 7.6 nM and was used to determine the Ki value.

Effect on Vasopressin-Induced Calcium Increase in Cells Having a Cloned Human Vasopressin Receptor The functional activity of the test substances was investigated on CHO-K1 cells which were stably transfected with the human V1b receptor. 50 000 cells were seeded in each well of a microtiter plate with 96 wells and incubated in culture medium in a saturated water vapor atmosphere with 5% $CO_2$ at 37° C. overnight. The culture medium consisted of DMEM/Nut Mix F12 with Glutamax I (from Invitrogen), 10% fetal calf serum, 100 units/ml penicillin, 100 µg/ml streptomycin and 800 µg/ml Geneticin. The following day, the cells were washed with culture medium and loaded with a fluorescent dye for calcium in accordance with the manufacturer's statements ($Ca^{++}$-Plus-Assay Kit, Molecular Devices). The cells were loaded in the presence of probenzide (1 vol %). The test substances were diluted with culture medium (final concentration $10^{-10}$ to $10^{-5}$M) and incubated with the dye-loaded cells at room temperature for 15 minutes. The Arg-vasopressin ($10^{-8}$M) was then added and the maximum fluorescence signal was determined using a FLIPR-96 measuring instrument (Molecular Devices). Concentration-effect plots were constructed using nonlinear regression algorithms (GraphPad Prism 3.0). Kb values were calculated from IC50 values by the method of Cheng and Prusoff (Kb=IC50/1+L/EC50).

The affinities of the compounds (I) of the invention for the human vasopressin V1b receptor were measured in accordance with the above assays, and the affinity constants (Ki) were determined. Table 1 below details the V1b receptor affinity of selected compounds (+++means<1 nM, ++ means 1-10 nM and +means 10-100 nM).

TABLE 1

| Example | V1b Ki |
| --- | --- |
| 1 | +++ |
| 2 | +++ |
| 3 | ++ |
| 4 | +++ |
| 5 | +++ |
| 6 | + |
| 7 | ++ |
| 8 | ++ |
| 9 | ++ |
| 10 | + |
| 11 | + |
| 12 | ++ |
| 13 | ++ |
| 14 | ++ |
| 15 | +++ |
| 16 | ++ |
| 17 | +++ |
| 18 | +++ |
| 19 | +++ |

TABLE 1-continued

| Example | V1b Ki |
|---------|--------|
| 20 | +++ |
| 21 | +++ |
| 22 | +++ |
| 23 | +++ |
| 24 | +++ |
| 25 | +++ |
| 26 | +++ |
| 27 | +++ |
| 28 | ++ |
| 29 | +++ |
| 30 | +++ |
| 31 | ++ |
| 32 | +++ |
| 33 | +++ |
| 69 | +++ |
| 70 | +++ |
| 71 | +++ |
| 72 | ++ |
| 73 | ++ |
| 74 | +++ |
| 75 | + |
| 76 | ++ |
| 77 | + |
| 78 | +++ |
| 79 | +++ |
| 80 | +++ |
| 81 | ++ |
| 82 | +++ |
| 83 | +++ |
| 84 | +++ |
| 85 | +++ |
| 86 | +++ |
| 87 | +++ |
| 88 | +++ |
| 89 | +++ |
| 90 | + |
| 91 | ++ |
| 92 | ++ |
| 93 | +++ |
| 94 | +++ |
| 95 | ++ |
| 96 | +++ |
| 97 | +++ |
| 98 | ++ |
| 99 | +++ |
| 100 | +++ |
| 101 | +++ |
| 102 | ++ |

It is additionally possible in accordance with the above assays to determine the affinities for further vasopressin receptors or their subtypes such as, for example, V1a and V2, and the oxytocin (OT) receptor. The quotients obtainable thereby for the corresponding Ki values, i.e. "Ki(V1a)/Ki(V1b)", "Ki(V2)/Ki(v1b)" and/or "Ki(OT)Ki(V1b)", may serve as a measure of a possible selectivity of the compounds of the invention in relation to a particular vasopressin or oxytocin receptor or one of their subtypes such as, for example, V1b.

The compounds of the invention showed a surprisingly high affinity for the human V1b receptor, frequently less than or equal to 1 nM and in some cases even less than or equal to 0.1 nM. A number of compounds of the invention act as functional antagonist of the human vasopressin V1b receptor, e.g. Example 2. Because of the greatly raised affinity of the compounds of the invention for the human V1b receptor, they will elicit even at relatively low concentrations/effective levels the therapeutic effects mediated by V1b receptors. Low effective levels are generally desired because the probability of side effects which are not elicited by the interaction with human V1b receptors is lower thereby.

The invention claimed is:

1. A compound of the formula (I),

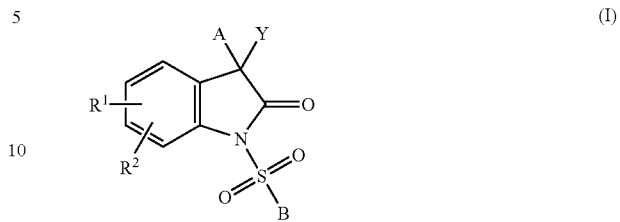

in which

A is an aromatic, heteroaromatic, partly aromatic or partly heteroaromatic mono- or bicyclic radical which consists of 2, 3, 4, 5, 6, 7, 8, 9 or 10 carbon atoms and 0, 1, 2, 3 or 4 nitrogen atoms and/or 0, 1 or 2 oxygen atoms and/or 0, 1 or 2 sulfur atoms, and which is substituted by the radical $R_A^1$ and may be additionally substituted by 1, 2 or 3 radicals $R_A^{11}$, $R_A^{12}$ and/or $R_A^{13}$ which are selected independently of one another and independent of their respective occurrence from the group consisting of hydrogen, chlorine, bromine, iodine, fluorine, CN, $CF_3$, $OCF_3$, $OCHF_2$, CO—$NH_2$, CO—NH($C_1$-$C_4$-alkyl), CO—N($C_1$-$C_4$-alkyl)($C_1$-$C_4$-alkyl), $NH_2$, NH($C_1$-$C_4$-alkyl), N($C_1$-$C_4$-alkyl)($C_1$-$C_4$-alkyl), NHCHO, NH—CO—$NH_2$, NH—CO($C_1$-$C_4$-alkyl), $NO_2$, OH, O—$C_1$-$C_4$-alkyl, O—$C_0$-$C_4$-alkylene-phenyl, phenyl, $C_1$-$C_6$-alkyl, $C_1$-$C_6$-haloalkyl, $C_2$-$C_6$-alkenyl and $C_2$-$C_6$-alkynyl, in which $R_A^1$ is $R_A^2$—($C_1$-$C_4$-alkylene)-$R_A^4$, $R_A^2$ is selected from the group consisting of ($C_0$-$C_4$-alkylene)-O, ($C_0$-$C_4$-alkylene)-$NR_A^5$, ($C_0$-$C_4$-alkylene)-S, ($C_0$-$C_4$-alkylene)-SO, ($C_0$-$C_4$-alkylene)-$SO_2$, ($C_0$-$C_4$-alkylene)-CO, ($C_0$-$C_4$-alkylene)-$NR_A^5$—$SO_2$, ($C_0$-$C_4$-alkylene)-CO—$NR_A^5$, ($C_0$-$C_4$-alkylene)-CO—O, ($C_0$-$C_4$-alkylene)-$NR_A^5$—$SO_2$, ($C_0$-$C_4$-alkylene)-$SO_2$—$NR_A^5$, ($C_0$-$C_4$-alkylene)-$NR_A^5$—CO—$NR_A^6$, ($C_0$-$C_4$-alkylene)-O—CO—$NR_A^5$, ($C_0$-$C_4$-alkylene)-$NR_A^5$—CO—O and single bond, $R_A^4$ is selected from the group consisting of $NH_2$, NH($C_1$-$C_4$-alkyl), N($C_1$-$C_4$-alkyl)($C_1$-$C_4$-alkyl), NH($C_1$-$C_4$-alkylene-O—$C_1$-$C_4$-alkyl), N($C_1$-$C_4$-alkyl)($C_1$-$C_4$-alkylene-O—$C_1$-$C_4$-alkyl), NH—CHO, N($C_1$-$C_4$-alkyl)-CHO, NH—CO—$NH_2$, N($C_1$-$C_4$-alkyl)-CO—$NH_2$, NH—CO—$C_1$-$C_4$-alkyl, N($C_1$-$C_4$-alkyl)-CO—$C_1$-$C_4$-alkyl, NH—$SO_2$—$C_1$-$C_4$-alkyl, N($C_1$-$C_4$-alkyl)-$SO_2$—$C_1$-$C_4$-alkyl and ring $R_A^8$, $R_A^5$, $R_A^6$, $R_A^9$ are selected independently of one another and independent of their respective occurrence from the group consisting of hydrogen, $C_1$-$C_4$-alkyl and $C_1$-$C_4$-haloalkyl;

$R_A^8$ is selected from the group consisting of the respective individual radicals

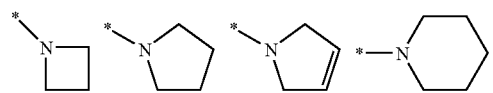

-continued

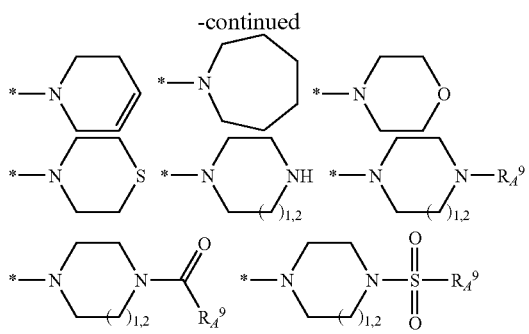

B is an aromatic, heteroaromatic, partly aromatic or partly heteroaromatic mono- or bicyclic radical which consists of 2, 3, 4, 5, 6, 7, 8, 9 or 10 carbon atoms and 0, 1, 2, 3 or 4 nitrogen atoms and/or 0, 1 or 2 oxygen atoms and/or 0, 1 or 2 sulfur atoms, and which may be substituted by 1, 2 or 3 radicals $R_B^1$, $R_B^2$ and/or $R_B^3$, where $R_B^1$, $R_B^2$ and $R_B^3$ are selected independently of one another and independent of their respective occurrence from the group consisting of hydrogen, chlorine, bromine, iodine, fluorine, CN, $CF_3$, $OCF_3$, $OCHF_2$, $CO-NH_2$, $CO-NH(C_1-C_4$-alkyl), $CO-N(C_1-C_4$-alkyl)$(C_1-C_4$-alkyl), $NH_2$, $NH(C_1-C_4$-alkyl), $N(C_1-C_4$-alkyl)$(C_1-C_4$-alkyl), $NH-CHO$, $NH-CO-NH_2$, $NH-CO-C_1-C_4$-alkyl, $NO_2$, OH, $O-C_1-C_4$-alkyl, $O-C_0-C_4$-alkylenephenyl, phenyl, $C_1-C_6$-alkyl, $C_1-C_6$-haloalkyl, $C_2-C_6$-alkenyl and $C_2-C_6$-alkynyl;

$R^1$ is selected from the group consisting of hydrogen, chlorine, bromine, iodine, fluorine, CN, $CF_3$, $OCF_3$, $OCHF_2$, $CO-NH_2$, $CO-NH(C_1-C_4$-alkyl), $CO-N(C_1-C_4$-alkyl)$(C_1-C_4$-alkyl), $NH_2$, $NH(C_1-C_4$-alkyl), $N(C_1-C_4$-alkyl)$(C_1-C_4$-alkyl), $NH-CHO$, $NH-CO-NH_2$, $NH-CO-C_1-C_4$-alkyl, $NO_2$, OH, $O-C_1-C_4$-alkyl, $O-C_0-C_4$-alkylenephenyl, phenyl, $C_1-C_6$-alkyl, $C_1-C_6$-haloalkyl, $C_2-C_6$-alkenyl and $C_2-C_6$-alkynyl, $R^2$ is selected from the group consisting of hydrogen, $C_1-C_4$-alkyl, $O-C_1-C_4$-alkyl, chlorine and fluorine, Y is a radical

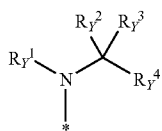

in which $R_Y^1$ is selected from the group consisting of hydrogen, $C_1-C_4$-alkyl and $C_1-C_4$-haloalkyl;

$R_Y^2$ is selected from the group consisting of hydrogen; phenyl; phenyl substituted by 1, 2, 3, 4 or 5 radicals $R_{Ph}^1$, $R_{Ph}^2$, $R_{Ph}^3$, $R_{Ph}^4$ and/or $R_{Ph}^5$ which are selected independently of one another from the group consisting of hydrogen, halogen, $C_1-C_6$-alkyl and $C_1-C_6$-alkoxy; $C_1-C_6$-alkyl; $C_3-C_7$-cycloalkyl and $C_1-C_6$-haloalkyl;

in which $R_Y^1$ and $R_Y^2$ may also form together with the atoms to which they are bonded a 4-, 5-, 6- or 7-membered, saturated or unsaturated ring which may, instead of a ring C atom, also include a heteroatom selected from the group consisting of O, S and $NR_Y^5$ as further ring member, where $R_Y^5$ independent of its respective occurrence is hydrogen, $C_1-C_4$-alkyl or $CO-C_1-C_4$-alkyl, and where the ring may have one or two substituents $R_Y^6$ and $R_Y^7$ which are selected independently of one another and independent of their respective occurrence from the group consisting of the radicals hydrogen, chlorine, bromine, iodine, fluorine, CN, $CF_3$, $OCF_3$, $OCHF_2$, $CO-NH_2$, $CO-NH(C_1-C_4$-alkyl), $CO-N(C_1-C_4$-alkyl)$(C_1-C_4$-alkyl), $NH_2$, $NH(C_1-C_4$-alkyl), $N(C_1-C_4$-alkyl)$(C_1-C_4$-alkyl), $NH-CHO$, $NH-CO-NH_2$, $NH-CO-C_1-C_4$-alkyl, OH, $O-C_1-C_4$-alkyl, $O-CO-C_1-C_4$-alkyl, $O-(CH_2)_{0-2}$-phenyl, phenyl, $C_1-C_6$-alkyl, or $R_Y^6$ and $R_Y^7$ may also independent of their respective occurrence form together with the C atoms to which they are bonded a fused phenyl ring or a fused 5- or 6-membered, aromatic heterocycle which, besides C atoms, includes as ring members 1, 2, 3 or 4 identical or different heteroatoms as ring members which may be selected independently of one another from the group consisting of nitrogen, oxygen and sulfur, $R_Y^3$ is selected from the group consisting of hydrogen, $C_1-C_4$-alkyl and $C_1-C_4$-haloalkyl;

$R_Y^4$ is selected from the group consisting of hydrogen, $CO-NR_Y^{21}R_Y^{22}$, $CO-C_1-C_4$-alkyl, COOH and $CO-O-C_1-C_4$-alkyl, $R_Y^{21}$, $R_Y^{22}$ are selected independently of one another and independent of their respective occurrence from the group consisting of hydrogen, $C_1-C_4$-alkyl and $C_1-C_4$-haloalkyl;

or $R_Y^{21}$ and $R_Y^{22}$ may also independent of their respective occurrence form together with the nitrogen atom to which they are bonded a 4-, 5- or 6-membered, saturated or wholly or partly unsaturated N-heterocyclic ring, the tautomeric, enantiomeric and diastereomeric forms thereof and the physiologically tolerated salts of said compound.

2. A compound of the formula (I) as claimed in claim 1, in which

A is an aromatic or heteroaromatic monocyclic radical having 2, 3, 4, 5, 6, 7, 8, 9 or 10 carbon atoms as ring members, which may besides comprise additionally 0, 1, 2 or 3 identical or different heteroatoms independently of one another selected from the group consisting of nitrogen, oxygen and sulfur, as ring members, and is substituted by the radical $R_A^1$ and may besides be substituted by one, two or three radicals $R_A^{11}$, $R_A^{12}$ and/or $R_A^{13}$ which are selected independently of one another and independent of their respective occurrence from the group consisting of hydrogen, chlorine, fluorine, $O-C_1-C_4$-alkyl, $C_1-C_4$-alkyl and $C_1-C_4$-haloalkyl, in which $R_A^1$ is $R_A^2-(C_1-C_4$-alkylene)-$R_A^4$;

$R_A^2$ is selected from the group consisting of $(C_0-C_4$-alkylene)-O, $(C_0-C_4$-alkylene)-$NR_A^5$, $(C_0-C_4$-alkylene)-S, $(C_0-C_4$-alkylene)-SO, $(C_0-C_4$-alkylene)-$SO_2$, $(C_0-C_4$-alkylene)-CO, $(C_0-C_4$-alkylene)-$NR_A^5$—CO, $(C_0-C_4$-alkylene)-CO—$NR_A^5$, $(C_0-C_4$-alkylene)-CO—O and single bond;

$R_A^4$ is selected from the group consisting of $NH_2$, $NH(C_1-C_4$-alkyl), $N(C_1-C_4$-alkyl)$(C_1-C_4$-alkyl), $N(C_1-C_4$-alkyl)$(C_1-C_4$-alkylene-O—$C_1-C_4$-alkyl) and ring $R_A^8$;

$R_A^5$, $R_A^9$ are selected independently of one another and independent of their respective occurrence from the group consisting of hydrogen and $C_1-C_4$-alkyl;

$R_A^8$ is selected independent of its respective occurrence from the group consisting of the respective individual radicals

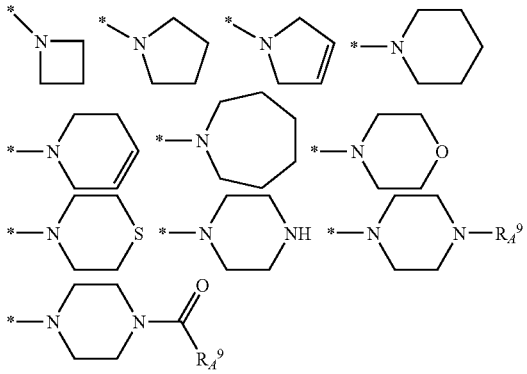

B is an aromatic or heteroaromatic mono- or bicyclic radical having 2, 3, 4, 5, 6, 7, 8, 9 or 10 C atoms as ring members, which may additionally comprise 1, 2 or 3 identical or different heteroatoms selected independently of one another from the group consisting of nitrogen, oxygen and sulfur as ring members, and which may be substituted by one, two or three radicals $R_B^1$, $R_B^2$ and/or $R_B^3$, where $R_B^1$, $R_B^2$ and $R_B^3$ are selected independently of one another and independent of their respective occurrence from the group consisting of hydrogen, chlorine, bromine, fluorine, CN, $CF_3$, $OCF_3$, $OCHF_2$, O—$C_1$-$C_4$-alkyl, $C_1$-$C_4$-alkyl and $C_1$-$C_4$-haloalkyl;

$R^1$ is selected from the group consisting of hydrogen, bromine, chlorine, fluorine, CN, $CF_3$, $OCF_3$, O—$C_1$-$C_4$-alkyl, $C_1$-$C_4$-alkyl, $C_1$-$C_4$-haloalkyl and $C_2$-$C_4$-alkynyl, $R^2$ is selected from the group consisting of hydrogen, $C_1$-$C_4$-alkyl, $C_1$-$C_4$-haloalkyl, O—$C_1$-$C_4$-alkyl, chlorine and fluorine, Y is a radical

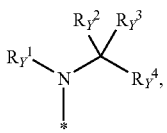

in which $R_Y^1$ is selected from the group consisting of hydrogen and $C_1$-$C_4$-alkyl;

$R_Y^2$ is selected from the group consisting of hydrogen, phenyl, $C_1$-$C_6$-alkyl, and $C_3$-$C_7$-cycloalkyl in which $R_Y^1$ and $R_Y^2$ may also form together with the atoms to which they are bonded a 4-, 5-, 6- or 7-membered, saturated or unsaturated ring which may, instead of a C atom as ring member, also include a hetero-atom selected from the group consisting of O and $NR_Y^5$, as further ring member, where $R_Y^5$ independent of its respective occurrence is hydrogen, $C_1$-$C_4$-alkyl, $C_1$-$C_4$-haloalkyl or CO—$C_1$-$C_4$-alkyl, and where the ring may have one or two substituents $R_Y^6$ and/or $R_Y^7$ which are selected independently of one another and independent of their respective occurrence from the group consisting of the radicals hydrogen, fluorine, CN, OH, O—$C_1$-$C_4$-alkyl, O—CO—$C_1$-$C_4$-alkyl, O—$(CH_2)_{0-2}$-phenyl, phenyl and $C_1$-$C_4$-alkyl; or $R_Y^6$ and $R_Y^7$ may independent of their respective occurrence also form together with the C atoms to which they are bonded a fused phenyl ring (benzo ring);

$R_Y^3$ is selected from the group consisting of hydrogen and methyl;

$R_Y^4$ is selected from the group consisting of CO—$NR_Y^{21}R_Y^{22}$, CO—$C_1$-$C_4$-alkyl and CO—O—$C_1$-$C_4$-alkyl;

$R_Y^{21}$, $R_Y^{22}$ are selected independently of one another and independent of their respective occurrence from the group consisting of hydrogen and $C_1$-$C_4$-alkyl; or $R_Y^{21}$ and $R_Y^{22}$ may independent of their respective occurrence also form together with the nitrogen atom to which they are bonded a 4-, 5- or 6-membered, saturated or unsaturated N-heterocyclic ring, the tautomeric, enantiomeric and diastereomeric forms thereof, and the physiologically tolerated salts of said compound.

3. A compound of the formula I as claimed in claim 1, in which

A is a cyclic radical which is selected from the group consisting of phenyl, thienyl, pyridyl, pyrimidinyl, pyrazinyl and pyridazinyl, and which is substituted by the radical $R_A^1$ and may besides be additionally substituted by one or two radicals $R_A^{11}$ and/or $R_A^{12}$ which are selected independently of one another and independent of their respective occurrence from the group consisting of hydrogen, chlorine, methoxy, ethoxy, propoxy, methyl, ethyl and propyl;

in which $R_A^1$ is $R_A^2$—($C_1$-$C_4$-alkylene)-$R_A^4$, in which $R_A^2$ is selected from the group consisting of O, $CH_2$—O, $NR_A^5$, $CH_2$—$NR_A^5$, $NR_A^5$—CO, $CH_2$—$NR_A^5$—CO and a single bond;

$R_A^4$ is selected from the group consisting of $NH_2$, $NH(C_1$-$C_4$-alkyl), $N(C_1$-$C_4$-alkyl) $(C_1$-$C_4$-alkyl), $N(C_1$-$C_4$-alkyl)$(C_1$-$C_4$-alkylene-O—$C_1$-$C_4$-alkyl) and ring $R_A^8$;

$R_A^5$, $R_A^9$ are selected independently of one another and independent of their respective occurrence from the group consisting of hydrogen and $C_1$-$C_4$-alkyl;

$R_A^8$ is selected from the group consisting of the respective individual radicals

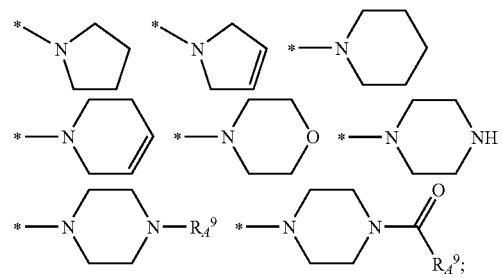

B is an aromatic or heteroaromatic mono- or bicyclic radical having 2, 3, 4, 5, 6, 7, 8, 9 or 10 C atoms as ring members, which may comprise 1, 2 or 3 identical or different heteroatoms selected independently of one another from the group consisting of nitrogen, oxygen and sulfur as ring member, and which may be substituted by one or two radicals $R_B^1$ and/or $R_B^2$, where $R_B^1$ and $R_B^2$ are selected independently of one another from the group consisting of hydrogen, chlorine, fluorine, CN, O—$C_1$-$C_4$-alkyl and $C_1$-$C_4$-alkyl;

$R^1$ is selected from the group consisting of hydrogen, chlorine, fluorine, CN, methoxy and methyl;

$R^2$ is selected from the group consisting of hydrogen, chlorine and methyl;

Y is a radical

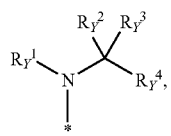

in which $R_Y^1$ is selected from the group consisting of hydrogen and $C_1$-$C_4$-alkyl;

$R_Y^2$ is selected from the group consisting of hydrogen, phenyl and $C_1$-$C_4$-alkyl;

where $R_Y^1$ and $R_Y^2$ may also form together with the atoms to which they are bonded a 5- or 6-membered, saturated or unsaturated ring which, instead of a C atom as ring member, may also include a heteroatom selected from the group consisting of O and $NR_Y^5$ as further ring member, where $R_Y^5$ independent of its respective occurrence is hydrogen, $C_1$-$C_4$-alkyl, or CO—$C_1$-$C_4$-alkyl, and where the ring may have one or two substituents $R_Y^6$ and/or $R_Y^7$ which are selected independently of one another and independent of their respective occurrence from the group consisting of the radicals hydrogen, fluorine, OH and O—$C_1$-$C_4$-alkyl, or $R_Y^6$ and $R_Y^7$ may independent of their respective occurrence also form together with the C atoms to which they are bonded a fused phenyl ring (benzo ring);

$R_Y^3$ is selected from the group consisting of hydrogen and methyl;

$R_Y^4$ is CO—$NR_Y^{21}R_Y^{22}$, in which $R_Y^{21}$, $R_Y^{22}$ are selected independently of one another from the group consisting of hydrogen and $C_1$-$C_4$-alkyl; or $R_Y^{21}$ and $R_Y^{22}$ may independent of their respective occurrence also form together with the nitrogen atom to which they are bonded a 4-, 5- or 6-membered, saturated or unsaturated N-heterocyclic ring;

the tautomeric, enantiomeric and diastereomeric forms thereof, and the physiologically tolerated salts of said compound.

4. A compound of the formula (I) as claimed in claim 1, in which

A is a radical selected from the group consisting of the respective individual radicals

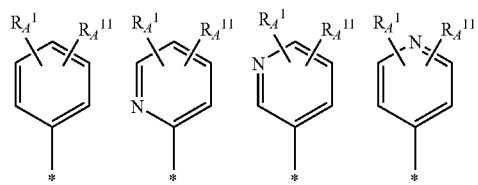

-continued

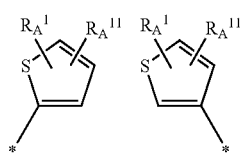

in which $R_A^{11}$ is selected independent of its respective occurrence from the group consisting of hydrogen, chlorine, methoxy and ethoxy;

$R_A^1$ is a radical selected from the group consisting of the respective individual radicals

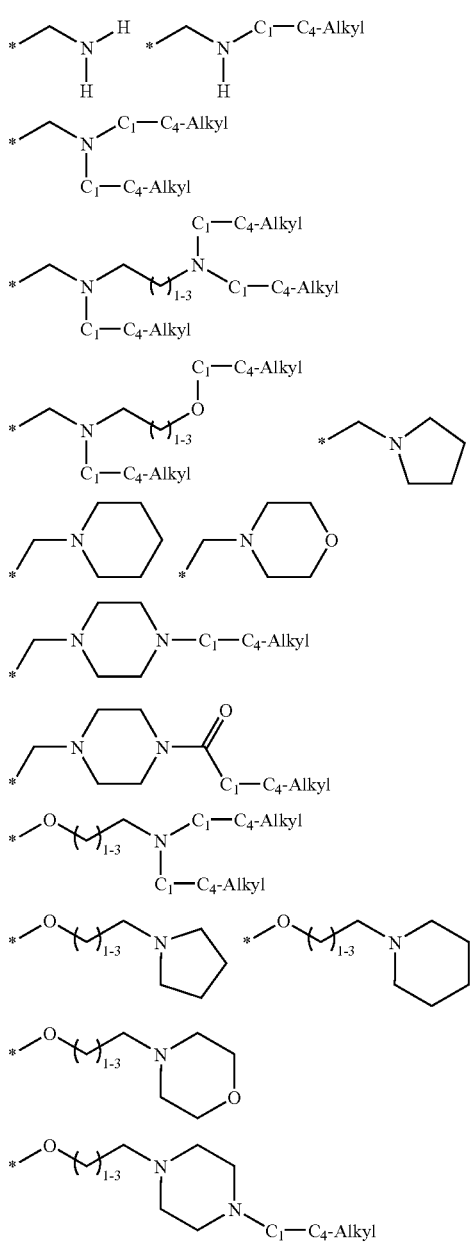

67

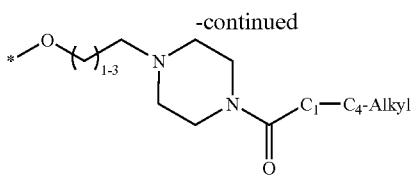

-continued

B is a cyclic radical selected from the group consisting of phenyl, pyridyl, thienyl and quinolinyl, which may in each case be substituted by 1 or 2 radicals $R_B^1$ and/or $R_B^2$, where $R_B^1$ and $R_B^2$ are selected independently of one another from the group consisting of hydrogen, chlorine, fluorine, CN, methyl and methoxy;

$R^1$ is selected from the group consisting of hydrogen, chlorine, fluorine, CN, methoxy and methyl;

$R^2$ is selected from the group consisting of hydrogen and chlorine;

Y is a radical selected from the group consisting of the respective individual radicals

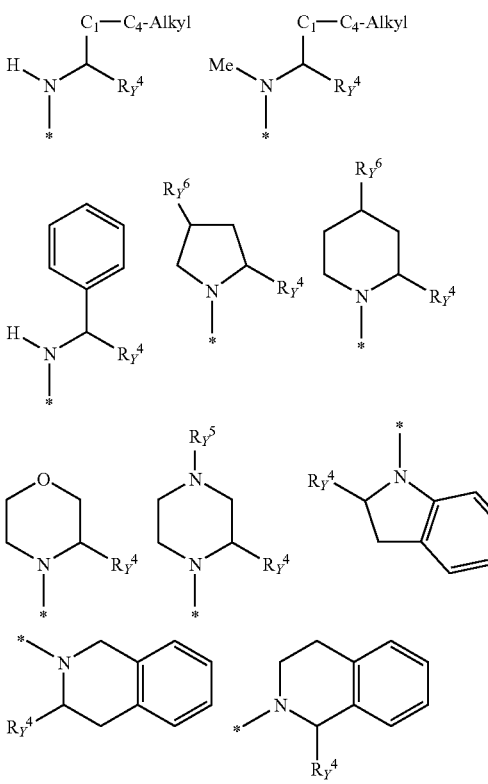

Me is $CH_3$ $R_Y^4$ is $CO-NR_Y^{21}R_Y^{22}$, where $R_Y^{21}$ and $R_Y^{22}$ are selected independently of one another from the group consisting of hydrogen, methyl and ethyl; or $R_Y^{21}$ and $R_Y^{22}$ may independent of their respective occurrence also form together with the nitrogen atom to which they are bonded a 4-, 5- or 6-membered, saturated or unsaturated or partly unsaturated N-heterocyclic ring;

$R_Y^5$ is selected from the group consisting of the radicals hydrogen, $C_1$-$C_4$-alkyl, and $CO-C_1$-$C_4$-alkyl;

$R_Y^6$ is selected from the group consisting of the radicals hydrogen, fluorine, OH and $O-C_1$-$C_4$-alkyl,

68 the tautomeric, enantiomeric and diastereomeric forms thereof, and the physiologically tolerated salts of said compound.

5. A compound of the formula (I) as claimed in claim 1, in which

A is selected from the group consisting of the respective individual radicals

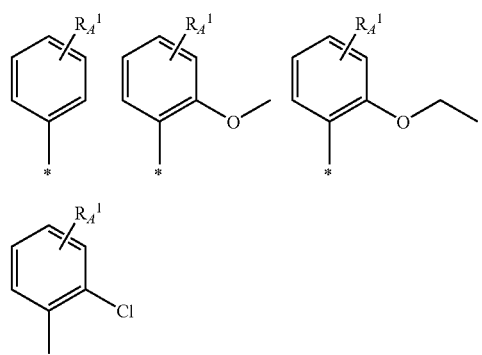

$R_A^1$ is a radical selected independent of its respective occurrence from the group consisting of the respective individual radicals

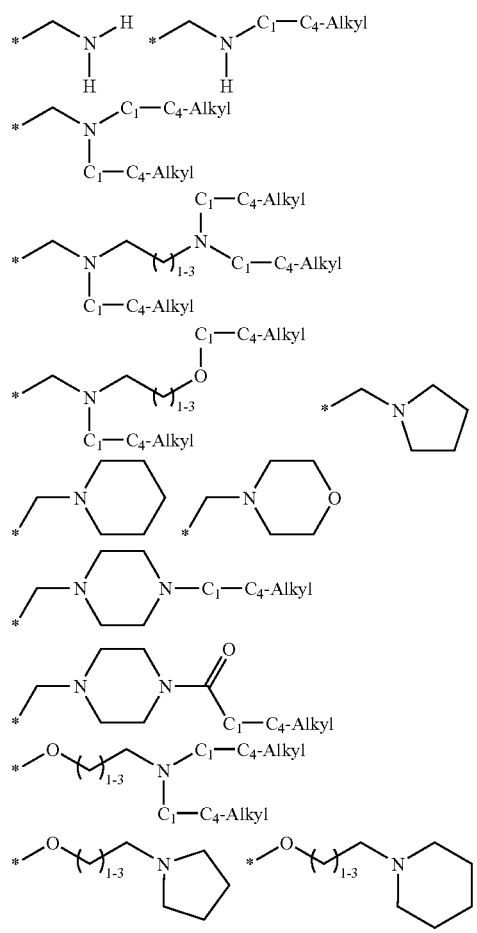

-continued

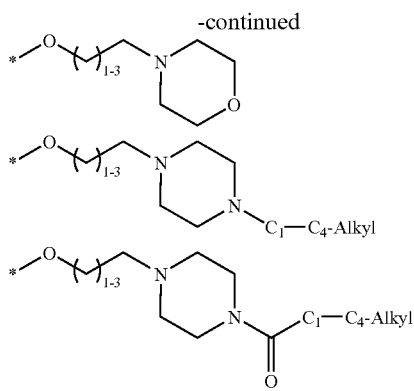

B is a cyclic radical selected from the group consisting of the respective individual radicals

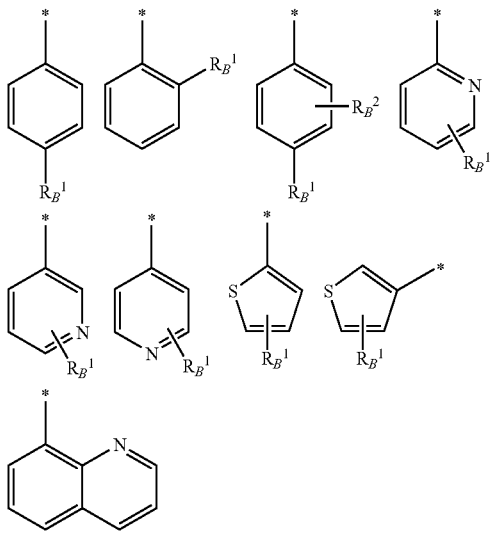

in which
R$_B^1$ and R$_B^2$ are selected independently of one another and independent of their respective occurrence from the group consisting of hydrogen, chlorine, fluorine, CN, methyl and methoxy;
R$^1$ is selected from the group consisting of chlorine, methoxy and CN;
R$^2$ is hydrogen;
Y is selected from the group consisting of the respective individual radicals

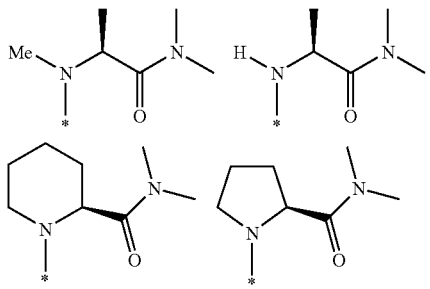

-continued

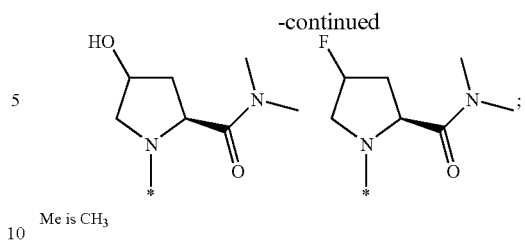

Me is CH$_3$ the tautomeric, enantiomeric and diastereomeric forms thereof, and the physiologically tolerated salts of said compound.

6. A compound of the formula (I) as claimed in claim 1, in which

A is selected from the group consisting of the respective individual radicals

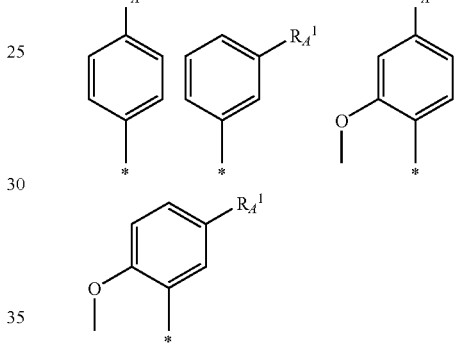

in which
R$_A^1$ is a radical selected independent of its respective occurrence from the group consisting of the respective individual radicals

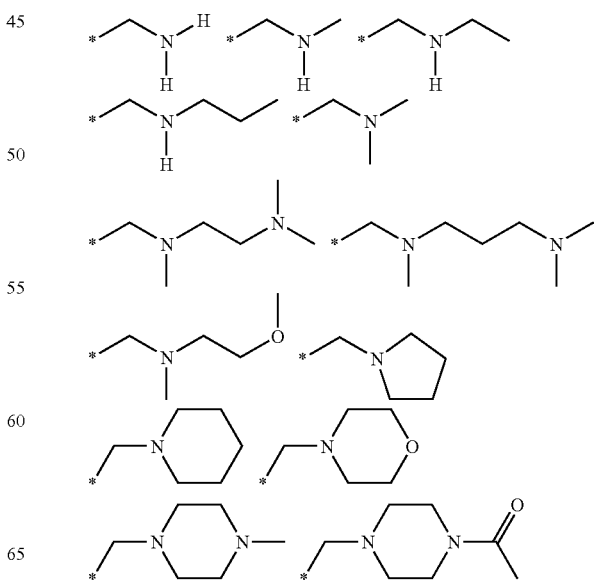

-continued

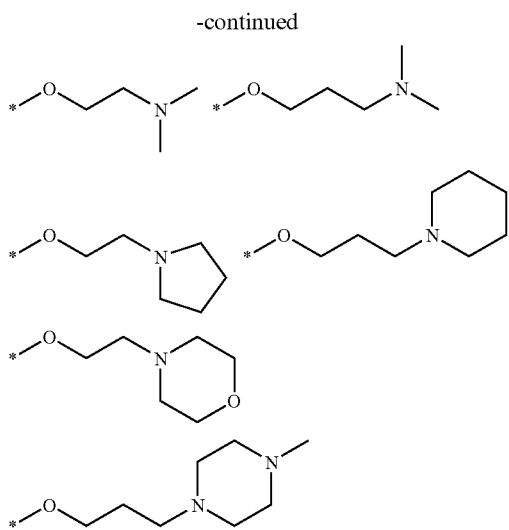

B is a cyclic radical selected from the group consisting of the respective individual radicals

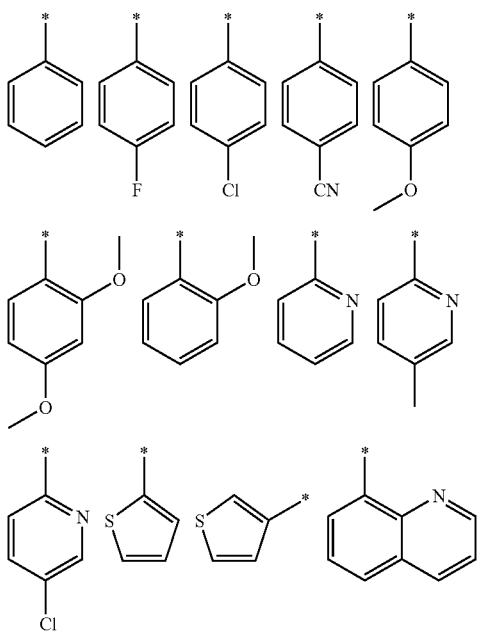

R¹ is chlorine;
R² is hydrogen;
Y is a radical selected from the group consisting of the respective individual radicals

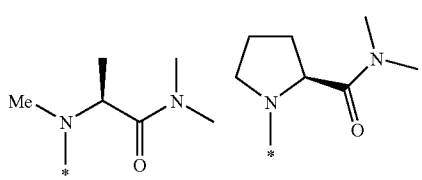

-continued

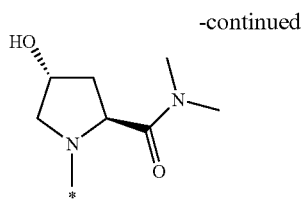

the tautomeric, enantiomeric and diastereomeric forms thereof, and the physiologically tolerated salts of said compound.

7. A compound of the formula (I) as claimed in claim 1, in which
A is a radical selected from the group consisting of the respective individual radicals

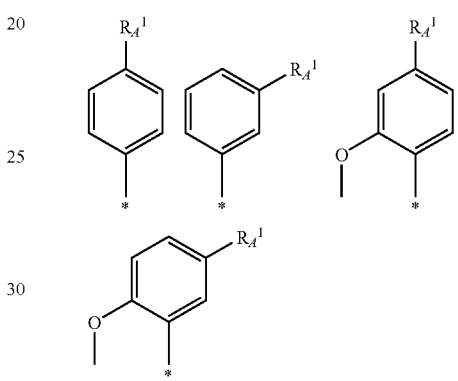

$R_A^1$ is a radical selected independent of its respective occurrence from the group consisting of the respective individual radicals

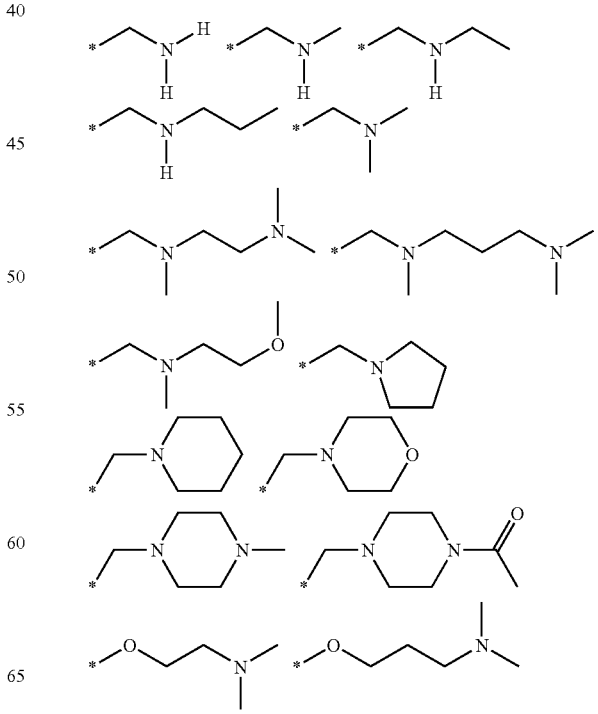

-continued

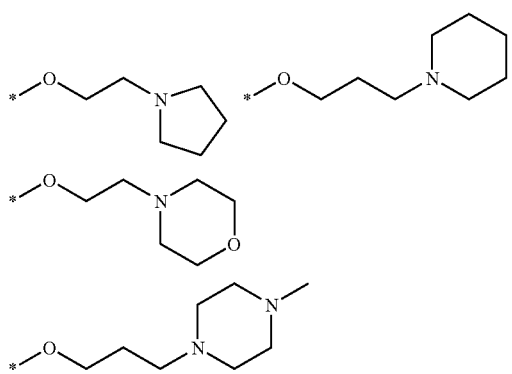

B is a cyclic radical selected from the group consisting of the respective individual radicals

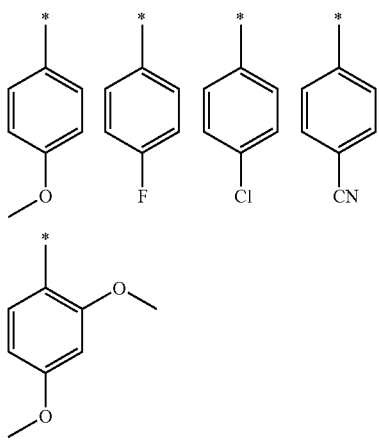

R¹ is chlorine,
R² is hydrogen,
Y is a radical selected from the group consisting of the respective individual radicals

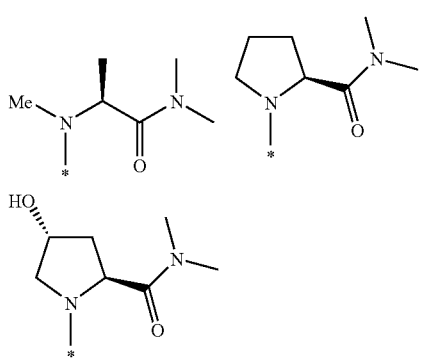

Me is CH₃ the tautomeric, enantiomeric and diastereomeric forms thereof, and the physiologically tolerated salts of said compound.

8. A compound of the formula (I) as claimed in claim 1, in which

A is a cyclic radical selected from the group consisting of the respective individual radicals

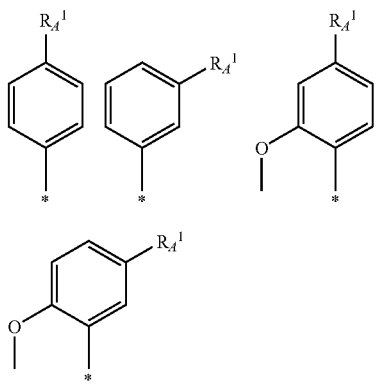

in which
$R_A^1$ is selected from the group consisting of the respective individual radicals

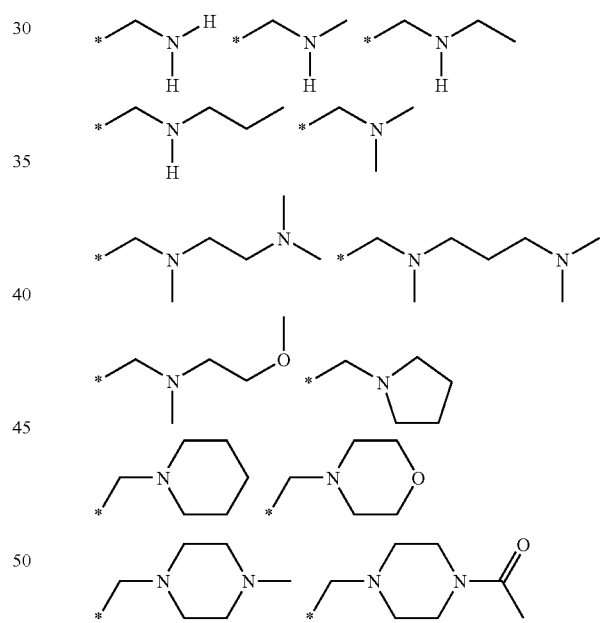

B is a cyclic radical selected from the group consisting of the respective individual radicals

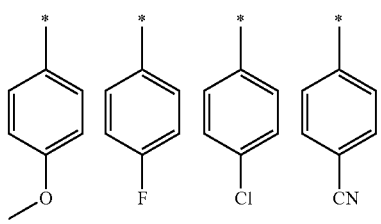

-continued

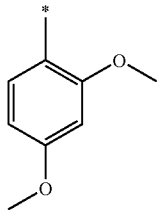

R$^1$ is chlorine,
R$^2$ is hydrogen,
Y is a radical selected from the group consisting of the respective individual radicals

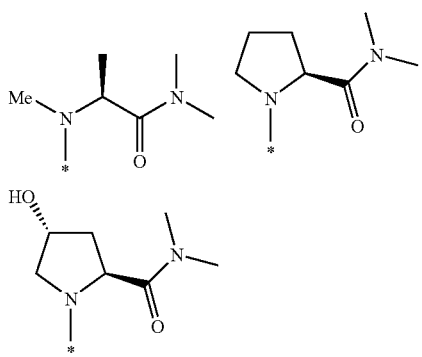

Me is CH$_3$ the tautomeric, enantiomeric and diastereomeric forms thereof, and the physiologically tolerated salts of said compound.

9. A compound of the formula (I) as claimed in claim 1, characterized in that the radical R$^1$ is linked at position 5 of the oxindole ring structure.

10. A compound of the formula (I) as claimed in claim 1, where the compound of the formula (I) is an enriched optically active isomer having an optical purity greater than 50% based on the optically inactive mixture of the isomeric mixture which rotates the plane of polarized light to the left ("negative rotation").

11. A compound of the formula (I) as claimed in claim 1, where the 20 optically active isomer is an enantiomerically enriched diastereomer.

12. A compound of the formula (I) as claimed in claim 1, where the property of "negative rotation" relates to the free base.

13. A compound of the formula (I) as claimed in claim 1, which has a binding affinity Ki for the vasopressin V1b receptor subtype of less than about 100 nM.

14. A compound of the formula (I) as claimed in any claims 1, to 12, which has a selectivity for the vasopressin V1b receptor subtype vis-à-vis the vasopressin V1a receptor subtype, where the quotient of Ki(V1a)/Ki(V1b) is greater than 1.

15. A compound of the formula (I) as claimed in claim 1, which has a selectivity for the vasopressin V1b receptor subtype vis-à-vis the vasopressin V2 receptor subtype, where the quotient of Ki(V2)/Ki(V1b) is greater than 1.

16. A compound of the formula (I) as claimed in claim 1, which has a selectivity for the vasopressin V1b receptor subtype vis-à-vis the oxytocin (OT) receptor, where the quotient of Ki(OT)/Ki(V1b) is greater than 1.

17. A compound of the formula (I) as claimed in claim 1, which has a binding affinity Ki for the vasopressin V1b receptor subtype of less than 100 nM and a selectivity for the vasopressin V1b receptor subtype vis-à-vis the vasopressin V1a receptor subtype, where the quotient of Ki(V1a)/Ki(V1b) is greater than 1.

18. A compound of the formula (I) as claimed in claim 1, which has a binding affinity Ki for the vasopressin V1b receptor subtype of less than 100 nM and a selectivity for the vasopressin V1b receptor subtype vis-à-vis the vasopressin V2 receptor subtype, where the quotient of Ki(V2)/Ki(V1b) is greater than 1.

19. A compound of the formula (I) as claimed in claim 1, which has a binding affinity Ki for the vasopressin V1b receptor subtype of less than 100 nM and a selectivity for the vasopressin V1b receptor subtype vis-à-vis the oxytocin (OT) receptor, where the quotient of Ki(OT)/Ki(V1b) is greater than 1.

20. A compound of the formula (I) as claimed in claim 1, which has a binding affinity Ki for the vasopressin V1b receptor subtype of less than 100 nM and selectivities for the vasopressin V1b receptor subtype vis-à-vis the vasopressin V1a receptor subtype and the vasopressin V2 receptor subtype, where the quotients of Ki(V1a)/Ki(V1b) and Ki(V2)/Ki(V1b) are in each case greater than 1.

21. A compound of the formula (I) as claimed in claim 1, which has a binding affinity Ki for the vasopressin V1b receptor subtype of less than 100 nM and simultaneous selectivities for the vasopressin V1b receptor subtype vis-à-vis the vasopressin V1a receptor subtype and the oxytocin (OT) receptor, where the quotients of Ki(V1a)/Ki(V1b) and Ki(OT)/Ki(V1b) are in each case greater than 1.

22. A compound of the formula (I) as claimed in claim 1, which has a binding affinity Ki for the vasopressin V1b receptor subtype of less than 100 nM and simultaneous selectivities for the vasopressin V1b receptor subtype vis-à-vis the vasopressin V2 receptor subtype and the oxytocin (OT) receptor, where the quotients of Ki(V2)/Ki(V1b) and Ki(OT)/Ki(V1b) are in each case at least greater than 1.

23. A compound of the formula (I) as claimed in claim 1, which has a binding affinity Ki for the vasopressin V1b receptor subtype of less than 100 nM and simultaneous selectivities for the vasopressin V1b receptor subtype vis-à-vis the vasopressin V1a receptor subtype, the vasopressin V2 receptor subtype and the oxytocin (OT) receptor, where the quotients of Ki(V1a)/Ki(V1b), Ki(V2)/Ki(V1b) and Ki(OT)/Ki(V1b) are in each case greater than 1.

24. A pharmaceutical composition comprising at least one compound of the formula (I) as claimed in claim 1, and a pharmaceutically acceptable carrier.

* * * * *